US012760058B2

(12) United States Patent
Xu

(10) Patent No.: US 12,760,058 B2
(45) Date of Patent: Oct. 13, 2026

(54) PRODRUGS OF NEUROACTIVE STEROIDS

(71) Applicant: Brii Biosciences, Inc., Durham, NC (US)

(72) Inventor: Lianhong Xu, Durham, NC (US)

(73) Assignee: Brii Biosciences, Inc., Durham, NC (US)

( * ) Notice: Subject to any disclaimer, the term of this patent is extended or adjusted under 35 U.S.C. 154(b) by 980 days.

(21) Appl. No.: 17/801,894

(22) PCT Filed: Mar. 1, 2021

(86) PCT No.: PCT/US2021/020308

§ 371 (c)(1),
(2) Date: Aug. 24, 2022

(87) PCT Pub. No.: WO2021/174205

PCT Pub. Date: Sep. 2, 2021

(65) Prior Publication Data

US 2023/0416298 A1 Dec. 28, 2023

Related U.S. Application Data

(60) Provisional application No. 62/982,717, filed on Feb. 27, 2020.

(51) Int. Cl.
*C07J 7/00* (2006.01)

(52) U.S. Cl.
CPC .................................... *C07J 7/009* (2013.01)

(58) Field of Classification Search
CPC . C07J 7/009; C07J 17/00; C07J 41/005; C07J 7/002; C07J 43/003; A61P 25/08
See application file for complete search history.

(56) References Cited

U.S. PATENT DOCUMENTS

| | | | |
|---|---|---|---|
| 2013/0338383 A1 | 12/2013 | Chodounska et al. | |
| 2014/0058079 A1 | 2/2014 | Mensah-Nyagan et al. | |
| 2018/0296487 A1 | 10/2018 | Saporito et al. | |
| 2018/0340005 A1* | 11/2018 | Marx | C07J 51/00 |
| 2019/0008875 A1 | 1/2019 | Marsault et al. | |
| 2019/0337975 A1 | 11/2019 | Bryson et al. | |

FOREIGN PATENT DOCUMENTS

| | | | | |
|---|---|---|---|---|
| CN | 108517001 A | 9/2018 | | |
| RU | 2663665 C2 | 8/2018 | | |
| RU | 2696585 C2 | 8/2019 | | |
| WO | WO-9008128 A1 | 7/1990 | | |
| WO | WO-9521617 A1 | 8/1995 | | |
| WO | WO-9616076 A1 | 5/1996 | | |
| WO | WO-2010088409 A2 * | 8/2010 | A61P 25/28 | |
| WO | WO-2011120044 A1 | 9/2011 | | |
| WO | WO-2013056181 A1 | 4/2013 | | |
| WO | WO-2014100228 A1 | 6/2014 | | |
| WO | WO-2015027227 A1 | 2/2015 | | |
| WO | WO-2015081170 A2 | 6/2015 | | |
| WO | WO-2015095971 A1 | 7/2015 | | |
| WO | WO-2018195186 A1 | 10/2018 | | |
| WO | WO-2019211668 A2 | 11/2019 | | |
| WO | WO-2020028787 A1 * | 2/2020 | C07J 7/002 | |
| WO | WO-2020231837 A1 | 11/2020 | | |
| WO | WO-2020243488 A1 | 12/2020 | | |
| WO | WO-2021159021 A1 | 8/2021 | | |
| WO | WO-2021174205 A1 | 9/2021 | | |

OTHER PUBLICATIONS

Bharadwaj, International Journal of Basic and Clinical Pharmacology, 2019, vol. 8, Iss. 5 (Year: 2019).*
Zolkowska, Epilepsia, vol. 159, Iss. S2, 2018, abstract only (Year: 2018).*
Rasmusson, Psychopharmacology, 2017, 234:2245-2257 (Year: 2017).*
Supplementary European Search Report for European Application No. 21761246.4 mailed Apr. 16, 2024, 14 pages.
Bastin et al. "Salt Selection and Optimisation Procedures for Pharmaceutical New Chemical Entities." Organic Process Research & Development. Sep. 15, 2000;4(5):427-435.
Belikov "Pharmaceutical Chemistry. Chapter 2.6 Relationship between the chemical structure, properties of substances and their effect on the body", MEDpress-inform (2007); 14 pages with English translation.
Dyson et al., "Chemistry of Synthetic Drugs", Moscow, MIR, 1964, 25 pages with English machine translation.
Kümmerer "Pharmaceuticals in the Environment", Annual Review of Environment and Resources (2010); 35: 57-75.
Office Action and Search Report for Chinese Application No. CN20218031289 dated May 23, 2024, 9 pages.
Request Substantive Examination and Search Report for Russian Application No. 2022125113 mailed Aug. 27, 2024, 32 pages.
Office Action and Search Report for Chinese Application No. CN20218031289 dated Jul. 24, 2023, 34 pages.
International Search Report and Written Opinion issued by the International Searching Authority for Application No. PCT/US2021/020308, dated Jun. 25, 2021, 11 pages.
Pubchem, SID 355134484, Available Date: Mar. 27, 2018 [retrieved on Mar. 29, 2021]. Retrieved from the Internet: URL: https://pubchem.ncbi.nlm.nih.gov/substance/355134484, 6 pages.
Notice of Reasons for Refusal for Japanese Application No. 2022-551639 mailed Apr. 3, 2025, with English translation, 8 pages.
Office Action and Search Report for Taiwan Application No. 110107352 mailed Mar. 31, 2025, with English Translation, 9 pages.

(Continued)

*Primary Examiner* — Jeffrey H Murray
*Assistant Examiner* — Luisalberto Gonzalez
(74) *Attorney, Agent, or Firm* — COOLEY LLP

(57) ABSTRACT

The present application relates to novel compounds that are prodrugs of brexanolone, ganaxolone and zuranolone, pharmaceutical compositions comprising one or more compounds disclosed herein and salts thereof, and a pharmaceutically acceptable excipient, and use of the compounds disclosed herein and salts thereof for treating diseases or conditions related to $GABA_A$ receptor function, such as major depression disorder (MDD) and postpartum depression (PPD), in mammals and especially in humans.

3 Claims, No Drawings

(56) References Cited

OTHER PUBLICATIONS

AU Application No. 2021226902, Examination report No. 1 mailed Mar. 3, 2026; Applicant Brii Biosciences, Inc., 4 total pages.
Pubchem, Compound ID 355134484, "3beta-Acetoxy-5alph-pregnan-20-one," [compound database record], National Center for Biotechnology Information, record created Mar. 27, 2018. [Accessed on Mar. 29, 2021, publicly available at URL: https://pubchem.ncbi.nlm.nih.gov/substance/355134484], 6 pages.

* cited by examiner

PRODRUGS OF NEUROACTIVE STEROIDS

CROSS REFERENCE TO RELATED APPLICATIONS

This application is a U.S. National Stage Application under 35 U.S.C. 371 of International Application No. PCT/US2021/020308, filed Mar. 1, 2021, which claims the benefit of and priority to U.S. Provisional Application No. 62/982,717, filed Feb. 27, 2020, each of which is herein incorporated by reference in its entirety.

FIELD OF THE DISCLOSURE

The present application relates to novel compounds that are prodrugs of brexanolone, ganaxolone and zuranolone, pharmaceutical compositions comprising one or more of the disclosed compounds and salts thereof, and a pharmaceutically acceptable excipient, and the use of the disclosed compounds and salts thereof for treating diseases and conditions related to $GABA_A$ receptor function, such as major depression disorder (MDD) and postpartum depression (PPD), in mammals and especially in humans.

BACKGROUND OF THE DISCLOSURE

Neuroactive steroids (NASs) encompass neurosteroids (NSs) that are metabolites of cholesterol and synthesized de novo within the brain, as well as steroids that are synthesized in the adrenal glands and gonads. The prime target of NASs is the inhibitory γ-aminobutyric acid (GABA) system. GABA, the primary inhibitory neurotransmitter in the nervous system, acts by activating two types of receptors, $GABA_A$ and $GABA_B$ receptors. GABA regulates neuronal excitability and rapid mood changes via binding of $GABA_A$ receptors, and can influence a wide range of brain circuits and disorders related to GABA function that are central to a variety of behavioral states such as anxiety levels, panic, stress response, seizures, sleep, vigilance and memory.

Given its critical role in the function of neuronal circuits, $GABA_A$ receptors are the target for numerous clinically relevant drugs. Brexanolone (also known as allopregnanolone), ganaxolone and zuranolone are known positive allosteric modulators (PAMs) of the $GABA_A$ receptors, which can prolong the opening time of the $GABA_A$ chloride channel, enhancing inhibitory neurotransmission and causing a global inhibition of central nervous system (CNS). Allopregnanolone (chemical name brexanolone), an endogenous hormone, is produced from progesterone by sequential actions of 5α-reductase and 3α-hydroxysteroid oxidoreductase (3α-HSOR), while ganaxolone and zuranolone are synthetic analogs of allopregnanolone aiming to improve its physicochemical properties and overcome its metabolic liability. ZULRESSO™ (brexanolone), a soluble intravenous formulation of allopregnanolone, was approved by FDA for treatment of PPD on Mar. 19, 2019. ZULRESSO™ (brexanolone) has demonstrated unique therapeutic effects, including a rapid onset of action, high rates of remission and sustained effects after the end of the treatment. However, there are limitations associated with the administration of ZULRESSO™ (brexanolone), which needs to be dosed with a 60-hour continuous intravenous infusion. In addition, loss of consciousness was observed in clinical studies, which was partially attributed to sudden change of brexanolone concentration during the infusion. Although it has improved metabolic stability, ganaxolone needs to be administered at high doses with limited bioavailability when dosed orally.

For treatment of some diseases, such as PPD, ganaxolone also needs to be administered with continuous intravenous infusion.

Thus, there still remains a need to develop new compounds that have improved pharmaceutical or pharmacokinetic properties while acting as modulating agents for the $GABA_A$ receptors.

SUMMARY OF THE DISCLOSURE

In one aspect, the present disclosure provides compounds of Formula (I):

(I)

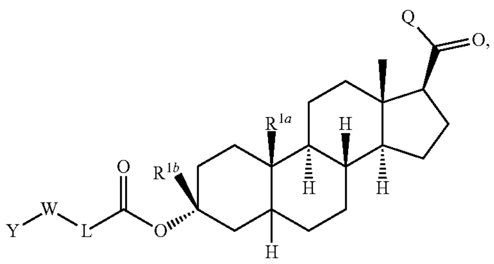

or a pharmaceutically acceptable salt thereof, wherein:

$R^{1a}$ and $R^{1b}$ each is independently hydrogen or methyl;

Q is methyl or

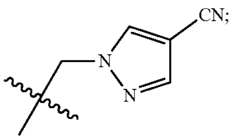 [SMILES: *Cn1cc(C#N)cn1]

L is selected from the group consisting of null, alkyl, —O—, and —N($R^2$)—;

W is selected from the group consisting of null, alkyl, and —O—;

Y is selected from the group consisting of alkyl, alkenyl, alkynyl, heteroalkyl, heteroalkenyl, heteroalkynyl, saturated or unsaturated cycloalkyl, saturated or unsaturated heterocyclyl, aryl, heteroaryl, —OC(O)O$R^3$, —OC(O)$R^4$, and —N$R^5R^6$, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl;

$R^2$, $R^3$, $R^4$ and $R^5$ are each independently selected from the group consisting of hydrogen, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl;

$R^6$ is selected from the group consisting of hydrogen, alkyl, alkenyl, alkynyl, heteroalkyl, heteroalkenyl, heteroalkynyl, and —C(O)$R^7$; and $R^7$ is selected from the group consisting of hydrogen, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, with the provisos that when L is —O— or —N($R^2$)—, W is not —O—, when W is —O—, Y is not —$NR^5NR^6$, and when W is —O—, Y is —C(O)$OR^3$ or —C(O)$R^4$.

In another aspect, there are provided compounds of Formula (Ia):

(Ia)

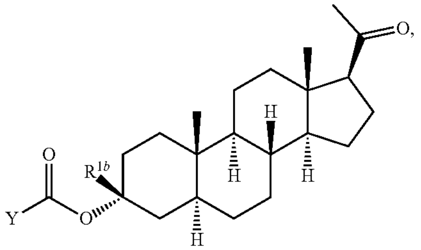

or a pharmaceutically acceptable salt thereof, wherein $R^{1b}$ and Y are as defined in Formula (I).

In another aspect, there are provided compounds of Formula (Ib):

(Ib)

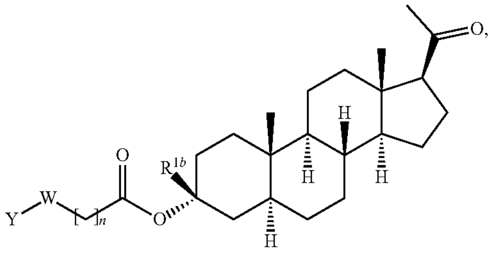

or a pharmaceutically acceptable salt thereof, wherein $R^{1b}$, W and Y are as defined above in Formula (I), and n is an integer from 1 to 10.

In a further aspect, there are provided compounds of Formula (Ic-1):

(Ic-1)

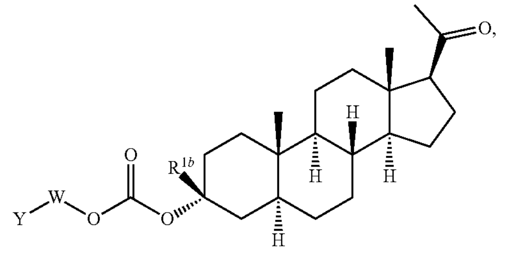

or a pharmaceutically acceptable salt thereof, wherein $R^{1b}$, W and Y are as defined in Formula (I).

In a further aspect, there are provided compounds of Formula (Ic-2):

(Ic-2)

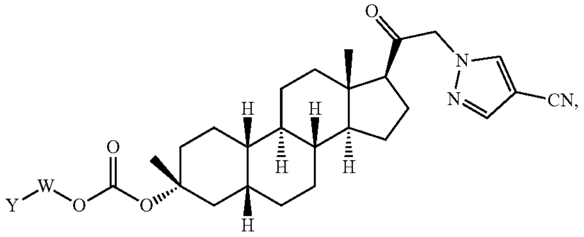

or a pharmaceutically acceptable salt thereof, wherein W and Y are as defined in Formula (I).

In a further aspect, there are provided compounds of Formula (Id-1):

(Id-1)

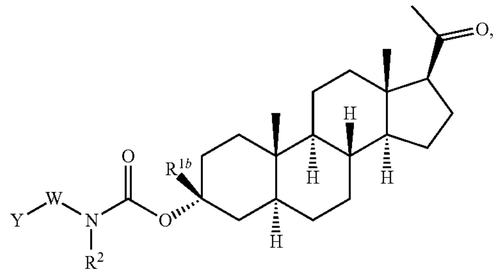

or a pharmaceutically acceptable salt thereof, wherein $R^{1b}$, $R^2$, W and Y are as defined in Formula (I).

In a further aspect, there are provided compounds of Formula (Id-2):

(Id-2)

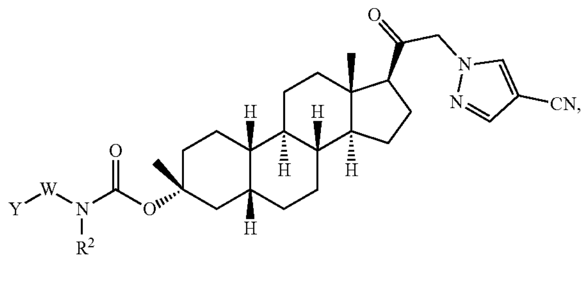

or a pharmaceutically acceptable salt thereof, wherein $R^2$, W and Y are as defined in Formula (I).

In another aspect, there is provided a pharmaceutical composition comprising one or more compounds of Formula (I), Formula (Ia), Formula (Ib), Formula (Ic-1), Formula (Ic-2), Formula (Id-1), Formula (Id-2), or a pharmaceutically acceptable salt thereof, and at least one pharmaceutically acceptable excipient.

In a further aspect, there is provided a method of treating diseases or conditions related to $GABA_A$ receptor function in a subject in need thereof, comprising administering to the subject a therapeutically effective amount of a compound of Formula (I), Formula (Ia), Formula (Ib), Formula (Ic-1), Formula (Ic-2), Formula (Id-1), Formula (Id-2) or a pharmaceutically acceptable salt thereof.

In a further aspect, there is provided a method of treating diseases or conditions related to $GABA_A$ receptor function in a subject in need thereof, comprising administering to the subject a therapeutically effective amount of a composition comprising a compound of Formula (I), Formula (Ia), Formula (Ib), Formula (Ic-1), Formula (Ic-2), Formula (Id-1), Formula (Id-2) or a pharmaceutically acceptable salt thereof, and a pharmaceutically acceptable excipient.

In a further aspect, there is provided a compound of Formula (I), Formula (Ia), Formula (Ib), Formula (Ic-1), Formula (Ic-2), Formula (Id-1), Formula (Id-2) or a pharmaceutically acceptable salt thereof, for use in the treatment of diseases or conditions related to $GABA_A$ receptor function.

In a further aspect, there is provided a use of a compound of Formula (I), Formula (Ia), Formula (Ib), Formula (Ic-1), Formula (Ic-2), Formula (Id-1), Formula (Id-2) or a pharmaceutically acceptable salt thereof, in the manufacture of a medicament for the treatment of diseases or conditions related to $GABA_A$ receptor function.

In a further aspect, there is provided a compound of Formula (I), Formula (Ia), Formula (Ib), Formula (Ic-1), Formula (Ic-2), Formula (Id-1), Formula (Id-2) or a pharmaceutically acceptable salt thereof, administered simultaneously, separately or sequentially with one or more additional agents.

In a further aspect, there is provided a kit for the treatment of diseases or conditions related to $GABA_A$ receptor function, said kit comprising a compound of Formula (I), Formula (Ia), Formula (Ib), Formula (Ic-1), Formula (Ic-2), Formula (Id-1), Formula (Id-2) or a pharmaceutically acceptable salt thereof, a container, and optionally a package insert or label indicating a treatment. The kit may further comprise a second compound or formulation comprising a second pharmaceutical agent useful for treating said disease or disorder.

DETAILED DESCRIPTION OF THE DISCLOSURE

Reference will now be made in detail to certain embodiments of the disclosure, examples of which are illustrated in the accompanying structures and formulas. While the invention will be described in conjunction with the enumerated embodiments, it will be understood that they are not intended to limit the invention to those embodiments. On the contrary, this disclosure is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, $2^{nd}$ Edition, University Science Books, Sausalito, 2006; Smith and March March's Advanced Organic Chemistry, $6^{th}$ Edition, John Wiley & Sons, Inc., New York, 2007; Larock, Comprehensive Organic Transformations, $3^{rd}$ Edition, VCH Publishers, Inc., New York, 2018; Carruthers, Some Modern Methods of Organic Synthesis, $4^{th}$ Edition, Cambridge University Press, Cambridge, 2004; the entire contents of each of which are incorporated herein by reference.

At various places in the present disclosure, linking substituents are described. Where the structure clearly requires a linking group, the Markush variables listed for that group are understood to be linking groups, and the groups to be linked are attached to the linking group at any positions, as long as the valence permits. For example, if the structure requires a linking group and the Markush group definition for that variable lists "alkyl", then it is understood that the "alkyl" represents a linking alkylene group.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R^i$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

As one of ordinary skill in the art would understand, the use of the term "about" indicates that values slightly outside the cited values, i.e., plus or minus 0.1% to 10%.

As used herein, the term "$C_i$-$C_j$" indicates a range of the carbon atoms numbers, wherein i and j are integers and the range of the carbon atoms numbers includes the endpoints (i.e. i and j) and each integer point in between, and wherein j is greater than i. For examples, $C_1$-$C_6$ indicates a range of one to six carbon atoms, including one carbon atom, two carbon atoms, three carbon atoms, four carbon atoms, five carbon atoms and six carbon atoms. In some embodiments, the term "$C_1$-$C_{12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon radical, which may be optionally substituted independently with one or more substituents described below. The term "$C_{i-j}$alkyl" (or "$C_i$-$C_j$ alkyl") refers to an alkyl having i to j carbon atoms. In some embodiments, alkyl groups contain 1 to 12 carbon atoms. In some embodiments, alkyl groups contain 1 to 11 carbon atoms. In some embodiments, alkyl groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of alkyl group include, but are not limited to, methyl, ethyl, 1-propyl (n-propyl), 2-propyl (isopropyl), 1-butyl (n-butyl), 2-methyl-1-propyl (i-butyl), 2-butyl (s-butyl), 2-methyl-2-propyl (t-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Examples of "$C_{1-12}$ alkyl" include, but are not limited to, methyl, ethyl, propyl, butyl, pentyl, hexyl, heptyl, octyl, nonyl, decyl, undecyl, dodecyl. Examples of "$C_{1-6}$ alkyl" are methyl, ethyl, propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2 -methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

The alkyl groups can be further substituted by substituents which independently replace one or more hydrogen atoms on one or more carbons of the alkyl groups. Examples of such substituents can include, but are not limited to, acyl, alkyl, alkenyl, alkynyl, halogen, hydroxyl, alkoxyl, haloalkyl, haloalkoxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfmyl, sulfonate, sulfamoyl, sulfonamido, nitro, trifluoromethyl, cyano, nitro, azido, heterocyclyl, alkylaryl, or an aromatic or heteroaromatic moiety. Alkenyl, alkynyl, saturated or partially unsaturated cycloalkyl, heteroalkyl, heterocyclyl, arylalkyl, heteroarylalkyl, heterocyclylalkyl, cycloalkylalkyl, aryl and heteroaryl groups as described below may also be similarly substituted.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms. In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms. Examples of alkenyl group include, but are not limited to, ethylenyl (or vinyl), propenyl, butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkenyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms. Examples of alkynyl group include, but are not limited to, ethynyl, 1-propynyl, 2-propynyl, and the like.

As used herein, the term "alkoxyl", whether as part of another term or used independently, refers to an alkyl group, as previously defined, attached to the parent molecule through an oxygen atom. The term "$C_{i-j}$alkoxy" (or "$C_i$-$C_j$ alkoxy") means that the alkyl moiety of the alkoxy group has i to j carbon atoms. In some embodiments, alkoxy groups contain 1 to 10 carbon atoms. In some embodiments, alkoxy groups contain 1 to 9 carbon atoms. In some embodiments, alkoxy groups contain 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1-6}$ alkoxyl" include, but are not limited to, methoxy, ethoxy, propoxy (e.g. n-propoxy and isopropoxy), t-butoxy, neopentoxy, n-hexoxy, and the like.

As used herein, the term "aryl", whether as part of another term or used independently, refers to monocyclic and polycyclic ring systems having a total of 5 to 20 ring members, wherein at least one ring in the system is aromatic and wherein each ring in the system contains 3 to 12 ring members. Examples of "aryl" include, but are not limited to, phenyl, biphenyl, naphthyl, anthracyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydroindole), although all of the rings may be aromatic (e.g., quinoline). The second ring can also be fused or bridged. Examples of polycyclic aryl include, but are not limited to, benzofuranyl, indanyl, phthalimidyl, naphthimidyl, phenanthridinyl, or tetrahydronaphthyl, and the like. Aryl groups can be substituted at one or more ring positions with substituents as described above.

As used herein, the terms "cycloalkyl", "carbocyclyl" and "carbocycle" are interchangeable and whether as part of another term or used independently, refer to a monovalent, saturated, partially unsaturated or fully unsaturated monocyclic and polycyclic ring system, in which all the ring atoms are carbon and which contains at least three ring forming carbon atoms. In some embodiments, the cycloalkyl may contain 3 to 12 ring forming carbon atoms ($C_3$-$C_{12}$), 3 to 10 ring forming carbon atoms ($C_3$-$C_{10}$), 3 to 9 ring forming carbon atoms ($C_3$-$C_9$), 3 to 8 ring forming carbon atoms ($C_3$-$C_5$), 3 to 7 ring forming carbon atoms ($C_3$-$C_7$), 3 to 6 ring forming carbon atoms ($C_3$-$C_6$), 3 to 5 ring forming carbon atoms ($C_3$-$C_5$), 4 to 12 ring forming carbon atoms ($C_4$-$C_{12}$), 4 to 10 ring forming carbon atoms ($C_4$-$C_{10}$), 4 to 9 ring forming carbon atoms ($C_4$-$C_9$), 4 to 8 ring forming carbon atoms ($C_4$-$C_8$), 4 to 7 ring forming carbon atoms ($C_4$-$C_7$), 4 to 6 ring forming carbon atoms ($C_4$-$C_6$), 4 to 5 ring forming carbon atoms ($C_4$-$C_5$). Cycloalkyl groups may be saturated or unsaturated. Cycloalkyl groups may be substituted. In some embodiments, the cycloalkyl group may be a saturated cyclic alkyl group. In some embodiments, the cycloalkyl group may be an unsaturated cyclic alkyl group that contains at least one double bond or triple bond in its ring system.

In some embodiments, the cycloalkyl group may be saturated or unsaturated monocyclic carbocyclic ring system, examples of which include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

In some embodiments, the cycloalkyl group may be saturated or unsaturated polycyclic (e.g., bicyclic and tricyclic) carbocyclic ring system, which can be arranged as a fused, spiro or bridged ring system. As used herein, the term "fused ring" refers to a ring system having two rings sharing two adjacent atoms, the term "spiro ring" refers to a ring systems having two rings connected through one single common atom, and the term "bridged ring" refers to a ring system with two rings sharing three or more atoms. Examples of fused carbocyclyl include, but are not limited to, naphthyl, benzopyrenyl, anthracenyl, acenaphthenyl, fluorenyl and the like. Examples of spiro carbocyclyl include, but are not limited to, spiro[5.5]undecanyl, spiropentadienyl, spiro[3.6]-decanyl, and the like. Examples of bridged carbocyclyl include, but are not limited to bicyclo [1,1,1]pentenyl, bicyclo[2,2,1]heptenyl, bicyclo[2.2.1]heptanyl, bicyclo[2.2.2]octanyl, bicyclo[3.3.1]nonanyl, bicyclo [3.3.3]undecanyl, and the like.

As used herein, the term "cyano" refers to —CN.

As used herein, the term "halo" or "halogen" refers to an atom selected from fluorine (or fluoro), chlorine (or chloro), bromine (or bromo) and iodine (or iodo).

As used herein, the term "heteroalkyl" refers to an alkyl, at least one of the carbon atoms of which is replaced with a heteroatom selected from N, O, S, and P. The heteroalkyl may be a carbon radical or heteroatom radical (i.e., the heteroatom may appear in the middle or at the end of the radical), and may be optionally substituted independently with one or more substituents described herein. The term "heteroalkyl" encompasses alkoxy and heteroalkoxy radicals.

As used herein, the term "heteroalkenyl" refers to an alkenyl, at least one of the carbon atoms of which is replaced with a heteroatom selected from N, O, S, and P. The heteroalkenyl may be a carbon radical or heteroatom radical (i.e., the heteroatom may appear in the middle or at the end of the radical), and may be optionally substituted independently with one or more substituents described herein.

As used herein, the term "heteroalkynyl" refers to an alkynyl, at least one of the carbon atoms of which is replaced with a heteroatom selected from N, O, S and P. The heteroalkynyl may be a carbon radical or heteroatom radical (i.e., the heteroatom may appear in the middle or at the end of the radical), and may be optionally substituted independently with one or more substituents described herein.

As used herein, the term "heteroatom" refers to nitrogen, oxygen, sulfur or phosphor, and includes any oxidized form of nitrogen or sulfur, and any quaternized form of a basic nitrogen.

As used herein, the term "heteroaryl", whether as part of another term or used independently, refers to an aryl group having, in addition to carbon atoms, one or more heteroatoms, e.g., one or more heteroatoms selected from the group consisting of N, O, and S. Examples of heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl also includes groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, i benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. In some embodiments, the term "5- to 10-membered heteroaryl" refers to a 5- to 6-membered heteroaryl ring having 1 to 3 heteroatoms independently selected from nitrogen, oxygen, sulfur or phosphorus, or an 8- to 10-membered bicyclic heteroaryl ring having 1 to 4 heteroatoms independently selected from nitrogen, oxygen, sulfur and phosphorus. In certain embodiments, the term "5- to 12-membered heteroaryl" refers to a 5- to 6-membered heteroaryl ring having 1 to 3 heteroatoms independently selected from nitrogen, oxygen, sulfur and phosphorus, or an 8- to 12-membered bicyclic heteroaryl ring having 1 to 4 heteroatoms independently selected from nitrogen, oxygen, sulfur and phosphorus.

As used herein, the term "heterocycle" or "heterocyclyl" refers to a saturated or unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substituents. In some embodiments, the heterocyclyl is a saturated heterocyclyl. In some embodiments, the heterocyclyl is an unsaturated heterocyclyl having one or more double bonds in its ring system. In some embodiments, the heterocyclyl may contains any oxidized form of carbon, nitrogen, sulfur or phosphor, and any quaternized form of a basic nitrogen. "Heterocyclyl" also includes radicals wherein the heterocyclyl radicals are fused with a saturated, partially unsaturated, or fully unsaturated (i.e., aromatic) carbocyclic or heterocyclic ring. The heterocyclyl radical may be carbon linked or nitrogen linked where such is possible. In some embodiments, the heterocycle is carbon linked. In some embodiments, the heterocycle is nitrogen linked. For example, a group derived from pyrrole may be pyrrol-1-yl (nitrogen linked) or pyrrol-3-yl (carbon linked). Further, a group derived from imidazole may be imidazol-1-yl (nitrogen linked) or imidazol-3-yl (carbon linked).

In some embodiments, the term "3- to 12-membered heterocyclyl" refers to a 3- to 12-membered saturated or partially unsaturated monocyclic or polycyclic heterocyclic ring system having 1 to 3 heteroatoms independently selected from nitrogen, oxygen, or sulfur. The fused, spiro and bridged ring systems are also included within the scope of this definition. Examples of monocyclic heterocyclyl include, but are not limited to oxetanyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, pyrrolidinyl, triazinonyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of spiro heterocyclyl include, but are not limited to, spiropyranyl, spirooxazinyl, and the like. Examples of bridged heterocyclyl include, but are not limited to, morphanyl, hexamethylenetetraminyl, 3-aza-bicyclo[3.1.0]hexane, 8-aza-bicyclo[3.2.1]octane, 1-aza-bicyclo[2.2.2]octane, 1,4-diazabicyclo[2.2.2]octane (DABCO), and the like.

As used herein, the term "hydroxyl" or "hydroxy" refers to an —OH group.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

Compounds of the Disclosure

The present disclosure provides novel compounds of Formula (I) and pharmaceutically acceptable salts thereof, synthetic methods for making the compounds, pharmaceutical compositions containing them and various uses of the disclosed compounds in treating diseases and conditions.

In one aspect, the present disclosure provides a compound of Formula (I):

(I)

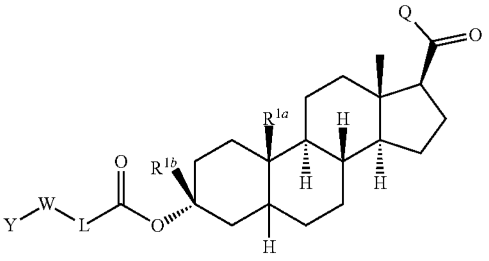

or a pharmaceutically acceptable salt thereof, wherein:

$R^{1a}$ and $R^{1b}$ each is independently hydrogen or methyl;

Q is methyl or

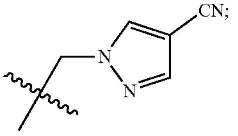 [SMILES: *Cn1cc(C#N)cn1]

L is selected from the group consisting of null, alkyl, —O—, and —N($R^2$)—;

W is selected from the group consisting of null, alkyl, and —O—;

Y is selected from the group consisting of alkyl, alkenyl, alkynyl, heteroalkyl, heteroalkenyl, heteroalkynyl, saturated or unsaturated cycloalkyl, saturated or unsaturated heterocyclyl, aryl, heteroaryl, —OC(O)O$R^3$, —OC(O)$R^4$, and —N$R^5R^6$, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl;

$R^2$, $R^3$, $R^4$ and $R^5$ are each independently selected from the group consisting of hydrogen, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl;

$R^6$ is selected from the group consisting of hydrogen, alkyl, alkenyl, alkynyl, heteroalkyl, heteroalkenyl, heteroalkynyl, and —C(O)$R^7$; and $R^7$ is selected from the group consisting of hydrogen, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl.

In some embodiments of Formula (I), when L is —O— or —N($R^2$)—, W is not —O—, when W is —O—, Y is not —$NR^5NR^6$, and when W is —O—, Y is —C(O)O$R^3$ or —C(O)$R^4$. In some embodiments, when L is —O— or —N($R^2$)—, W is not —O—. In some embodiments, when W is —O—, Y is not —$NR^5NR^6$. In some embodiments, when W is —O—, Y is —C(O)O$R^3$ or —C(O)$R^4$.

In some embodiments, both $R^{1a}$ and $R^{1b}$ are hydrogen. In some embodiments, both $R^{1a}$ and $R^{1b}$ are methyl. In some embodiments, $R^{1a}$ is hydrogen, and $R^{1b}$ is methyl. In some embodiments, one $R^{1a}$ is methyl, and $R^{1b}$ is hydrogen.

In some embodiments, Q is methyl. In some embodiments, Q is

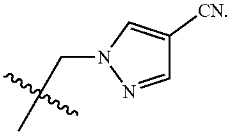 [SMILES: *Cn1cc(C#N)cn1]

In some embodiments, both $R^{1a}$ and $R^{1b}$ are hydrogen, and Q is methyl. In some embodiments, both $R^{1a}$ and $R^{1b}$ are methyl, and Q is methyl. In some embodiments, $R^{1a}$ is hydrogen, $R^{1b}$ is methyl, and Q is

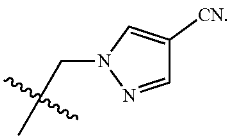 [SMILES: *Cn1cc(C#N)cn1]

In some embodiments, $R^{1a}$ is methyl, $R^{1b}$ is hydrogen, and Q is

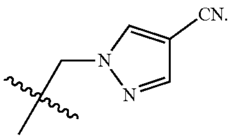 [SMILES: *Cn1cc(C#N)cn1]

In some embodiments, L is null. In some embodiments, L is alkyl, for example, $C_1$-$C_{12}$ alkyl, $C_1$-$C_{11}$ alkyl, $C_1$-$C_{10}$ alkyl, $C_1$-$C_9$ alkyl, $C_1$-$C_8$alkyl, $C_1$-$C_7$ alkyl, $C_1$-$C_6$ alkyl, $C_1$-$C_5$ alkyl, $C_1$-$C_4$ alkyl, $C_1$-$C_3$ alkyl or $C_1$-$C_2$ alkyl. In certain embodiments, L is $C_1$-$C_7$ alkyl. In certain embodiments, L is $C_1$-$C_6$ alkyl. In some embodiments, L is —O—. In some embodiments, L is —N($R^2$)—, and $R^2$ is selected from the group consisting of hydrogen, alkyl, alkenyl, alkynyl, heteroalkyl, heteroalkenyl, and heteroalkynyl. In some embodiments, L is —N($R^2$)—, and $R^2$ is hydrogen or alkyl. In some embodiments, the alkyl is methyl or ethyl. In some embodiments, the alkyl is methyl.

In some embodiments, W is null. In some embodiments, W is alkyl, for example, $C_1$-$C_{12}$ alkyl, $C_1$-$C_{11}$ alkyl, $C_1$-$C_{10}$ alkyl, $C_1$-$C_9$ alkyl, $C_1$-$C_8$alkyl, $C_1$-$C_7$ alkyl, $C_1$-$C_6$ alkyl, $C_1$-$C_5$ alkyl, $C_1$-$C_4$ alkyl, $C_1$-$C_3$ alkyl or $C_1$-$C_2$ alkyl. In certain embodiments, W is $C_1$-$C_6$ alkyl. In some embodiments, W is —O—.

In some embodiments, L is null and W is null. In some embodiments, L is alkyl, and W is null or —O—. In certain embodiments, L is $C_1$-$C_6$ alkyl, and W is null or —O—. In some embodiments, L is $C_1$-$C_6$ alkyl, and W is —O—. In some embodiments, L is —O—, and W is null or alkyl. In some embodiments, L is —O—, and W is alkyl. In some embodiments, L is —O—, and W is $C_1$-$C_6$ alkyl. In some embodiments, L is —O—, and W is alkyl. In some embodiments, L is —O—, and Wis $C_1$ alkyl (i.e., methylene). In some embodiments, L is —N($R^2$)—, W is alkyl, and $R^2$ is selected from the group consisting of hydrogen, alkyl, alkenyl, alkynyl, heteroalkyl, heteroalkenyl, and heteroalkynyl. In certain embodiments, L is —N($R^2$)—, W is alkyl, and $R^2$ is hydrogen. In certain embodiments, L is —N($R^2$)—, W is alkyl, and $R^2$ is alkyl, for example, $C_1$-$C_6$ alkyl, $C_1$-$C_5$ alkyl, $C_1$-$C_4$ alkyl, $C_1$-$C_3$ alkyl or $C_1$-$C_2$ alkyl. In certain embodiments, L is —N($R^2$)—, W is $C_1$-$C_6$ alkyl, and $R^2$ is H, methyl, ethyl, n-propyl or n-butyl. In some embodiments, L is —N($R^2$)—, W is $C_1$-$C_6$ alkyl, and $R^2$ is methyl. In some embodiments, L is —N($R^2$)—, W is $C_1$-$C_6$ alkyl, and $R^2$ is H.

In some embodiments, Y is selected from the group consisting of alkyl, saturated or unsaturated cycloalkyl, saturated or unsaturated heterocyclyl, —OC(O)O$R^3$, —OC(O)$R^4$, and —$NR^5R^6$, wherein said alkyl, saturated or unsaturated cycloalkyl, and saturated or unsaturated heterocyclyl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, with the proviso that when W is —O—, Y is —C(O)O$R^3$ or —C(O)$R^4$. In certain embodiments, Y is alkyl, for example, $C_1$-$C_{12}$ alkyl, $C_1$-$C_{11}$ alkyl, $C_1$-$C_{10}$ alkyl, $C_1$-$C_9$ alkyl, $C_1$-$C_8$alkyl, $C_1$-$C_7$ alkyl, $C_1$-$C_6$ alkyl, $C_1$-$C_5$ alkyl, $C_1$-$C_4$ alkyl, $C_1$-$C_3$ alkyl or $C_1$-$C_2$ alkyl. In certain embodiments, Y is $C_1$-$C_8$alkyl.

In some embodiments, L is null or —O—, W is null, and Y is alkyl, for example, $C_1$-$C_8$alkyl, $C_1$-$C_7$ alkyl, $C_1$-$C_6$ alkyl, $C_1$-$C_5$ alkyl, $C_1$-$C_4$ alkyl, $C_1$-$C_3$ alkyl or $C_1$-$C_2$ alkyl. In some embodiments, L is null or —O—, W is null, and Y is n-propyl, isobutyl, n-butyl, t-butyl, n-pentyl, neopentyl, n-hexyl, or n-heptyl.

In some embodiments, Y is optionally substituted saturated or unsaturated cycloalkyl, for example, 3- to 10-membered saturated cycloalkyl, 3- to 9-membered saturated cycloalkyl, 3- to 8-membered saturated cycloalkyl, 3- to 7-membered saturated cycloalkyl, 3- to 6-membered saturated cycloalkyl, 3- to 5-membered saturated cycloalkyl, 5- to 10-membered unsaturated cycloalkyl, 5- to 9-membered unsaturated cycloalkyl, 5- to 8-membered unsaturated cycloalkyl, 5- to 7-membered unsaturated cycloalkyl, or 5- to 6-membered unsaturated cycloalkyl. In certain embodiments, Y is optionally substituted 3- to 6-membered saturated cycloalkyl or 5- to 6-membered unsaturated cycloalkyl. In some embodiments, Y is cyclopentyl or cyclopentenyl. In certain embodiments, Y is selected from the group consisting of cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and cyclohexadienyl.

In some embodiments, L is alkyl, W is null, and Y is optionally substituted saturated or unsaturated cycloalkyl. In certain embodiments, L is $C_1$-$C_6$ alkyl, W is null, and Y is optionally substituted 3- to 6-membered saturated cycloalkyl or 5- to 6-membered unsaturated cycloalkyl.

In some embodiments, Y is optionally substituted saturated or unsaturated heterocyclyl, for example, 3- to 10-membered saturated heterocyclyl, 3- to 9-membered saturated heterocyclyl, 3- to 8-membered saturated heterocyclyl, 3- to 7-membered saturated heterocyclyl, 3- to 6-membered saturated heterocyclyl, 3- to 5-membered saturated heterocyclyl, 5- to 10-membered unsaturated heterocyclyl, 5- to 9-membered unsaturated heterocyclyl, 5- to 8-membered unsaturated heterocyclyl, 5- to 7-membered unsaturated heterocyclyl, or 5- to 6-membered unsaturated heterocyclyl. In some embodiments, the saturated or unsaturated heterocyclyl is optionally substituted with one or more groups independently selected from oxo, halogen, cyano, alkyl, alkenyl, and alkynyl. In certain embodiments, Y is 3- to 6-membered saturated heterocyclyl or a 5- to 6-membered unsaturated heterocyclyl optionally substituted with one or more groups independently selected from oxo, halogen, cyano, alkyl, alkenyl, and alkynyl. In some embodiments, Y is unsaturated heterocyclyl. In some embodiments, the unsaturated heterocyclyl is a 5- or 6-membered unsaturated heterocyclyl. In some embodiments, the unsaturated heterocyclyl is a 5-membered heterocyclyl having one or two oxygen atoms. In some embodiments, the unsaturated heterocyclyl is a 5-membered heterocyclyl having two oxygen atoms. In some embodiments, the 5-membered heterocyclyl having two oxygen atoms is optionally substituted with one or more oxo or alkyl groups. In some embodiments, the optionally substituted heterocyclyl is

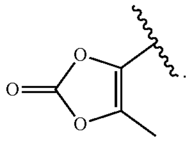 [SMILES: *c1oc(=O)oc1C]

In some embodiments, L is alkyl or —O—, W is null or alkyl, and Y is optionally substituted saturated or unsaturated heterocyclyl. In certain embodiments, L is $C_1$-$C_6$ alkyl or —O—, W is null or $C_1$-$C_6$ alkyl, and Y is 3- to 6-membered saturated heterocyclyl or 5- to 6-membered unsaturated heterocyclyl, optionally substituted with one or more groups independently selected from oxo, halogen, cyano, alkyl, alkenyl, and alkynyl. In some embodiments, L is —O—, W is alkyl, and Y is unsaturated heterocyclyl. In some embodiments, L is —O—, W is $C_1$-$C_6$ alkyl, and Y is unsaturated heterocyclyl. In some embodiments, L is —O—, W is $C_1$ alkyl (i.e., methylene), and Y is unsaturated heterocyclyl. In some embodiments, L is —O—, W is alkyl, and Y is unsaturated 5- or 6-membered heterocyclyl. In some embodiments, L is —O—, W is $C_1$-$C_6$ alkyl, and Y is unsaturated 5- or 6-membered heterocyclyl. In some embodiments, L is —O—, Wis $C_1$ alkyl (i.e., methylene), and Y is unsaturated 5- or 6-membered heterocyclyl. In some embodiments, L is —O—, W is alkyl, and Y is unsaturated

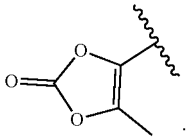 [SMILES: *c1oc(=O)oc1C]

In some embodiments, L is —O—, W is $C_1$-$C_6$ alkyl, and Y is

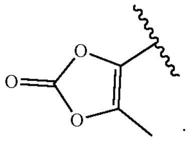 [SMILES: *c1oc(=O)oc1C]

In some embodiments, L is —O—, W is $C_1$ alkyl (i.e., methylene), and Y is

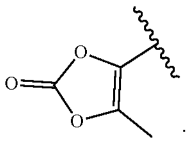 [SMILES: *c1oc(=O)oc1C]

In some embodiments, L is —N($R^2$)—, wherein $R^2$ is hydrogen or -methyl, W is alkyl, and Y is unsaturated

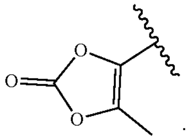 [SMILES: *c1oc(=O)oc1C]

In some embodiments, L is —N($R^2$)—, wherein $R^2$ is hydrogen or -methyl, W is $C_1$-$C_6$ alkyl, and Y is

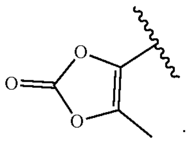 [SMILES: *c1oc(=O)oc1C]

In some embodiments, L is —N($R^2$)—, wherein $R^2$ is hydrogen or -methyl, W is $C_1$ alkyl (i.e., methylene), and Y is

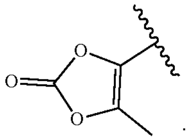 [SMILES: *c1oc(=O)oc1C]

In some embodiments, Y is —OC(O)OR$^3$, wherein R$^3$ is alkyl, for example, $C_1$-$C_6$ alkyl, $C_1$-$C_5$ alkyl, $C_1$-$C_4$ alkyl, $C_1$-$C_3$ alkyl or $C_1$-$C_2$ alkyl. In certain embodiments, Y is —OC(O)OR$^3$, wherein R$^3$ is methyl, ethyl, n-propyl, isopropyl, n-butyl or t-butyl. In some embodiments, R$^3$ is methyl, ethyl or isopropyl. In some embodiments, R$^3$ is methyl or isopropyl. In some embodiments, R$^3$ is optionally substituted aryl, for example, optionally substituted phenyl.

In certain embodiments, L is alkyl, W is —O—, and Y is —C(O)R$^3$, wherein R$^3$ is $C_1$-$C_6$ alkyl. In some embodiments, the $C_1$-$C_6$ alkyl is methyl or isopropyl. In some embodiments, L is —O—, W is alkyl, and Y is —OC(O)OR$^3$, wherein R$^3$ is alkyl. In some embodiments, L is —O—, W is $C_1$-$C_6$ alkyl, and Y is —OC(O)OR$^3$, wherein R$^3$ is alkyl. In some embodiments, L is — O—, W is $C_2$-$C_3$ alkyl, and Y is —OC(O)OR$^3$, wherein R$^3$ is alkyl. In some embodiments, L is —O—, W is alkyl, and Y is —OC(O)OR$^3$, wherein R$^3$ is $C_1$-$C_6$ alkyl. In some embodiments, L is —O—, W is $C_1$-$C_6$ alkyl, and Y is —OC(O)OR$^3$, wherein R$^3$ is $C_1$-$C_6$ alkyl. In some embodiments, L is —O—, W is $C_2$-$C_3$ alkyl, and Y is —OC(O)OR$^3$, wherein R$^3$ is $C_1$-$C_6$ alkyl. In some embodiments, L is —O—, W is alkyl, and Y is —OC(O)OR$^3$, wherein R$^3$ is methyl or isopropyl. In some embodiments, L is —O—, W is $C_1$-$C_6$ alkyl, and Y is —OC(O)OR$^3$, wherein R$^3$ is methyl or isopropyl. In some embodiments, L is —O—, Wis $C_2$-$C_3$ alkyl, and Y is —OC(O)OR$^3$, wherein R$^3$ is methyl or isopropyl.

In some embodiments, Y is —OC(O)R$^4$, wherein R$^4$ is alkyl, for example, $C_1$-$C_6$ alkyl, $C_1$-$C_5$ alkyl, $C_1$-$C_4$ alkyl, $C_1$-$C_3$ alkyl or $C_1$-$C_2$ alkyl. In certain embodiments, Y is —OC(O)R$^4$, wherein R$^4$ is methyl, ethyl, n-propyl, isopropyl, n-butyl or t-butyl. In some embodiments, the R$^4$ is methyl or isopropyl.

In certain embodiments, L is —O— or —N(R$^2$)—, W is alkyl, and Y is —OC(O)R$^4$, wherein R$^2$ is hydrogen or alkyl, and R$^4$ is alkyl. In certain embodiments, L is —O— or —N(R$^2$)—, W is $C_1$-$C_6$ alkyl, and Y is —OC(O)R$^4$, wherein R$^2$ is hydrogen or alkyl, and R$^4$ is alkyl. In certain embodiments, L is —O— or —N(R$^2$)—, W is $C_2$-$C_3$ alkyl, and Y is —OC(O)R$^4$, wherein R$^2$ is hydrogen or alkyl, and R$^4$ is alkyl. In certain embodiments, L is —O— or —N(R$^2$)—, W is alkyl, and Y is —OC(O)R$^4$, wherein R$^2$ is hydrogen or $C_1$-$C_6$ alkyl, R$^4$ is $C_1$-$C_6$ alkyl. In certain embodiments, L is —O— or —N(R$^2$)—, W is $C_1$-$C_6$ alkyl, and Y is —OC(O) R$^4$, wherein R$^2$ is hydrogen or $C_1$-$C_6$ alkyl, R$^4$ is $C_1$-$C_6$ alkyl. In certain embodiments, L is —O— or —N(R$^2$)—, W is $C_2$-$C_3$ alkyl, and Y is —OC(O)R$^4$, wherein R$^2$ is hydrogen or $C_1$-$C_6$ alkyl, R$^4$ is $C_1$-$C_6$ alkyl. In certain embodiments, L is —O— or —N(R$^2$)—, W is alkyl, and Y is —OC(O)R$^4$, wherein R$^2$ is hydrogen or Me, R$^4$ is methyl, ethyl, or isopropyl. In certain embodiments, L is —O— or —N(R$^2$)—, W is $C_1$-$C_6$ alkyl, and Y is —OC(O)R$^4$, wherein R$^2$ is hydrogen or Me, R$^4$ is methyl, ethyl, or isopropyl. In certain embodiments, L is —O— or —N(R$^2$)—, Wis $C_2$-$C_3$ alkyl, and Y is —OC(O)R$^4$, wherein R$^2$ is hydrogen or Me, R$^4$ is methyl, ethyl, or isopropyl. In some embodiments, L is —O—. In some embodiments, L is —N(R$^2$)—. In some embodiments, R$^2$ is hydrogen or methyl. In some embodiments, the R$^4$ is methyl or isopropyl.

In some embodiments, Y is —NR$^5$R$^6$, wherein R$^5$ is hydrogen or alkyl, R$^6$ is —C(O)R$^7$, and R$^7$ is alkyl or alkoxyl. In certain embodiments, Y is —NR$^5$R$^6$, wherein R$^5$ is hydrogen or $C_1$-$C_6$ alkyl, R$^6$ is —C(O)R$^7$, and R$^7$ is $C_1$-$C_6$ alkyl or $C_1$-$C_6$ alkoxyl. In some embodiments, R$^5$ is hydrogen or methyl, R$^6$ is —C(O)R$^7$, and R$^7$ is —$CH_3$, —CH $(CH_3)_2$, —$OCH_3$, or —$OCH(CH_3)$ 2. In some embodiments, R$^5$ is hydrogen or methyl, and R$^6$ is —C(O)$CH_3$, —C(O) $CH(CH_3)_2$, —C(O)$OCH_3$, or —C(O)$OCH(CH_3)$ 2.

In some embodiments, L is —O—, W is alkyl, Y is —NR$^5$R$^6$, wherein R$^5$ is hydrogen or alkyl, R$^6$ is —C(O)R$^7$, R$^7$ is alkyl or alkoxyl. In certain embodiments, L is —O—, W is $C_1$-$C_6$ alkyl, Y is —NRSR$_6$, wherein R$^5$ is hydrogen or $C_1$-$C_6$ alkyl, R$^6$ is —C(O)R$^7$, and R$^7$ is $C_1$-$C_6$ alkyl or $C_1$-$C_6$ alkoxyl. In certain embodiments, L is —O—, W is $C_1$-$C_6$ alkyl, Y is —NR$^5$R$^6$, wherein R$^5$ is hydrogen or methyl, and R$^6$ is —C(O)$CH_3$, —C(O)$CH(CH_3)_2$, —C(O)$OCH_3$, or —C(O)$OCH(CH_3)$ 2. In certain embodiments, L is —O—, W is alkyl, and Y is —NR$^5$R$^6$, wherein R$^5$ is H or $C_1$-$C_3$ alkyl, R$^6$ is —C(O)R$^7$, and R$^7$ is alkyl or alkoxyl. In certain embodiments, L is —O—, W is $C_1$-$C_6$ alkyl, and Y is —NR$^5$R$^6$, wherein R$^5$ is H or $C_1$-$C_3$ alkyl, R$^6$ is —C(O)R$^7$, and R$^7$ is alkyl or alkoxyl. In certain embodiments, L is —O—, W is $C_2$-$C_3$ alkyl, and Y is —NR$^5$R$^6$, wherein R$^5$ is H or $C_1$-$C_3$ alkyl, R$^6$ is —C(O)R$^7$, and R$^7$ is alkyl or alkoxyl. In certain embodiments, L is —O—, W is alkyl, and Y is —NR$^5$R$^6$, wherein R$^5$ is H or $C_1$-$C_3$ alkyl, R$^6$ is —C(O)R$^7$, and R$^7$ is $C_1$-$C_6$ alkyl or $C_1$-$C_6$ alkoxyl. In certain embodiments, L is —O—, W is $C_1$-$C_6$ alkyl, and Y is —NR$^5$R$^6$, wherein R$^5$ is H or $C_1$-$C_3$ alkyl, R$^6$ is —C(O)R$^7$, and R$^7$ is $C_1$-$C_6$ alkyl or $C_1$-$C_6$ alkoxyl. In certain embodiments, L is —O—, W is $C_2$-$C_3$ alkyl, and Y is —NR$^5$R$^6$, wherein R$^5$ is H or $C_1$-$C_3$ alkyl, R$^6$ is —C(O)R$^7$, and R$^7$ is $C_1$-$C_6$ alkyl or $C_1$-$C_6$ alkoxyl. In certain embodiments, L is —O—, W is alkyl, and Y is —NR$^5$R$^6$, wherein R$^5$ is H or $C_1$-$C_3$ alkyl, R$^6$ is —C(O)R$^7$, and R$^7$ is $C_1$-$C_3$ alkyl or $C_1$-$C_3$ alkoxyl. In certain embodiments, L is —O—, W is $C_1$-$C_6$ alkyl, and Y is —NR$^5$R$^6$, wherein R$^5$ is H or $C_1$-$C_3$ alkyl, R$^6$ is —C(O) R$^7$, and R$^7$ is $C_1$-$C_3$ alkyl or $C_1$-$C_3$ alkoxyl. In certain embodiments, L is —O—, W is $C_2$-$C_3$ alkyl, and Y is —NR$^5$R$^6$, wherein R$^5$ is H or $C_1$-$C_3$ alkyl, R$^6$ is —C(O)R$^7$, and R$^7$ is $C_1$-$C_3$ alkyl or $C_1$-$C_3$ alkoxyl. In certain embodiments, L is —O—, W is alkyl, and Y is —NR$^5$R$^6$, wherein R$^5$ is H or $C_1$-$C_3$ alkyl, R$^6$ is —C(O)R$^7$, and R$^7$ is —$CH_3$, —$CH(CH_3)_2$, —$OCH_3$, or —$OCH(CH_3)$ 2. In certain embodiments, L is —O—, W is $C_1$-$C_6$ alkyl, and Y is —NR$^5$R$^6$, wherein R$^5$ is H or $C_1$-$C_3$ alkyl, R$^6$ is —C(O)R$^7$, and R$^7$ is —$CH_3$, —$CH(CH_3)_2$, —$OCH_3$, or —$OCH(CH_3)$ 2. In certain embodiments, L is —O—, W is $C_2$-$C_3$ alkyl, and Y is —NR$^5$R$^6$, wherein R$^5$ is H or $C_1$-$C_3$ alkyl, R$^6$ is —C(O)R$^7$, and R$^7$ is —$CH_3$, —$CH(CH_3)_2$, —$OCH_3$, or —$OCH(CH_3)$ 2.

In some embodiments, the compounds of the present disclosure have a Formula (Ia) of:

(Ia)

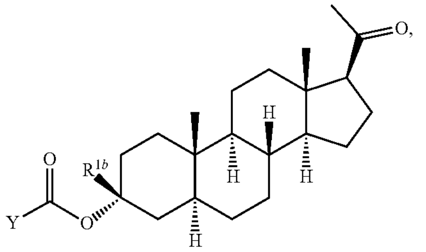

wherein R$^{1b}$ and Y are defined as above in Formula (I).

In certain embodiments, R$^{1b}$ is hydrogen or methyl, Y is alkyl, for example, $C_1$-$C_{12}$ alkyl, $C_1$-$C_{11}$ alkyl, $C_1$-$C_{10}$ alkyl, $C_1$-$C_9$ alkyl, $C_1$-$C_8$alkyl, $C_1$-$C_7$ alkyl, $C_1$-$C_6$ alkyl, $C_1$-$C_5$ alkyl, $C_1$-$C_4$ alkyl, $C_1$-$C_3$ alkyl or $C_1$-$C_2$ alkyl.

In some embodiments, the compounds of the present disclosure have a Formula (Ib) of:

(Ib)

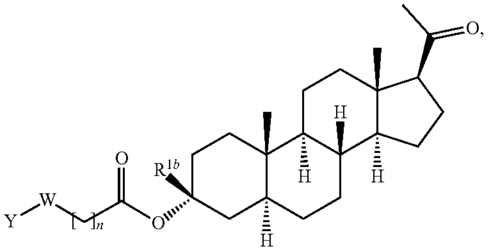

wherein

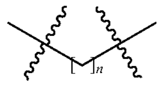

is optionally substituted with alkyl group (e.g., methyl, ethyl, or isopropyl), n is integer from 1-5, and $R^{1b}$, W, and Y are defined as above in Formula (I).

In certain embodiments, $R^{1b}$ is hydrogen or methyl, and W is null or —O—. In certain embodiments, $R^{1b}$ is hydrogen or methyl, W is null or —O—, and Y is saturated or unsaturated cycloalkyl, saturated or unsaturated heterocyclyl, or —OC(O)OR$^3$, wherein $R^3$ is hydrogen or alkyl, wherein said cycloalkyl and heterocyclyl are optionally substituted with one or more groups independently selected from oxo, halogen, cyano, alkyl, alkenyl, and alkynyl. In certain embodiments, $R^{1b}$ is hydrogen or methyl, W is null or —O—, and Y is 3- to 6-membered saturated or unsaturated cycloalkyl, 3- to 6-membered saturated or unsaturated heterocyclyl, or —OC(O)OR$^3$, wherein $R^3$ is hydrogen or $C_1$-$C_6$ alkyl, wherein said cycloalkyl and heterocyclyl are optionally substituted with one or more groups independently selected from oxo, halogen, cyano, alkyl, alkenyl, and alkynyl.

In some embodiments, the compounds of the present disclosure have a Formula (Ic-1) or Formula (Ic-2) of:

(Ic-1)

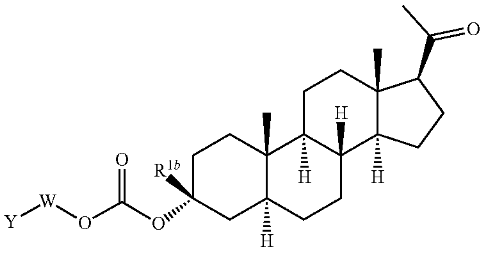

-continued (Ic-2)

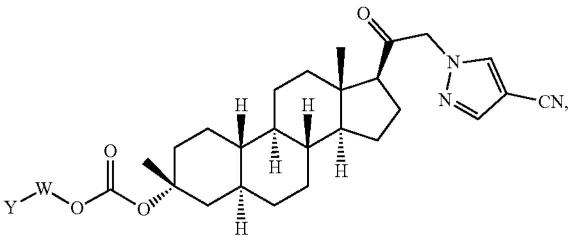

wherein $R^{1b}$, W, and Y are defined as above in Formula (I).

In certain embodiments, $R^{1b}$ is hydrogen or methyl, W is null or alkyl. In certain embodiments, $R^{1b}$ is hydrogen or methyl, W is null or alkyl, and Y is selected from the group consisting of alkyl, saturated or unsaturated heterocyclyl, —OC(O)R$^4$, and —NR$^5$R$^6$, wherein $R^4$ and $R^5$ are each selected from the group consisting of hydrogen, alkyl, alkenyl, and alkynyl, $R^6$ is —C(O)R$^7$, and $R^7$ is selected from the group consisting of hydrogen, alkyl, alkenyl, alkynyl, and alkoxyl, wherein said alkyl, alkenyl, alkynyl, alkoxyl, and saturated or unsaturated heterocyclyl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl. In certain embodiments, $R^{1b}$ is hydrogen or methyl, W is alkyl, and Y is selected from the group consisting of unsaturated heterocyclyl, —OC(O)R$^4$, and —NR$^5$R$^6$, wherein $R^4$ and $R^5$ are each selected from the group consisting of hydrogen, alkyl, alkenyl, and alkynyl, $R^6$ is —C(O)R$^7$, and $R^7$ is selected from the group consisting of hydrogen, alkyl, alkenyl, alkynyl, and alkoxyl, wherein said alkyl, alkenyl, alkynyl, alkoxyl, and saturated or unsaturated heterocyclyl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl.

In certain embodiments, $R^{1b}$ is hydrogen or methyl, Wis $C_1$-$C_6$ alkyl, and Y is selected from the group consisting of 5- to 6 membered unsaturated heterocyclyl optionally substituted with one or more oxo groups, —OC(O)R$^4$, and —NR$^5$R$^6$, wherein $R^4$ and $R^5$ are each hydrogen or $C_1$-$C_6$ alkyl, $R^6$ is —C(O)R$^7$, and $R^7$ is $C_1$-$C_6$ alkyl or $C_1$-$C_6$ alkoxyl.

In some embodiments, the compounds of the present disclosure have a Formula (Id-1) or Formula (Id-2) of:

(Id-1)

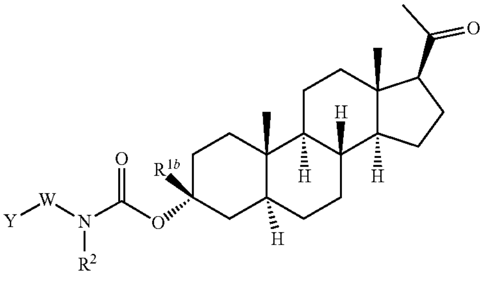

-continued (Id-2)

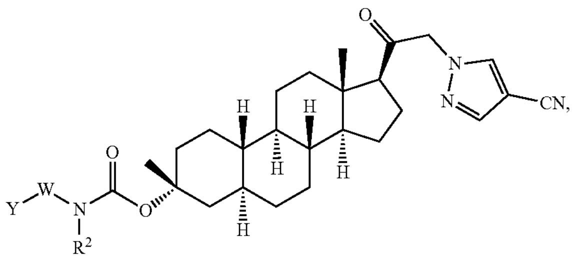

wherein $R^{1b}$, $R^2$, W, and Y are defined as above in Formula (I).

In certain embodiments, $R^{1b}$ is hydrogen or methyl, and $R^2$ is hydrogen or alkyl. In certain embodiments, $R^{1b}$ is hydrogen or methyl, and $R^2$ is hydrogen or methyl.

In certain embodiments, $R^{1b}$ is hydrogen or methyl, $R^2$ is hydrogen or alkyl, and W is alkyl. In certain embodiments, $R^{1b}$ is hydrogen or methyl, $R^2$ is hydrogen or alkyl, W is alkyl, and Y is —OC(O)$R^4$, wherein $R^4$ is selected from the group consisting of hydrogen, alkyl, alkenyl, and alkynyl. In certain embodiments, $R^{1b}$ is hydrogen or methyl, $R^2$ is hydrogen or $C_1$-$C_6$ alkyl, W is $C_1$-$C_6$ alkyl, and Y is —OC(O)$R^4$, wherein $R^4$ is hydrogen or $C_1$-$C_6$ alkyl.

In certain embodiments, the present disclosure provides a compound of Table 1.

In a further aspect, the present disclosure provides a compound of Formula (I) or a pharmaceutically acceptable salt thereof selected from the group consisting of:

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]hexanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]heptanoate, (3R,5S,8R,9S,10S,13S,14S,17S)-17-acetyl-10,13-dimethyl-hexadecahydro-1H-cyclopenta[a]phenanthren-3-yl ocatanoate,

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl]hexanoate,

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl]heptanoate,

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl]octanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylacetate,

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl] 3-cyclopentylpropanoate,

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl] 2-cyclopentylacetate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopent-3-en-1-ylpropanoate,

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl] 3-cyclopent-3-en-1-yl-propanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-(5-oxotetrahydro-furan-2-yl)propanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-acetoxybutanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-(2-methylpropanoyloxy) butanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-acetoxyp entanoate,

[(3R,5S,8R,9S,10S,13S,14S,17S)-17-acetyl-10,13-dimethyl-2,3,4,5,6,7,8,9,11,12,14, 15,16,17-tetradecahydro-1H-cyclopenta[a]phenanthren-3-yl] 5-acetoxy-2-methyl-pentanoate, 3-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]propyl acetate, 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy] ethyl 2-methylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]butyl carbonate, 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonylamino] ethyl 2-methylpropanoate, 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyl-methyl-amino]ethyl 2-methylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate), (3R,5S,8R,9S,10S,13S,14S,17S)-17-acetyl-10,13-dimethyl-hexadecahydro-1H-cycl penta[a]phenanthren-3-yl(2-(N-methylisobutyramido)ethyl)carbonate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonylamino)ethyl carbonate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonyl-N-methyl amino)ethyl carbonate, (3R,5S,8R,9S,10S,13S,14S,17S)-17-acetyl-3,10,13-trimethylhexadecahydro-1H-cyclopenta[a]phenanthren-3-yl ((5-methyl-2-oxo-1,3-dioxol-4-yl)methyl)carbonate, 2-(((((3R,5S,8R,9S,10S,13S,14S,17S)-17-acetyl-3,10,13-trimethylhexadecahydro-1H-cyclopenta[a]phenanthren-3-yl)oxy)carbonyl)(methyl)amino)ethyl isobutyrate, 2-(((((3R,5S,8R,9S,10S,13S,14S,17S)-17-acetyl-3,10,13-trimethylhexadecahydro-1H-cyclopenta[a]phenanthren-3-yl)oxy)carbonyl)oxy)ethyl isobutyrate, (3R,5R,8R,9R,10S,13S,14S,17S)-17-(2-(4-cyano-1H-pyrazol-1-yl) acetyl)-3,13-dimethylhexadecahydro-1H-cyclopenta[a]phenanthren-3-yl ((5-methyl-2-oxo-1,3-dioxol-4-yl)methyl)carbonate, 2-(((((3R,5R,8R,9R,10S,13S,14S,17S)-17-(2-(4-cyano-1H-pyrazol-1-yl) acetyl)-3,13-dimethylhexadecahydro-1H-cyclopenta[a]phenanthren-3-yl)oxy)carbonyl)(methyl)amino)ethyl isobutyrate, and 2-(((((3R,5R,8R,9R,10S,13S,14S,17S)-17-(2-(4-cyano-1H-pyrazol-1-yl) acetyl)-3,13-dimethylhexadecahydro-1H-cyclopenta[a]phenanthren-3-yl)oxy)carbonyl)oxy)ethyl isobutyrate.

Exemplary compounds of Formula (I) are set forth in Table 1 below.

TABLE 1

| Cmpd No. | Compound Structure and Name |
|---|---|
| 1 | 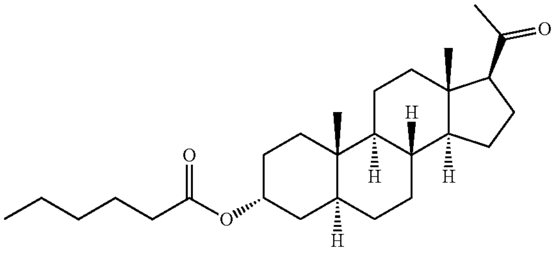 [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]hexanoate |
| 2 | 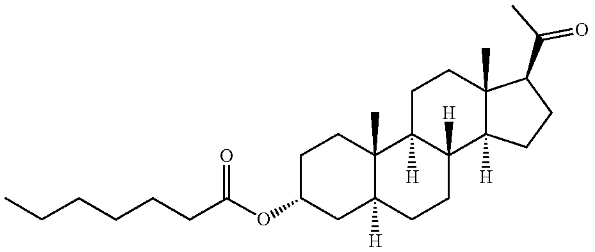 [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]heptanoate |
| 3 | 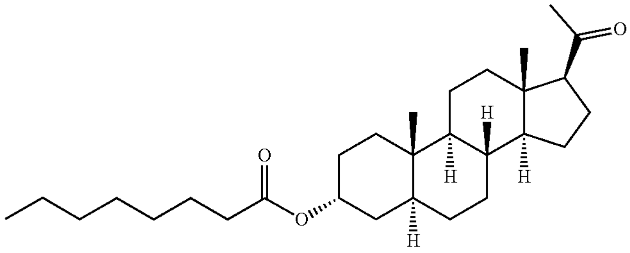 (3R,5S,8R,9S,10S,13S,14S,17S)-17-acetyl-10,13-dimethylhexadecahydro-1H-cyclopenta[a]phenanthren-3-yl ocatanoate |
| 4 | 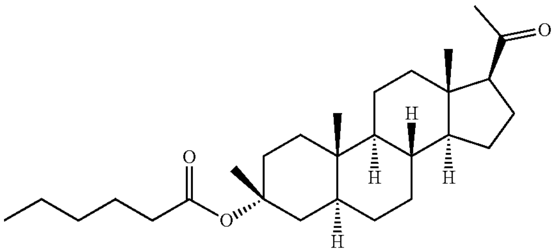 [(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]hexanoate |

TABLE 1-continued

| Cmpd No. | Compound Structure and Name |
|---|---|
| 5 | 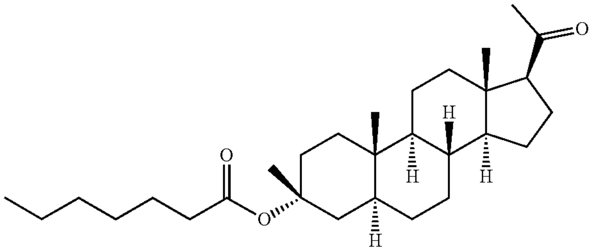<br>[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]heptanoate |
| 6 | 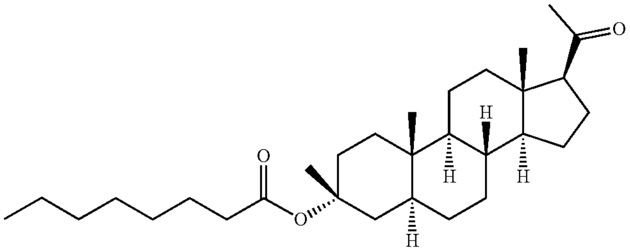<br>[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]octanoate |
| 7 | 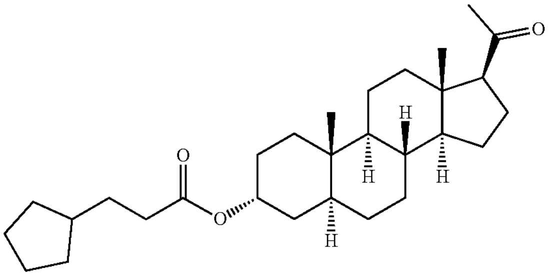<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylpropanoate |
| 8 | 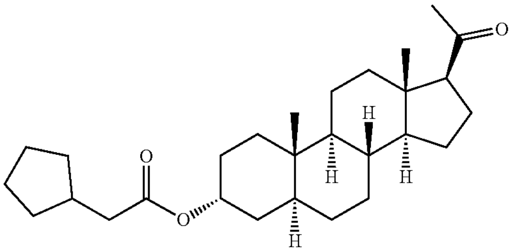<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylacetate |

TABLE 1-continued

| Cmpd No. | Compound Structure and Name |
|---|---|
| 9 | 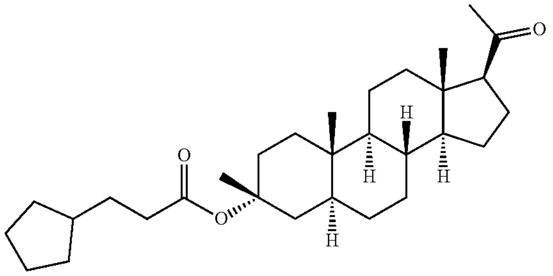 [(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 3-cyclopentylpropanoate |
| 10 | 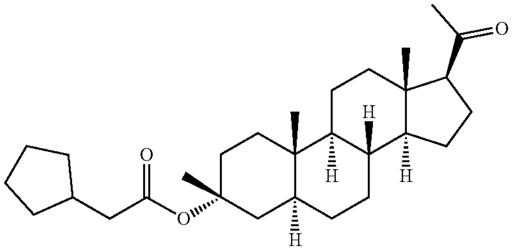 [(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 2-cyclopentylacetate |
| 11 | 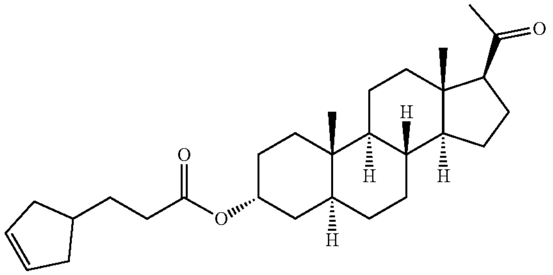 [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopent-3-en-1-ylpropanoate |
| 12 | 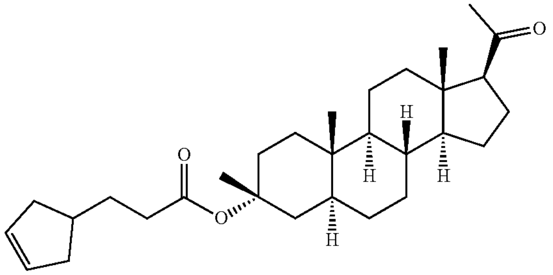 [(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 3-cyclopent-3-en-1-ylpropanoate |

TABLE 1-continued

| Cmpd No. | Compound Structure and Name |
|---|---|
| 13 | 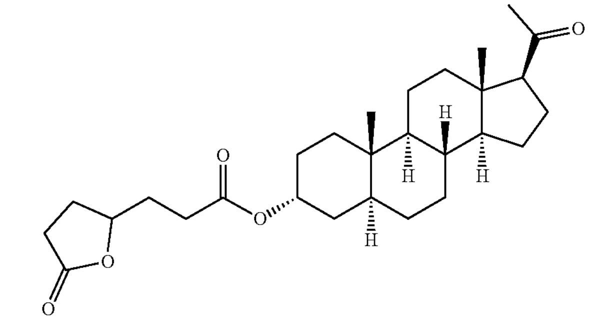<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-(5-oxotetrahydrofuran-2-yl)propanoate |
| 14 | 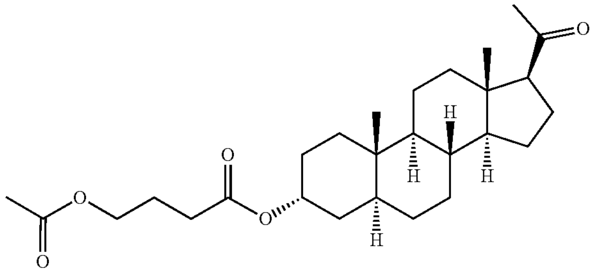<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]4-acetoxybutanoate |
| 15 | 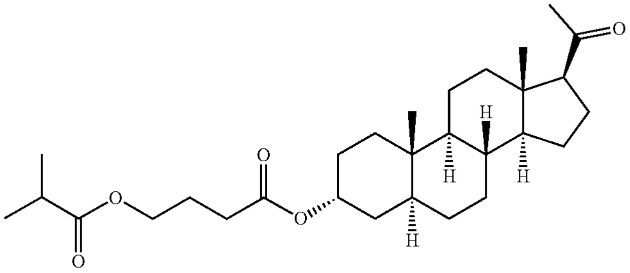<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]4-(2-methylpropanoyloxy)butanoate |
| 16 | 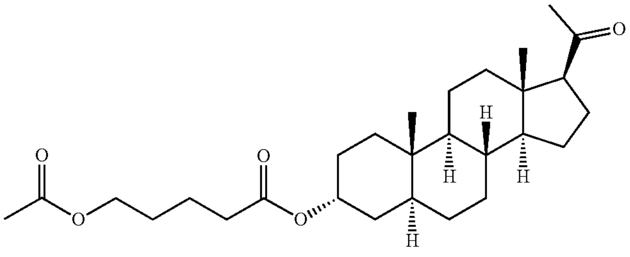<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-acetoxypentanoate |

TABLE 1-continued

| Cmpd No. | Compound Structure and Name |
|---|---|
| 17 | 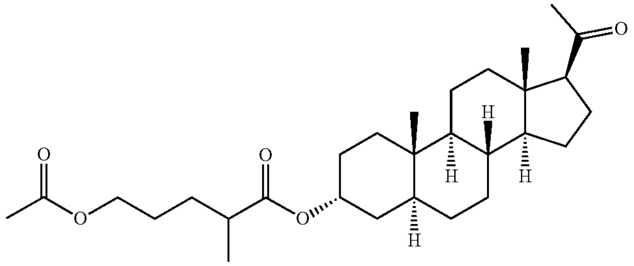<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]5-acetoxy-2-methyl-pentanoate |
| 18 | 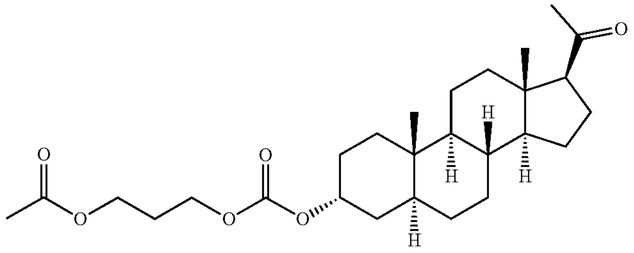<br>3-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]propyl acetate |
| 19 | 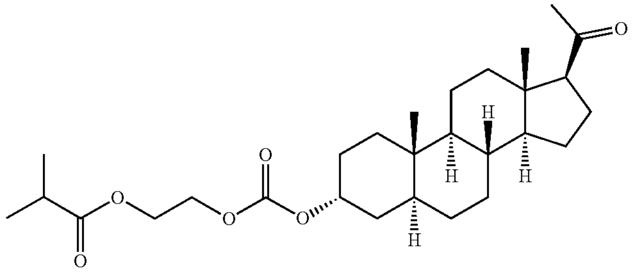<br>2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]ethyl 2-methylpropanoate |
| 20 | 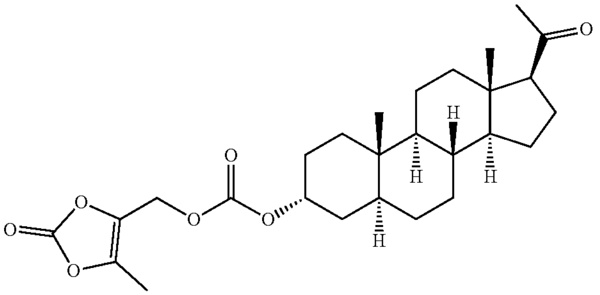<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl](5-methyl-2-oxo-1,3-dioxol-4-yl)methyl carbonate |

TABLE 1-continued

| Cmpd No. | Compound Structure and Name |
| --- | --- |
| 21 | 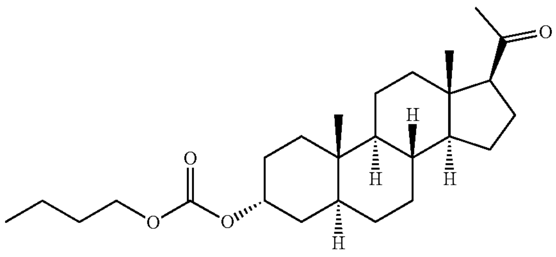<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] butyl carbonate |
| 22 | 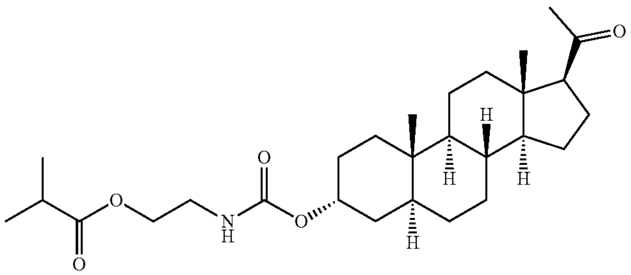<br>2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonylamino]ethyl 2-methylpropanoate |
| 23 | 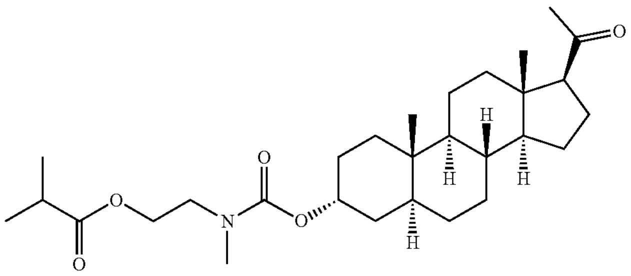<br>2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyl-methyl-amino]ethyl 2-methylpropanoate |
| 24 | 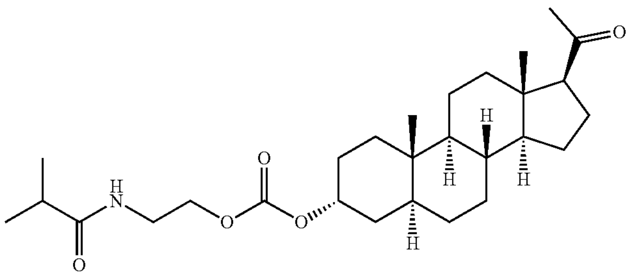<br>[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate) |

TABLE 1-continued

| Cmpd No. | Compound Structure and Name |
| --- | --- |
| 25 | 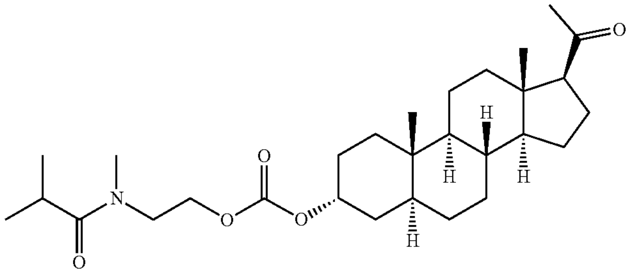 (3R,5S,8R,9S,10S,13S,14S,17S)-17-acetyl-10,13-dimethylhexadecahydro-1H-cycl penta[a]phenanthren-3-yl(2-(N-methylisobutyramido)ethyl) carbonate |
| 26 | 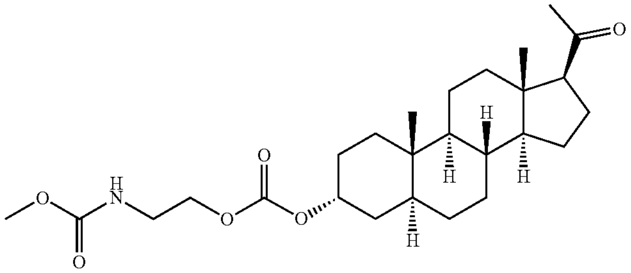 [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]2-(methoxycarbonylamino)ethyl carbonate |
| 27 | 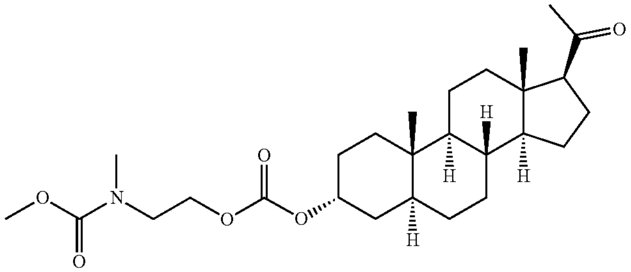 [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]2-(methoxycarbonyl-N-methyl amino)ethyl carbonate |
| 28 | 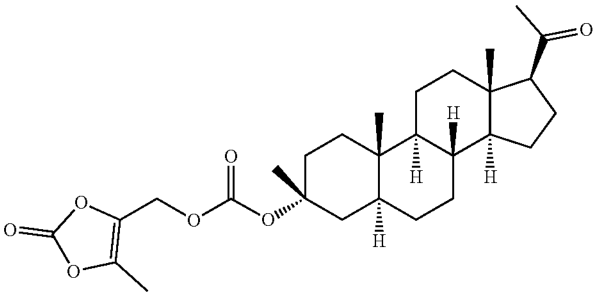 (3R,5S,8R,9S,10S,13S,14S,17S)-17-acetyl-3,10,13-trimethylhexadecahydro-1H-cyclopenta[a]phenanthren-3-yl ((5-methyl-2-oxo-1,3-dioxol-4-yl)methyl) carbonate |

TABLE 1-continued

| Cmpd No. | Compound Structure and Name |
|---|---|
| 29 | 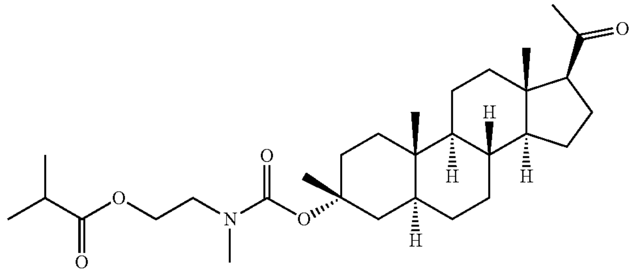 2-(((((3R,5S,8R,9S,10S,13S,14S,17S)-17-acetyl-3,10,13-trimethylhexadecahydro-1H-cyclopenta[a]phenanthren-3-yl)oxy)carbonyl)(methyl)amino)ethyl isobutyrate |
| 30 | 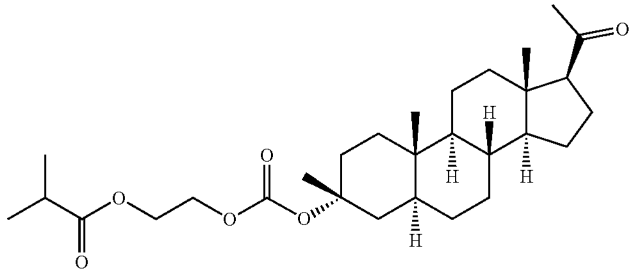 2-(((((3R,5S,8R,9S,10S,13S,14S,17S)-17-acetyl-3,10,13-trimethylhexadecahydro-1H-cyclopenta[a]phenanthren-3-yl)oxy)carbonyl)oxy)ethyl isobutyrate |
| 31 | 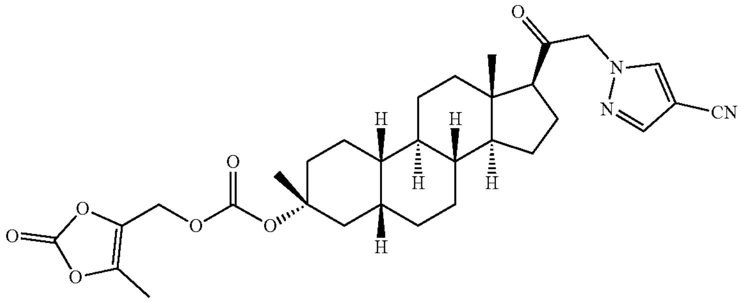 (3R,5R,8R,9R,10S,13S,14S,17S)-17-(2-(4-cyano-1H-pyrazol-1-yl)acetyl)-3,13-dimethylhexadecahydro-1H-cyclopenta[a]phenanthren-3-yl ((5-methyl-2-oxo-1,3-dioxol-4-yl)methyl) carbonate |
| 32 | 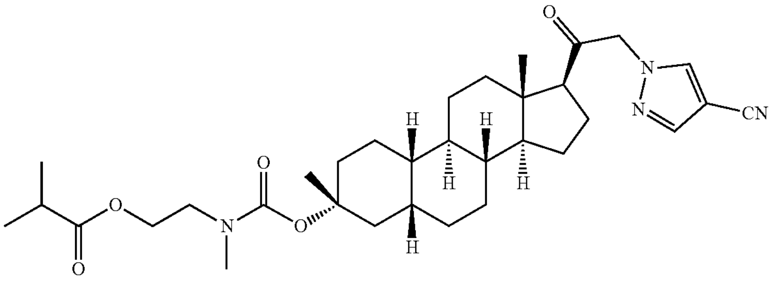 2-(((((3R,5R,8R,9R,10S,13S,14S,17S)-17-(2-(4-cyano-1H-pyrazol-1-yl)acetyl)-3,13-dimethylhexadecahydro-1H-cyclopenta[a]phenanthren-3-yl)oxy)carbonyl)(methyl)amino)ethyl isobutyrate |

TABLE 1-continued

| Cmpd No. | Compound Structure and Name |
| --- | --- |
| 33 | 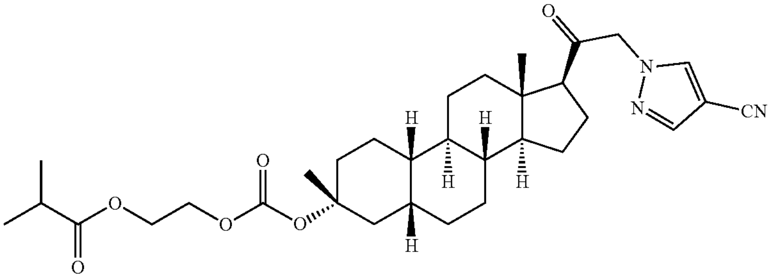 2-(((((3R,5R,8R,9R,10S,13S,14S,17S)-17-(2-(4-cyano-1H-pyrazol-1-yl)acetyl)-3,13-dimethylhexadecahydro-1H-cyclopenta[a]phenanthren-3-yl)oxy)carbonyl)oxy)ethyl isobutyrate |

Compounds provided herein are described with reference to both generic formulae and specific compounds. In addition, compounds of the present disclosure may exist in a number of different forms or derivatives, all within the scope of the present disclosure. These include, for example, tautomers, stereoisomers, racemic mixtures, regioisomers, salts, prodrugs, solvated forms, different crystal forms or polymorphs, and active metabolites.

The compounds of present disclosure can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the present disclosure are enantiopure compounds. In certain embodiments, mixtures of enantiomers or diastereomers are provided.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Furthermore, certain compounds, as described herein may have one or more double bonds that can exist as either the Z or E isomer, unless otherwise indicated. The present disclosure additionally encompasses the compounds as individual isomers substantially free of other isomers and alternatively, as mixtures of various isomers, e.g., racemic mixtures of enantiomers. In addition to the above-mentioned compounds per se, this disclosure also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched".

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, IN 1972).

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system (for example, 1H- and 3H-imidazole, 1H-, 2H- and 4H-1,2,4-triazole, 1H- and 2H-isoindole, and 1H- and 2H-pyrazole). Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

Compounds of the present disclosure can be formulated as or be in the form of pharmaceutically acceptable salts. Unless specified to the contrary, a compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, $19^{th}$ ed., Mack Publishing Co., Easton, PA, Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. Examples of solvents that form solvates include, but are not limited to, water, isopropanol, ethanol, methanol, DMSO, ethyl acetate, acetic acid, and ethanolamine.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the compounds of present disclosure are meant to also include their isotopes, such as but not limited to $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{18}F$, $^{19}F$, $^{35}Cl$, $^{37}Cl$, $^{79}Br$, $^{81}Br$, $^{124}I$, $^{127}I$ and $^{131}I$. In some embodiments, hydrogen includes protium, deuterium and tritium. In some embodiments, carbon includes $^{12}C$ and $^{13}C$.

Synthesis of Compounds of the Disclosure

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^{1}H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6 (6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). 1H-NMR spectra is recorded in $CDCl_3$, $CD_3OD$ or DMSO-$d_6$ solutions (reported in ppm) on a Varian or Bruker instrument (400 MHz).

MS measurement is carried out using Shimadzu 2010 Mass Spectrometer or Agilent 6110A MSD or 1969A TOF mass spectrometer using electrospray, chemical and electron impact ionization methods from a range of instruments.

The known starting materials of the present disclosure can be synthesized by using or according to the known methods in the art, or can be purchased from commercial suppliers such as Aldrich Chemical Company, Adamas-beta, TCI or Accela ChemBio Co., Ltd, and were used without further purification unless otherwise indicated. Tetrahydrofuran (THF), N,N-dimethylformamide (DMF), dichloromethane (DCM), dichloroethane (DCE), dioxane and 1,1,2,2-tetrachloroethane were purchased from Aldrich in Sure seal bottles and used as received.

Unless otherwise specified, the reactions of the present disclosure were all done in anhydrous solvents, and the reaction flasks were typically fitted with rubber septa for the introduction of substrates and reagents via syringe. Glassware was oven dried and/or heat dried.

For illustrative purposes, the following shows general synthetic route for preparing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In some embodiments, compounds of Formula (I) provided herein are prepared by the reaction of brexanolone with a compound of Formula (II):

(II)

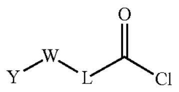

wherein L, W and Y are defined as supra.

Scheme 1 illustrates an exemplary synthesis of compounds of Formula (I) starting from the reaction of brexanolone with a compound of Formula (II).

Scheme 1

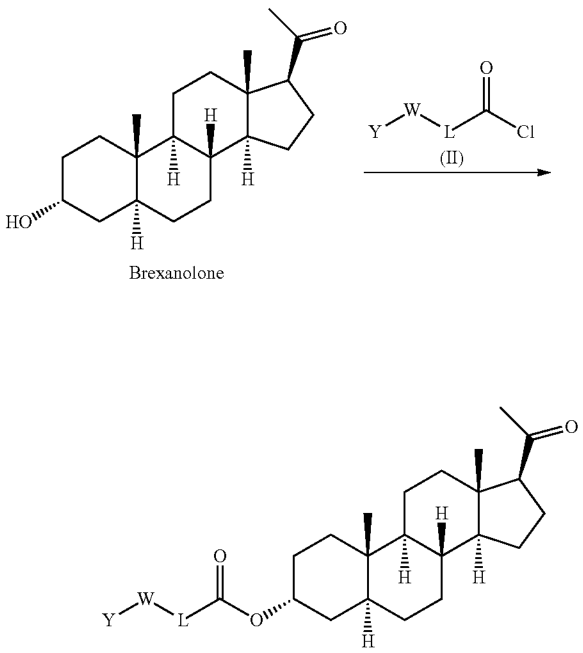

In some embodiments, compounds of Formula (I) provided herein are prepared according to Scheme 2.

Scheme 2

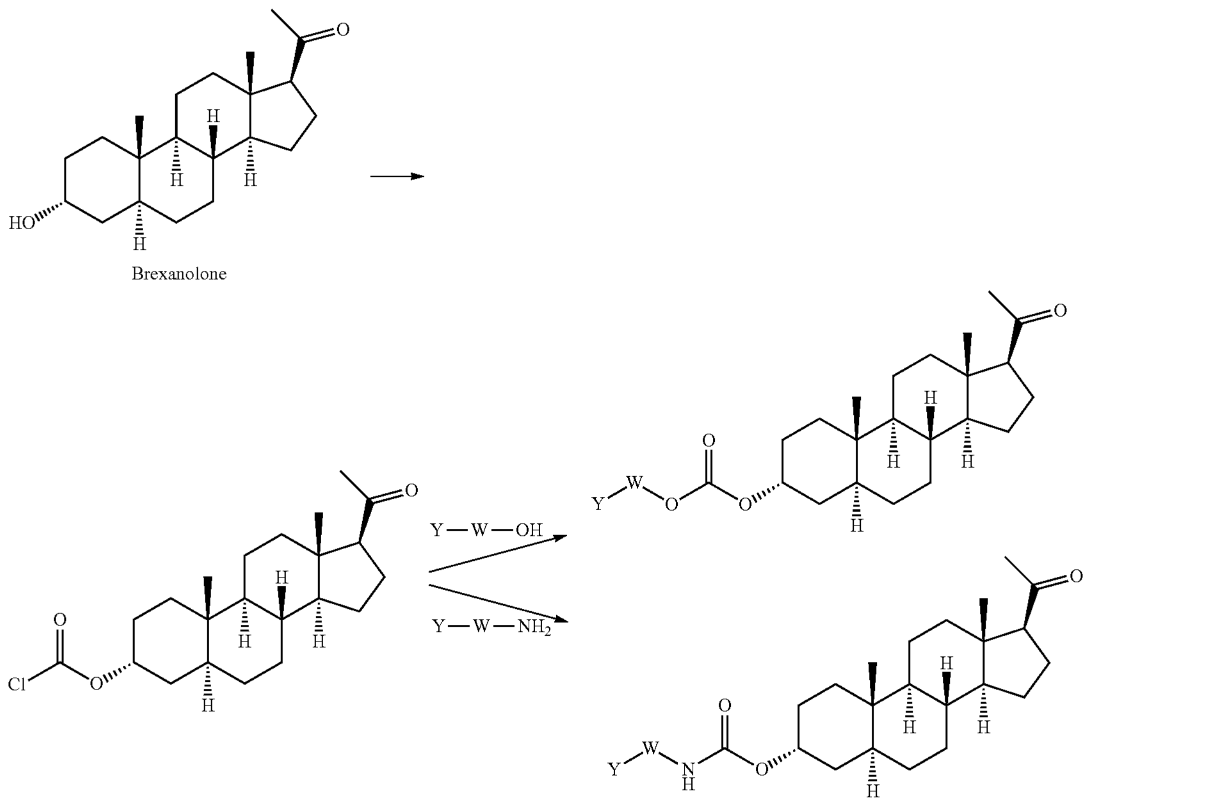

Brexanolone

As would be appreciated by one of skill in the art, the compounds of the present disclosure can be synthesized by routes other than those explicitly disclosed herein.

Properties of Compounds of the Present Disclosure

In one aspect, the present disclosure provides compounds of Formula (I), Formula (Ia), Formula (Ib), Formula (Ic-1), Formula (Ic-2), Formula (Id-1), Formula (Id-2) or pharmaceutically acceptable salts thereof, which act as modulating agents for $GABA_A$ receptors.

In some embodiments, the compounds of the present disclosure are prodrug compounds, that upon administration to a subject, undergo chemical conversion by one or more metabolic processes to release an active pharmacological agent in vivo.

Thus, in some embodiments, the compounds of the present disclosure are converted to brexanolone, ganaxolone or zuranolone after administration. In some embodiments, the compounds of the present disclosure are converted to brexanolone, ganaxolone or zuranolone after oral administration. In some embodiments, the compounds of the present disclosure are converted to brexanolone, ganaxolone or zuranolone after parenteral administration. In some embodiments, the compounds of the present disclosure are converted to brexanolone, ganaxolone or zuranolone in blood. In some embodiments, the release rate of brexanolone, ganaxolone or zuranolone is not less than 90%, 80%, 70%, 60%, 50%, 40%, 30%, 20% or 10% within 1 hour after contact of the compounds of the present disclosure with blood. In some embodiments, the release rate of brexanolone, ganaxolone or zuranolone is not less than 90%, 80%, 70%, 60%, 50%, 40%, 30%, 20% or 10% within 2 hours after contact of the compounds of the present disclosure with blood.

In some embodiments, the compounds of the present disclosure show a thermodynamic aqueous solubility (at pH 7.4) of at least 0.1 μM, at least 0.5 μM, at least 1 μM, at least 1.5 μM, at least 2 μM, at least 2.5 μM, at least 3 μM, at least 3.5 μM, at least 4 μM, at least 4.5 μM, at least 5 μM, at least 5.5 μM, at least 6 μM, at least 6.5 μM, at least 7 μM, at least 8 μM, at least 9 μM, at least 10 μM, at least 15 μM, at least 20 μM or even greater. In some embodiments, the compounds of the present disclosure show a thermodynamic aqueous solubility (at pH 7.4) in a range of 0.1-20 μM, for example, 0.1-18 μM, 0.1-16 UM, 0.1-14 μM, 0.1-12 μM, 0.1-10 UM, 0.1-9 μM, 0.1-8 μM, 0.1-7 μM, 0.1-6 μM, 0.1-5 μM, 0.1-4 μM, 0.1-3 μM, 0.1-2 μM, 1-20 μM, 2-20 μM, 2-15 μM, 2-10 μM, 2-9 UM, 2-8 μM, 2-7 μM, 2-6μ, 2-5μ, 2-4μ, and the like.

In some embodiments, the compounds of the present disclosure have a lipophilicity as measured by Log D in a range of 0.5-7, for example, 1-7, 1.5-7, 2-7, 2.5-7, 3-7, 4-7, 1.5-6, 2-6, 2.5-6, 3-6, 3.5-6, 4-6, 1-5, 1.5-5, 2-5, 2.5-5, 3-5, 3.5-5, 4-5, 4.5-5, and the like.

In some embodiments, the compounds of the present disclosure show a half-life ($t_{1/2}$) in plasma of not less than 10 minutes, not less than 20 minutes, not less than 30 minutes, not less than 40 minutes, not less than 50 minutes, not less than 60 minutes, not less than 70 minutes, not less than 80 minutes, not less than 90 minutes, not less than 100 minutes, not less than 110 minutes, not less than 120 minutes, not less than 130 minutes, not less than 140 minutes, not less than 150 minutes, not less than 160 minutes, not less than 170 minutes, not less than 180 minutes, not less than 190 minutes, or not less than 200 minutes, as measured in the assay described in examples below.

In some embodiments, the compounds of the present disclosure show a half-life in liver S9 of not less than 10 minutes, not less than 20 minutes, not less than 30 minutes, not less than 40 minutes, or not less than 50 minutes, as measured in the assay described in examples below.

Therefore, the compounds of Formula (I), Formula (Ia), Formula (Ib), Formula (Ic-1), Formula (Ic-2), Formula (Id-1), Formula (Id-2), and pharmaceutically acceptable salts thereof, act as the prodrugs of NASs, in particular, by releasing brexanolone, ganaxolone or zuranolone, to modulate $GABA_A$ receptor function, and thus GABA function.

As used herein, the term “modulate” or “modulation” refers to the inhibition or potentiation of $GABA_A$ receptor function. A “modulator” may be, for example, an agonist, partial agonist, antagonist, or partial antagonist of the $GABA_A$ receptor.

Pharmaceutical Compositions

The present disclosure provides pharmaceutical compositions comprising one or more compounds of Formula (I), Formula (Ia), Formula (Ib), Formula (Ic-1), Formula (Ic-2), Formula (Id-1), Formula (Id-2), or a pharmaceutically acceptable salt thereof. In some embodiments, the pharmaceutical compositions of the present disclosure comprise a compound selected from Formula (I), Formula (Ia), Formula (Ib), Formula (Ic-1), Formula (Ic-2), Formula (Id-1), Formula (Id-2), or a pharmaceutically acceptable salt thereof. In some embodiments, the pharmaceutical compositions of the present disclosure comprise a first compound selected from Formula (I), Formula (Ia), Formula (Ib), Formula (Ic-1), Formula (Ic-2), Formula (Id-1), Formula (Id-2) or a pharmaceutically acceptable salt thereof and one or more additional compounds of the same formula, wherein said first compound and additional compound(s) are not the same molecules.

In some embodiments, the pharmaceutical composition comprises one or more compounds of the present disclosure, or a pharmaceutically acceptable salt thereof, and at least one pharmaceutical acceptable carrier or excipient.

A “pharmaceutical composition”, as used herein, is a formulation containing the compounds of the present disclosure in a form suitable for administration to a subject. In some embodiments, the pharmaceutical composition is in bulk or in unit dosage form.

As used herein, the term “unit dosage form” refers to physically discrete units suitable as unitary dosages for subjects, each unit containing a predetermined quantity of active material calculated to produce the desired therapeutic effect, in association with a suitable pharmaceutical excipient. The unit dosage form is any of a variety of forms, including, for example, tablets, capsules, pills, powders, granules, sachets, cachets, lozenges, suspensions, emulsions, solutions, syrups, aerosols (as a solid or in a liquid medium), spray, ointment, paste, cream, lotion, gel, patch, inhalant, or suppository. The quantity of active ingredient (e.g., a formulation of the disclosed compound or salt, hydrate, solvate or isomer thereof) in a unit dose of composition is a therapeutically effective amount and is varied according to the particular treatment involved. One skilled in the art will appreciate that it is sometimes necessary to make routine variations to the dosage depending on the age and condition of the patient. The dosage will also depend on the route of administration.

The pharmaceutical compositions of the present disclosure can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration (e.g., a nasal spray).

In some embodiments, the compound of the present disclosure is mixed under sterile conditions with a pharmaceutically acceptable excipient, and with any preservatives, buffers or propellants that are required.

As used herein, the term “pharmaceutically acceptable excipient” includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be includes. These and other such compounds are described in the literature, e.g., in the Merck Index, Merck & Company, Rahway, NJ. A “pharmaceutically acceptable excipient” as used in the specification and claims includes both one and more than one such excipient. The term “pharmaceutically acceptable excipient” also encompasses “pharmaceutically acceptable carrier” and “pharmaceutically acceptable diluent”.

The particular excipient, carrier, or diluent will depend upon the means and purpose for which the compounds of the present disclosure is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable excipients, diluents, and carriers, and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, dextrins, starch, hydroxyethyl starch; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The composition may also comprise one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences $16^{th}$ edition, Osol, A. Ed. (1980). A "liposome" is a small vesicle composed of various types of lipids, phospholipids and/or surfactant which is useful for delivery of a drug (such as the compounds disclosed herein and, optionally, a chemotherapeutic agent) to a mammal. The components of the liposome are commonly arranged in a bilayer formation, similar to the lipid arrangement of biological membranes.

The pharmaceutical compositions of compounds of the present disclosure can be formulated depending on the particular route of administration and dosage form. The pharmaceutical compositions are generally formulated to achieve a physiologically compatible pH, for example, a pH of about 3 to about 11, about 3 to about 10, about 3 to about 9, about 3 to about 8, about 3 to about 7, about 4 to about 11, about 4 to about 10, about 4 to about 9, about 4 to about 8, about 4 to about 7, about 5 to about 11, about 5 to about 10, about 5 to about 9, about 5 to about 8, or about 5 to about 7. In some embodiments, the pharmaceutical compositions are formulated to achieve a pH of about 5 to about 7.

In some embodiments, the pharmaceutical compositions of the present disclosure may be formulated to provide therapeutically effective amount of the compounds provided herein.

As used herein, the term "therapeutically effective amount" refers to an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent. The precise effective amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

In some embodiments, the pharmaceutical compositions of the present disclosure may be formulated for parenteral or oral administration. For example, the pharmaceutical compositions of the present disclosure may be formulated as solids, liquid solutions, emulsions or suspensions. In some embodiments, the pharmaceutical compositions of the present disclosure may be formulated for pulmonary administration. For example, the pharmaceutical compositions of the present disclosure may be formulated as liquids or powders. In some embodiments, the pharmaceutical compositions of the present disclosure may be formulated as a lyophilized solid that is reconstituted with a physiologically compatible solvent prior to administration. In some embodiments, the pharmaceutical compositions of the present disclosure may be formulated in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder).

In some embodiments, the pharmaceutical compositions of the present disclosure can also be administered chronically ("chronic administration"). As used herein, the term "chronic administration" refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

In some embodiments, the pharmaceutical compositions of the present disclosure can also be administered in sustained release forms or from sustained release drug delivery systems. A description of representative sustained release materials can be found in Remington's Pharmaceutical Sciences.

In some embodiments, the pharmaceutical compositions of the present disclosure can be formulated as a long-acting formulation for administration by injection, comprising a therapeutically effective amount of the compound(s) provided herein and a pharmaceutically acceptable excipient, wherein the pharmaceutically acceptable excipient is water and the compound(s) is suspended therein. In some embodiments, the long-acting formulation is administrated by intramuscular injection. In some embodiments, the long-acting formulation is administrated by subcutaneous injection. In some embodiments, the pharmaceutical compositions formulated as a long-acting formulation can further comprise one or more additional agents selected from the group consisting of a wetting agent, a suspending agent, a preservative, a buffer, and an isotonizing agent.

The pharmaceutical composition (or formulation) for application may be packaged in a variety of ways depending on the method used for administering the drug. For example, an article for distribution can include a container having deposited therein the pharmaceutical composition in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The compositions may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

In some embodiments, the pharmaceutical compositions of the present disclosure are formulated in unit dosage form. Such single or unit dosage form are contemplated to be administered once, twice, three times, four times or more per day. In certain embodiments, the pharmaceutical compositions of the present disclosure can be formulated to provide a unit dose of 0.01-50 mg/kg, 0.05-50 mg/kg, 0.1-50 mg/kg, 0.5-50 mg/kg, 1-50 mg/kg, 2-50 mg/kg, 3-50 mg/kg, 4-50 mg/kg, 5-50 mg/kg, 0.01-40 mg/kg, 0.05-40 mg/kg, 0.1-40 mg/kg, 0.5-40 mg/kg, 1-40 mg/kg, 2-40 mg/kg, 3-40 mg/kg, 4-40 mg/kg, 5-40 mg/kg, 0.01-30 mg/kg, 0.05-30 mg/kg, 0.1-30 mg/kg, 0.5-30 mg/kg, 1-30 mg/kg, 2-30 mg/kg, 3-30 mg/kg, 4-30 mg/kg, 5-30 mg/kg, 0.01-20 mg/kg, 0.05-20 mg/kg, 0.1-20 mg/kg, 0.5-20 mg/kg, 1-20 mg/kg, 2-20 mg/kg, 3-20 mg/kg, 4-20 mg/kg, 5-20 mg/kg, 0.01-15 mg/kg, 0.05-15 mg/kg, 0.1-15 mg/kg, 0.5-15 mg/kg, 1-15 mg/kg, 2-15 mg/kg, 3-15 mg/kg, 4-15 mg/kg, 5-15 mg/kg, 0.01-10 mg/kg, 0.05-10 mg/kg, 0.1-10 mg/kg, 0.5-10 mg/kg, 1-10 mg/kg, 2-10 mg/kg, 3-10 mg/kg, 4-10 mg/kg, or 5-10 mg/kg, of the compounds of the present disclosure, or a pharmaceutically acceptable salt thereof. In some embodiments, the unit dose is administered once a day. In other embodiments, the unit dose is administered twice a day. In further embodiments, the unit dose is administered three times a day. In further embodiments, the unit dose is administered four times a day.

In some embodiments, the pharmaceutical compositions of the present disclosure is administrated to achieve an effective amount of compounds of the present disclosure. For example, the amount of the compounds of the present disclosure may range from about 0.1-1000 mg, about 1-1000 mg, about 10-1000 mg, about 50-1000 mg, about 100-1000 mg, about 200-1000 mg, about 300-1000 mg, about 400-1000 mg, about 500-1000 mg, about 0.1-900 mg, about 0.1-800 mg, about 0.1-700 mg, about 0.1-600 mg, about 0.1-500 mg, about 1-500 mg, about 10-500 mg, about 50-500 mg, about 100-500 mg, about 200-500 mg, about 300-500 mg, or about 400-500 mg. In some embodiments, the pharmaceutical compositions of the present disclosure is administrated to achieve an amount of compounds of the present disclosure of about 200-500 mg.

In some embodiments, the compounds of the present disclosure can be administered as the sole active agent, or they can be administered in combination with one or more additional active ingredients. The skilled artisan will recognize that a variety of active ingredients may be combined with the compounds of the present disclosure. In some embodiments, the additional active ingredient of the pharmaceutical combination formulation or dosing regimen has complementary activities to the compounds of disclosure such that they do not adversely affect each other. Such ingredients are suitably present in combination in amounts that are effective for the purpose intended.

In some embodiments, the additional active ingredients can improve the bioavailability of the compounds provided herein, reduce and/or modify the metabolism of the compounds provided herein, inhibit the excretion of the compounds provided herein, and/or modify the distribution of the compounds provided herein within the body.

The additional therapeutically active agents include, for example, small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The compound(s) of Formula (I), Formula (Ia), Formula (Ib), Formula (Ic-1), Formula (Ic-2), Formula (Id-1), Formula (Id-2) or a pharmaceutically acceptable salt thereof and the additional active ingredient(s) may be administered together in a unitary pharmaceutical composition or separately and, when administered separately this may occur simultaneously or sequentially in any order. Such sequential administration may be close in time or remote in time. The amounts of the compound(s) of Formula (I), Formula (Ia), Formula (Ib), Formula (Ic-1), Formula (Ic-2), Formula (Id-1), Formula (Id-2) and the additional active ingredient(s) and the relative timings of administration will be selected in order to achieve the desired combined therapeutic effect.

Suitable dosages for any of the above co-administered agents are those presently used and may be lowered due to the combined action (synergy) of the newly identified agent and other chemotherapeutic agents or treatments.

As used herein, the term "combination" refers to simultaneous, separate or sequential administration. In some embodiments, "combination" refers to simultaneous administration. In some embodiments, "combination" refers to separate administration. In some embodiments, "combination" refers to sequential administration. Where the administration is sequential or separate, the delay in administering the second component should not be such as to lose the beneficial effect of the combination.

Accordingly, in a further aspect, there is provided a compound of Formula (I), Formula (Ia), Formula (Ib), Formula (Ic-1), Formula (Ic-2), Formula (Id-1), Formula (Id-2) or a pharmaceutically acceptable salt thereof in combination with one or more additional active ingredients.

In a further aspect, there is provided a pharmaceutical composition comprising a compound of Formula (I), Formula (Ia), Formula (Ib), Formula (Ic-1), Formula (Ic-2), Formula (Id-1), Formula (Id-2) or a pharmaceutically acceptable salt thereof in combination with one or more additional active ingredients, in association with a pharmaceutically acceptable excipient.

In a further aspect, there is provided a kit comprising a compound of Formula (I), Formula (Ia), Formula (Ib), Formula (Ic-1), Formula (Ic-2), Formula (Id-1), Formula (Id-2) or a pharmaceutically acceptable salt thereof in combination with one or more additional active ingredients.

In a further aspect, there is provided a kit comprising:

(a) a compound of formula Formula (I), Formula (Ia), Formula (Ib), Formula (Ic-1), Formula (Ic-2), Formula (Id-1), Formula (Id-2) or a pharmaceutically acceptable salt thereof in a first unit dosage form;

(b) an additional active ingredient selected from those listed above in a second unit dosage form; and (c) container for containing the first and second unit dosage forms.

Methods of Treatment

In one aspect, there is provided a method of treating diseases or conditions related to $GABA_A$ receptor function in a subject in need thereof, the method comprising administering to the subject a therapeutically effective amount of a compound of Formula (I), Formula (Ia), Formula (Ib), Formula (Ic-1), Formula (Ic-2), Formula (Id-1), Formula (Id-2) or a pharmaceutically acceptable salt thereof, owing to the modulatory activity of the compounds of the present disclosure for the $GABA_A$ receptor.

In another aspect, there is provided a method of treating diseases or conditions related to $GABA_A$ receptor function in a subject in need thereof, the method comprising administering to the subject a composition comprising a therapeutically effective amount of a compound of Formula (I), Formula (Ia), Formula (Ib), Formula (Ic-1), Formula (Ic-2), Formula (Id-1), Formula (Id-2), or a pharmaceutically acceptable salt thereof, and one or more pharmaceutically acceptable excipients.

In one aspect, there is provided a method of treating a neurological disease or condition in a subject in need thereof, the method comprising administering to the subject a therapeutically effective amount of a compound of Formula (I), Formula (Ia), Formula (Ib), Formula (Ic-1), Formula (Ic-2), Formula (Id-1), Formula (Id-2), pharmaceutically acceptable salt thereof, or pharmaceutical composition thereof.

As used herein, the term "subject in need thereof" is a subject having diseases or conditions related to $GABA_A$ receptor function. A "subject" includes a warm-blooded animal. In some embodiments, the warm-blooded animal is a mammal. In some embodiments, the warm-blooded animal is a human.

Exemplary diseases or conditions related to $GABA_A$ receptor function include, but are not limited to, sleep disorders (for example, insomnia), mood disorders (for example, depression (e.g., postpartum depression (PPD), major depressive disorder (MDD)), dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))), schizophrenia spectrum disorders (for example, schizophrenia, schizoaffective disorder), convulsive disorders (for example, epilepsy (e.g., status epilepticus (SE)), seizures), disorders of memory and/or cognition (for example, attention disorders (e.g., attention deficit hyperactivity disorder (ADHD)), dementia (e.g., Alzheimer's type dementia, Lewis body type dementia, vascular type dementia), movement disorders (for example, Huntington's disease, Parkinson's disease), personality disorders (for example, anti-social personality disorder, obsessive compulsive personality disorder), autism spectrum disorders (ASD) (for example, autism, monogenetic causes of autism such as synaptophathy's, e.g., Rett syndrome, Fragile X syndrome, Angelman syndrome), pain (for example, neuropathic pain, injury related pain syndromes, acute pain, chronic pain), traumatic brain injury (TBI), vascular diseases (for example, stroke, ischemia, vascular malformations), substance abuse disorders and/or withdrawal syndromes (for example, addition to opiates, cocaine, and/or alcohol), tinnitus, and essential tremor (ET).

In some embodiments of the present method, the disease is anxiety, massive depression disorder, postpartum disorder, Alzheimer disease, Parkinson disease, epilepsy, focal onset seizures, PCDH19 pediatric epilepsy, pediatric genetic epilepsies, CDKL5 Deficiency Disorder (CDD), catamenial epilepsy, infantile spasms, Fragile X syndrome, depression, postpartum depression or premenstrual syndrome. In some embodiments, the disease is CDD, MDD, PPD, essential tremor, PTSD, SE, ESE, Fragile X syndrome, Parkinson's Disease, or treatment resistant depression.

In one aspect, the compounds of Formula (I), Formula (Ia), Formula (Ib), Formula (Ic-1), Formula (Ic-2), Formula (Id-1), Formula (Id-2) and pharmaceutically acceptable salts thereof find use in therapy, for example in the treatment of diseases or conditions related to $GABA_A$ receptor function. In some embodiments, the therapy is for use in mammals, including humans and non-human mammals.

As used herein, the term "therapy" is intended to have its normal meaning of dealing with a disease in order to entirely or partially relieve one or more of its symptoms, or to correct or compensate for the underlying pathology, thereby achieving beneficial or desired clinical results. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Therapy" can also mean prolonging survival as compared to expected survival if the absence of treatment. Those in need of therapy include those already with the condition or disorder as well as those prone to have the condition or disorder or those in which the condition or disorder is to be prevented. The term "therapy" also encompasses prophylaxis unless there are specific indications to the contrary. The terms "therapeutic" and "therapeutically" should be interpreted in a corresponding manner.

As used herein, the term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

Therefore, in one aspect, there is provided a compound of Formula (I), Formula (Ia), Formula (Ib), Formula (Ic-1), Formula (Ic-2), Formula (Id-1), Formula (Id-2) or a pharmaceutically acceptable salt thereof, for use in therapy.

In some embodiments, there is provided a compound of Formula (I), Formula (Ia), Formula (Ib), Formula (Ic-1), Formula (Ic-2), Formula (Id-1), Formula (Id-2) or a pharmaceutically acceptable salt thereof, for use as a medicament.

In some embodiments, there is provided a compound of Formula (I), Formula (Ia), Formula (Ib), Formula (Ic-1), Formula (Ic-2), Formula (Id-1), Formula (Id-2) or a pharmaceutically acceptable salt thereof, for use in the treatment of diseases or conditions associated alone or in part with GABA function.

In some embodiments, there is provided a compound of Formula (I), Formula (Ia), Formula (Ib), Formula (Ic-1), Formula (Ic-2), Formula (Id-1), Formula (Id-2) or a pharmaceutically acceptable salt thereof, for use in the manufacture of a medicament for the treatment of diseases or conditions related to $GABA_A$ receptor function.

In some embodiments, there is provided a compound of Formula (I), Formula (Ia), Formula (Ib), Formula (Ic-1), Formula (Ic-2), Formula (Id-1), Formula (Id-2) or a pharmaceutically acceptable salt thereof, for use in the manufacture of a medicament for the treatment of depression, such as PPD and MDD, Alzheimer's type dementia and Parkinson's disease.

The compounds of the present disclosure for use in treating diseases or conditions related to $GABA_A$ receptor function described herein may be used as a monotherapy. As used herein, the term "monotherapy" refers to the administration of a single active or therapeutic compound to a subject in need thereof. In some embodiments, monotherapy will involve administration of a therapeutically effective amount of one or more of the compounds of the present disclosure, or a pharmaceutically acceptable salt thereof, to a subject in need of such treatment.

Depending upon the particular diseases or conditions to be treated, the method of treating diseases or conditions related to $GABA_A$ receptor function described in this specification may involve, in addition to administration of the compounds of the present disclosure, one or more additional therapies, for example, conventional surgery, radiotherapy, chemotherapy, or a combination of such additional therapies. As used herein, the term "combination therapy" refers to the administration of a combination of multiple active compounds.

The additional therapies may be administered separately from the compounds of the present disclosure, as part of a multiple dosage regimen. Alternatively, these additional therapies may be part of a single dosage form, mixed with the compounds of the present disclosure in a single composition.

In some embodiments, the compounds of the present disclosure may be administered simultaneously, sequentially or separately to treatment with the conventional surgery, radiotherapy or chemotherapy.

EXAMPLES

For the purpose of illustration, the following examples are included. However, it is to be understood that these examples do not limit the invention and are only meant to suggest a method of practicing the present disclosure. Persons skilled in the art will recognize that the chemical reactions described may be readily adapted to prepare a number of other compounds of the present disclosure, and alternative methods for preparing the compounds of the present disclosure are deemed to be within the scope of the present disclosure. For example, the synthesis of non-exemplified compounds according to the present disclosure may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the present disclosure.

Example 1

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] hexanoate

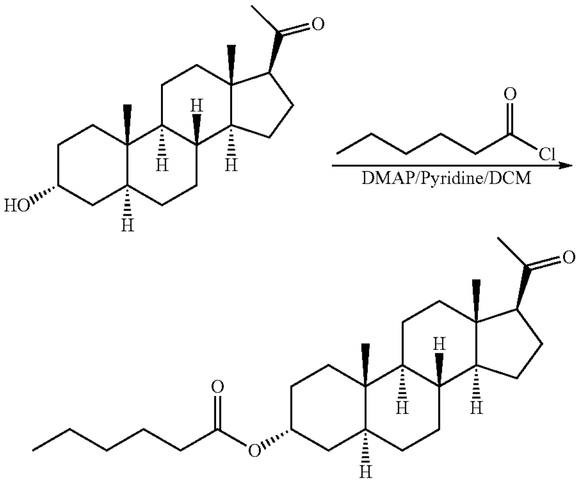

To a mixture of 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone (500 mg, 1.57 mmol, 1.0 eq) was dissolved in DCM (10 mL). Hexanoyl chloride (275 mg, 2.04 mmol, 0.285 mL, 1.3 eq), pyridine (248 mg, 3.14 mmol, 0.253 mL, 2.0 eq) and DMAP (9.6 mg, 0.079 mmol, 0.05 eq) were added. The reaction mixture was stirred at 20° C. for 12 h. The reaction mixture was diluted with $H_2O$ (30 ml) and extracted with DCM (30 mL×3). The combined organic layers were washed by brine (50 mL), dried over $Na_2SO_4$, filtered and concentrated. The resulting residue was purified by flash silica gel chromatography (ISCO®; 20 g SepaFlash® Silica Flash Column, eluted with 0-10% ethyl acetate/petroleum ether gradient @35 mL/min) to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]hexanoate (550 mg, 84.1% yield) as a white solid. LCMS (ESI) m/z calcd for $C_{27}H_{44}O_3$ 416.33, found 415.4 (M−H). $^1$H NMR (400 MHz, $CDCl_3$) δ (ppm) 5.01 (s, 1H), 2.54-2.49 (m, 1H), 2.31-2.26 (m, 2H), 2.19-2.10 (m, 4H), 2.01-1.98 (m, 1H), 1.73-1.59 (m, 8H), 1.52-1.11 (m, 16H), 0.99-0.88 (m, 4H), 0.83-0.72 (m, 4H), 0.60 (s, 3H). $^{13}$C NMR (100 MHz, $CDCl_3$) δ (ppm) 209.64, 173.32, 69.63, 63.80, 56.71, 54.09, 44.21, 40.05, 39.03, 35.77, 35.39, 34.78, 32.91, 32.84, 31.86, 31.51, 31.28, 28.23, 26.08, 24.82, 24.33, 22.72, 22.35, 20.76, 13.96, 13.43, 11.31.

Example 2

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]heptanoate

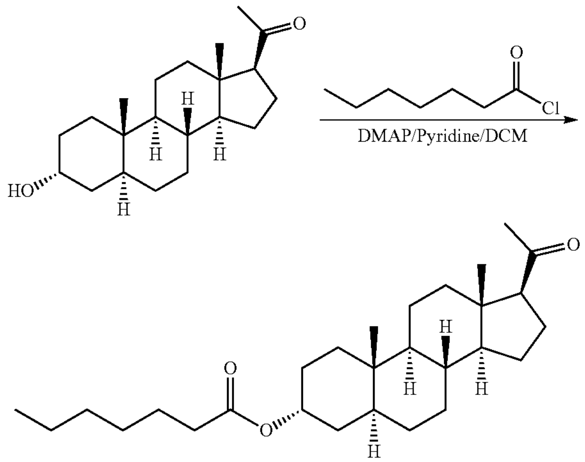

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]heptanoate was prepared following the same procedure as Example 1, except changing hexanoyl chloride to heptanoyl chloride (550 mg, 80.5% yield). LCMS (ESI) m/z calcd for $C_{28}H_{46}O_3$ 430.34, found 429.3 (M−H). $^1$H NMR (400 MHz, $CDCl_3$) δ (ppm) 5.02 (s, 1H), 2.54-2.50 (m, 1H), 2.32-2.28 (m, 2H), 2.17-2.11 (m, 4H), 2.02-2.00 (m, 1H), 1.71-1.61 (m, 8H), 1.48-1.15 (m, 18H), 0.93-0.89 (m, 4H), 0.83-0.76 (m, 4H), 0.61 (s, 3H). $^{13}$C NMR (101 MHz, $CDCl_3$) δ (ppm) 209.69, 173.38, 69.69, 63.86, 56.78, 54.16, 44.26, 40.11, 39.09, 35.82, 35.45, 34.87, 32.97, 32.90, 31.91, 31.54, 28.85, 28.28, 26.13, 25.16, 24.38, 22.79, 22.57, 20.81, 14.09, 13.47, 11.35.

Example 3

(3R,5S,8R,9S,10S,13S,14S,17S)-17-acetyl-10,13-dimethylhexadecahydro-1H-cyclopenta[a]phenanthren-3-yl ocatanoate

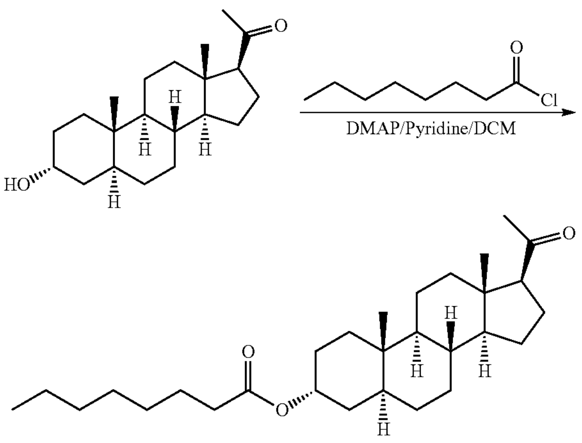

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]octanoate was prepared following the same procedure as Example 1, except changing hexanoyl chloride to octanoyl chloride (550 mg, 78.0% yield). LCMS (ESI) m/z calcd for $C_{29}H_{48}O_3$ 444.36, found 443.4 (M−H). $^1$H NMR (400 MHz, $CDCl_3$) δ (ppm) 5.02 (s, 1H), 2.54-2.49 (m, 1H), 2.32-2.19 (m, 2H), 2.17-2.11 (m, 4H), 2.02-1.99 (m, 1H), 1.71-1.57 (m, 8H), 1.52-1.15 (m, 20H), 0.93-0.87 (m, 4H), 0.81-0.76 (m, 4H), 0.60 (s, 3H). $^{13}$C NMR (100 MHz, $CDCl_3$) δ (ppm) 173.37, 69.69, 63.86, 56.78, 54.17, 44.25, 40.11, 39.08, 35.82, 35.44, 34.86, 32.98, 32.90, 31.90, 31.77, 29.13, 31.54, 29.03, 28.28, 26.13, 25.20, 24.37, 22.79, 22.66, 20.81, 14.12, 13.46, 11.35.

Example 4

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]hexanoate

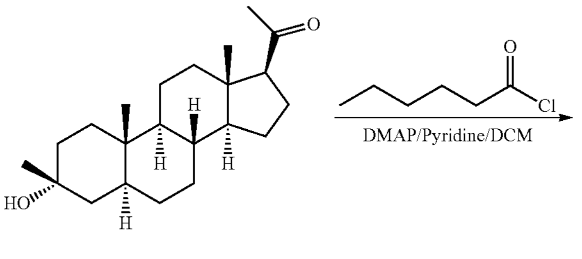

-continued

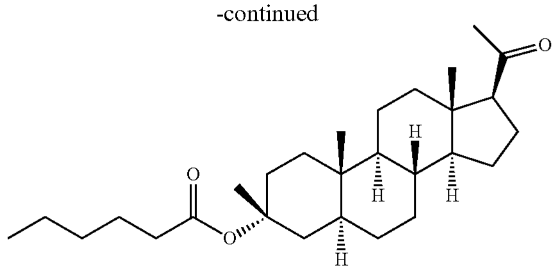

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]hexanoate was prepared following the same procedure as Example 1, except changing 1-[(3R,5S,8R,9S,10S,13S,14S,17S)-3-hydroxy-10,13-dimethyl- 2,3,4,5,6,7,8,9,11,12,14,15,16,17-tetradecahydro-1H-cyclopenta[a]phenanthren-17-yl]ethanone to 1-[(3R,5S,8R,9S,10S,13S,14S,17S)-3-hydroxy-3,10,13-trimethyl-2,3,4,5,6,7,8,9,11,12,14,15,16,17-tetradecahydro-1H-cyclopenta[a]phenanthren-17-yl]ethenone (176 mg, 44.8% yield). $^1$H NMR (400 MHz, $CDCl_3$) δ (ppm) 2.54-2.50 (m, 1H), 2.27-2.18 (m, 4H), 2.11 (s, 3H), 2.02-1.98 (m, 1H), 1.93-1.89 (m, 1H), 1.70-1.57 (m, 6H), 1.51-1.44 (m, 4H), 1.41-1.11 (m, 15H), 0.95-0.88 (m, 4H), 0.77 (s, 3H), 0.75-0.69 (m, 1H), 0.60 (s, 3H). $^{13}$C NMR (100 MHz, $CDCl_3$) δ (ppm) 209.72, 173.27, 81.63, 63.86, 56.76, 54.28, 44.29, 41.09, 39.10, 39.08, 35.76, 35.49, 35.33, 34.12, 32.26, 31.98, 31.54, 31.40, 28.01, 26.39, 25.00, 24.38, 22.79, 22.44, 21.01, 14.03, 13.48, 11.70.

Example 5

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]heptanoate

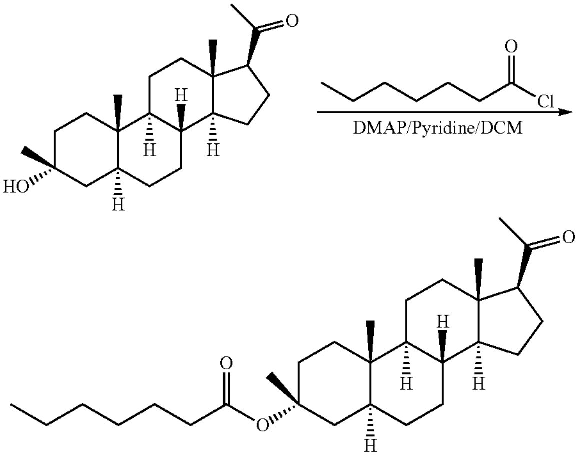

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]heptanoate was prepared following the same procedure as Example 1, except replacing 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone with 1-[(3R,5S,8R,9S,10S,13S,14S,17S)-3-hydroxy-3,10,13-trimethyl- 2,3,4,5,6,7,8,9,11,12,14,15,16,17-tetradecahydro-1H-cyclopenta[a]phenanthren-17-yl]ethenone, and changing hexanoyl chloride to heptanoyl chloride (350 mg, 51.8% yield). LCMS (ESI) m/z calcd for $C_{29}H_{48}O_3$ 444.36, found 443.4 (M−H). $^{1}$H NMR (400 MHz, $CDCl_3$) δ (ppm) 2.54-2.50 (m, 1H), 2.28-2.19 (m, 4H), 2.12 (s, 3H), 2.02-1.99 (m, 1H), 1.93-1.90 (m, 1H), 1.71-1.57 (m, 7H), 1.51-1.46 (m, 4H), 1.43-1.32 (m, 10H), 1.27-1.32 (m, 6H), 0.95-0.86 (m, 4H), 0.77 (s, 3H), 0.74-0.70 (m, 1H), 0.61 (s, 3H). $^{13}$C NMR (100 MHz, $CDCl_3$) δ (ppm) 209.21, 172.76, 81.11, 63.36, 56.25, 53.78, 43.77, 40.59, 38.59, 38.57, 35.30, 34.97, 34.80, 33.61, 31.73, 31.46, 31.09, 31.03, 28.40, 27.49, 25.87, 24.78, 23.86, 22.27, 22.09, 20.50, 13.61, 12.96, 11.19.

Example 6

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]octanoate

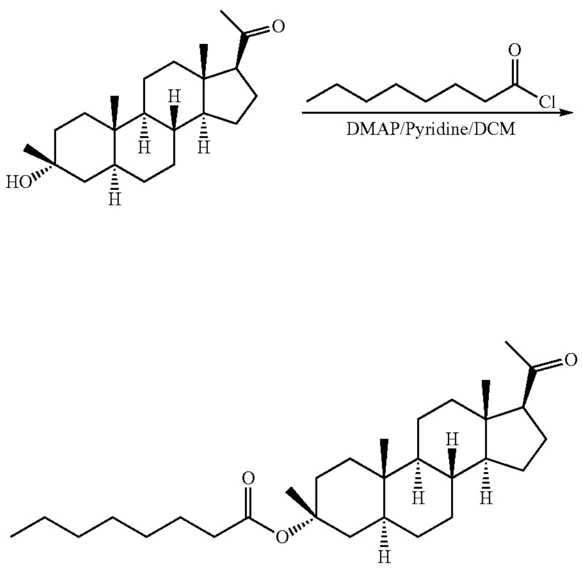

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl] octanoate was prepared following the same procedure as Example 1, except changing hexanoyl chloride to octanoyl chloride and replacing 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone with 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl] ethenone (350 mg, 50.2% yield). $^{1}$H NMR (400 MHz, $CDCl_3$) § (ppm) 2.54-2.50 (m, 1H), 2.27-2.17 (m, 7H), 2.02-1.94 (m, 1H), 1.93-1.90 (m, 1H), 1.71-1.15 (m, 29H), 0.95-0.85 (m, 4H), 0.77-0.70 (m, 4H), 0.61 (s, 3H). $^{13}$C NMR (100 MHz, $CDCl_3$) δ (ppm) 209.74, 173.29, 81.65, 63.89, 56.78, 54.32, 44.29, 41.11, 39.09, 35.83, 35.49, 35.33, 34.13, 32.29, 31.98, 31.83, 31.56, 29.23, 29.14, 28.01, 26.40, 25.36, 24.38, 22.79, 22.72, 21.03, 14.15, 13.48, 11.72.

Example 7

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylpropanoate

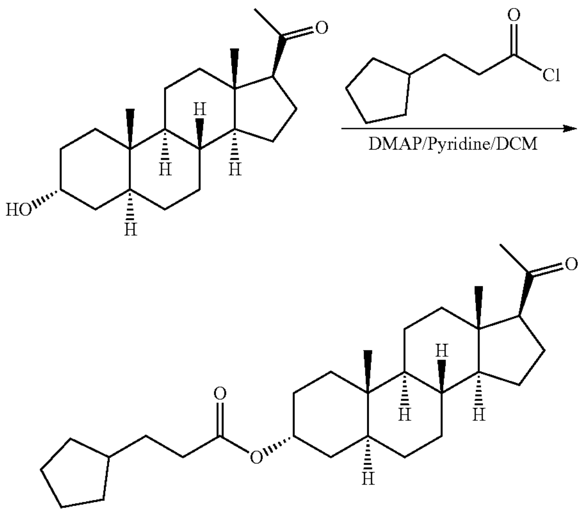

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylpropanoate was prepared following the same procedure as Example 1, except changing hexanoyl chloride to 3-cyclopentylpropanoyl chloride. $^{1}$H NMR (400 MHz, $CDCl_3$) δ (ppm) 5.02 (bs, 1H), 2.54-2.50 (m, 1H), 2.32-2.28 (m, 2H), 2.17-2.11 (m, 4H), 2.02-2.00 (m, 1H), 1.71-1.61 (m, 8H), 1.48-1.15 (m, 18H), 0.93-0.89 (m, 4H), 0.83-0.76 (m, 4H), 0.61 (s, 3H). $^{13}$C NMR (100 MHz, $CDCl_3$) δ (ppm) 209.70, 172.91, 69.64, 63.84, 56.76, 54.17, 44.26, 41.06, 40.13, 39.08, 37.15, 36.72, 35.45, 33.02, 32.98, 32.44, 31.94, 31.58, 28.28, 26.05, 25.05, 24.38, 22.90, 20.81, 13.47, 11.35.

Example 8

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylacetate

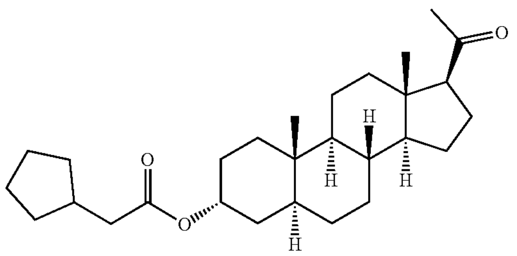

Step 1: Preparation of 2-cyclopentylacetyl chloride

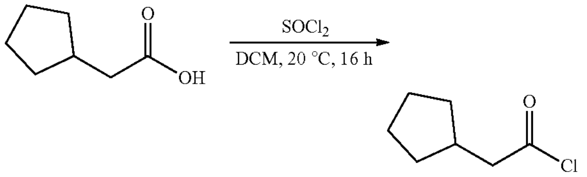

To a solution of 2-cyclopentylacetic acid (0.80 g, 6.24 mmol, 0.784 mL, 1.0 eq) in DCM (10 mL) was added DMF (38.0 mg, 0.51 mmol, 0.040 mL, 0.1 eq), then $SOCl_2$ (1.86 g, 15.60 mmol, 1.13 mL, 2.5 eq) was added dropwise at 0° C. The mixture was stirred at 20 ° C. for 2 h and was then concentrated. The resulting crude product 2-cyclopentylacetyl chloride (900 mg, light yellow oil) was used for next reaction without further purification.

Step 2: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylacetate

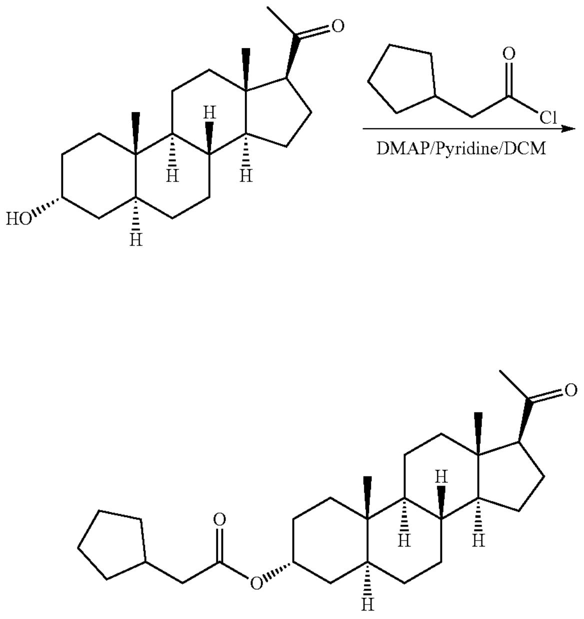

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylacetate was prepared following the same procedure as Example 1, except changing hexanoyl chloride to 2-cyclopentylacetyl chloride (126 mg, 31.2% yield). LCMS (ESI) m/z calcd for $C_{28}H_{44}O_3$ 428.33, found 429.33 $(M+H)^+$. $^1H$ NMR (400 MHz, $CDCl_3$) δ (ppm) 5.04 (s, 1H), 2.53 (t, J=8.0 Hz, 1H), 2.38-2.11 (m, 6H), 1.82-1.84 (m, 1H), 1.94-1.08 (m, 27H), 1.01-0.89 (m, 1H), 0.86-0.72 (m, 4H), 0.61 (s, 3H). $^{13}C$ NMR (100 MHz, $CDCl_3$) δ (ppm) 209.79, 172.96, 69.67, 63.88, 56.76, 54.17, 44.28, 41.05, 40.14, 39.92, 39.07, 36.73, 36.26, 35.83, 35.47, 32.91, 32.45, 32.43, 31.94, 28.29, 26.16, 25.07, 25.05, 24.38, 20.82, 13.48, 11.36.

Example 9

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 3-cyclopentylpropanoate

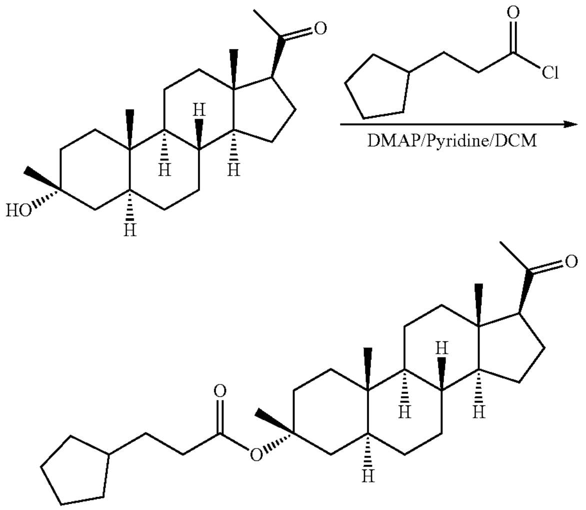

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl]3 -cyclopentylpropanoate was prepared following the same procedure as Example 1, except changing hexanoyl chloride to 3-cyclopentylpropanoyl chloride and replacing 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone with 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl] ethenone (90.0 mg, 13.0% yield). $^1H$ NMR (400 MHz, $CDCl_3$) δ (ppm) 2.53 (t, J=8.0 Hz, 1H), 2.27-2.12 (m, 7H), 2.04-1.79 (m, 4H), 1.74-1.14 (m, 27H), 0.94-0.83 (m, 2H), 0.81-0.66 (m, 4H), 0.61 (s, 3H). $^{13}C$ NMR (100 MHz, $CDCl_3$) δ (ppm) 209.22, 172.32, 81.14, 63.34, 56.24, 53.82, 43.78, 41.50, 40.56, 38.57, 38.47, 36.25, 34.99, 34.82, 33.62, 32.00, 31.96, 31.90, 31.50, 31.03, 27.50, 25.86, 24.55, 23.87, 22.26, 20.50, 12.97, 11.19.

Example 10

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 2-cyclopentylacetate

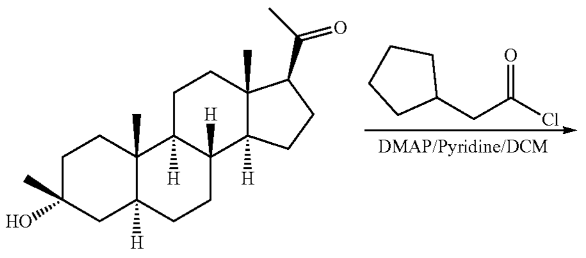

-continued

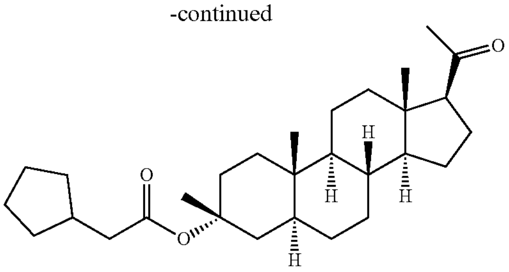

[(3R,5S,8R,9S,10S,13S,14S,17S)-17-acetyl-3,10,13-trimethyl-1,2,4,5,6,7,8,9,11,12,14,15,16,17-tetradecahydro-cyclopenta[a]phenanthren-3-yl] 2-cyclopentylacetate was prepared following the same procedure as Example 1, except changing hexanoyl chloride to 2-cyclopentylacetyl chloride and replacing 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone with 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl]ethenone (106 mg, 26.5% yield). LCMS (ESI) m/z calcd for $C_{29}H_{46}O_3$ 442.34, found 443.3 $(M+H)^+$. 1H NMR (400 MHz, $CDCl_3$) δ (ppm) 2.53 (t, J=8.0 Hz, 1H), 2.32-2.08 (m, 8H), 2.05-1.79 (m, 4H), 1.74-1.10 (m, 24H), 0.99-0.85 (m, 2H), 0.82-0.66 (m, 4H), 0.61 (s, 3H). $^{13}C$ NMR (100 MHz, $CDCl_3$) § (ppm) 209.73, 172.84, 81.66, 63.87, 56.76, 54.34, 44.30, 42.03, 41.09, 39.10, 38.99, 36.77, 35.52, 35.34, 34.15, 32.53, 32.48, 32.43, 32.03, 31.56, 28.03, 26.92, 26.39, 25.06, 24.39, 22.79, 21.02, 13.49, 11.72.

Example 11

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopent-3-en-1-ylpropanoate

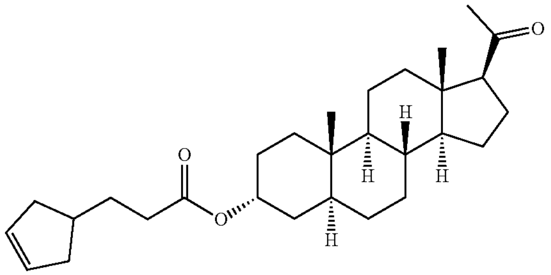

Step 1: Preparation of ethyl 3-(cyclopent-3-en-1-yl)propanoate

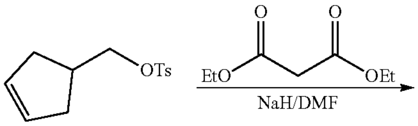

-continued

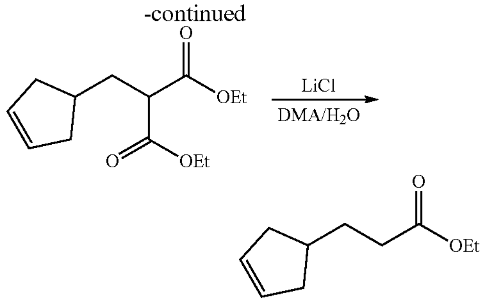

To a solution of diethyl propanedioate (1.27 g, 7.93 mmol, 1.20 mL, 2.0 eq) in anhydrous DMF (10 mL) at 0° C. was added NaH (317 mg, 7.93 mmol, 60%, 2.0 eq) and the resulting reaction mixture was then stirred at 25° C. for 30 min. A solution of cyclopent-3-en-1-ylmethyl 4-methylbenzenesulfonate (1.0 g, 3.96 mmol, 1.0 eq) in anhydrous DMF (5 mL) at 25° C. was added dropwise to the above mixture and the resulting reaction mixture was stirred at 60° C. for 12 h. The reaction mixture was combined with another batch. The reaction mixture was diluted with $H_2O$ (50 mL) and extracted with EtOAc (60 mL×3). The combined organic layers were washed with brine (100 mL), dried over $Na_2SO_4$, filtered and concentrated. The crude product was purified by flash silica gel chromatography (ISCO®; 20 g SepaFlash® Silica Flash Column, eluted with 0-10% ethyl acetate/petroleum ether gradient @35 mL/min) to give diethyl 2-(cyclopent-3-en-1-ylmethyl) propanedioate (1.7 g, 7.07 mmol, 89.3% yield) as a colorless oil.

To a mixture of diethyl 2-(cyclopent-3-en-1-ylmethyl) propanedioate (800 mg, 3.33 mmol, 1 eq) in DMA (10 mL) and $H_2O$ (1 mL) was added LiCl (706 mg, 16.65 mmol, 5.0 eq). The reaction mixture was stirred at 135° C. for 12 h. The reaction mixture was combined with another batch. The reaction mixture was diluted with $H_2O$ (30 mL) and extracted with EtOAc (30 mL×3). The combined organic layers were washed with brine (50 mL), dried over $Na_2SO_4$, filtered and concentrated. The crude product was purified by flash silica gel chromatography (ISCO®; 20 g SepaFlash® Silica Flash Column, eluted 0-10% ethyl acetate/petroleum ether gradient @ 30 mL/min) to give ethyl 3-cyclopent-3-en-1-ylpropanoate (750 mg, 4.46 mmol, 67.0% yield) as a brown oil. $^1H$ NMR (400 MHz, $CDCl_3$) δ (ppm) 5.67 (m, 2H), 4.21-4.10 (m, 2H), 2.52-2.45 (m, 2H), 2.40-2.30 (m, 2H), 2.28-2.21 (m, 1H), 2.01-1.92 (m, 2H), 1.80-1.71 (m, 2H), 1.28-1.24 (m, 3H).

Step 2: Preparation of 3-(cyclopent-3-en-1-yl) propanoyl chloride

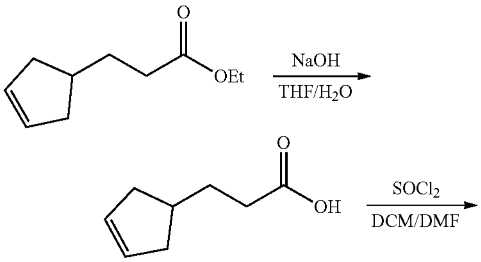

-continued

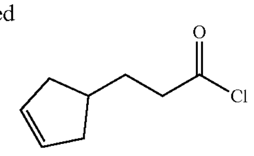

To a mixture of ethyl 3-cyclopent-3-en-1-ylpropanoate (750 mg, 4.46 mmol, 1.0 eq) in THF (5 mL) and $H_2O$ (5 mL) was added NaOH (892 mg, 22.29 mmol, 5.0 eq). The reaction mixture was stirred at 25° C. for 1 h, and then was acidified with HCl (1 N, 20 mL). The reaction mixture was diluted with $H_2O$ (30 ml) and extracted with EtOAc (30 mL×3). The combined organic layers were washed with brine (50 mL), dried over $Na_2SO_4$, filtered and concentrated. The resulting crude product 3-cyclopent-3-en-1-ylpropanoic acid (600 mg, 96.0% yield, brown oil) was used for the next reaction without future purification.

To a mixture of 3-cyclopent-3-en-1-ylpropanoic acid (100 mg, 0.713 mmol, 1.0 eq) in DCM (5 mL) and DMF (0.05 mL) at 0° C. was added $SOCl_2$ (170 mg, 1.43 mmol, 0.103 mL, 2.0 eq). The reaction mixture was then stirred at 20° C. for 3 h. The reaction mixture was concentrated under reduced pressure to give 3-cyclopent-3-en-1-ylpropanoyl chloride (120 mg, crude, light yellow oil), which was used for the next reaction without future purification.

Step 3: Preparation of [(3R,5S,8R,9S,10S,13S,14S, 17S)-17-acetyl-10,13-dimethyl-2,3,4,5,6,7,8,9,11,12, 14,15,16,17-tetradecahydro-1H-cyclopenta[a] phenanthren-3-yl] 3-cyclopent-3-en-1-ylpropanoate

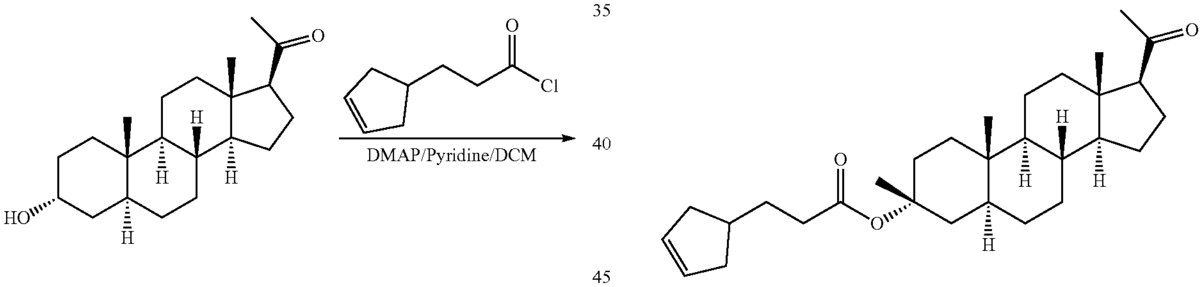

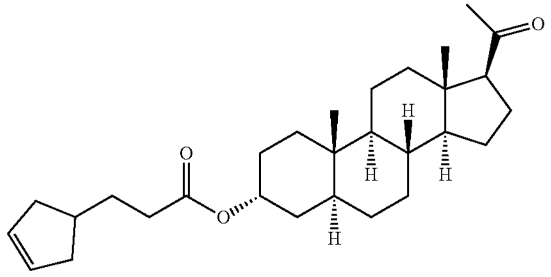

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopent-3-en-1-ylpropanoate was prepared following the same procedure as Example 1, except changing hexanoyl chloride to 3-cyclopent-3-en-1-ylpropanoyl chloride (117 mg, 41.8% yield). $^1$H NMR (400 MHz, $CDCl_3$) δ (ppm) 5.87 (s, 2H), 5.02 (s, 1H), 2.54-2.49 (m, 3H), 2.34-2.17 (m, 4H), 2.11 (s, 3H), 2.02-1.95 (m, 3H), 1.77-1.60 (m, 8H), 1.52-1.37 (m, 6H), 1.30-1.12 (m, 6H), 1.00-0.91 (m, 1H), 0.83-0.76 (m, 4H), 0.60 (s, 3H). $^{13}$C NMR (100 MHz, $CDCl_3$) δ (ppm) 209.66, 173.30, 129.81, 69.79, 63.86, 56.77, 54.15, 44.26, 40.12, 39.08, 38.67, 38.64, 37.18, 35.83, 35.46, 33.72, 32.99, 32.89, 31.91, 31.58, 31.53, 28.28, 26.13, 24.38, 22.79, 20.81, 13.47, 11.35.

Example 12

[(3R,5S,8R,9S,10S,13S,14S,17S)-17-acetyl-3,10,13-trimethyl-1,2,4,5,6,7,8,9,11,12,14,15,16,17-tetra-decahydrocyclopenta[a]phenanthren-3-yl] 3-cyclo-pent-3-en-1-ylpropanoate

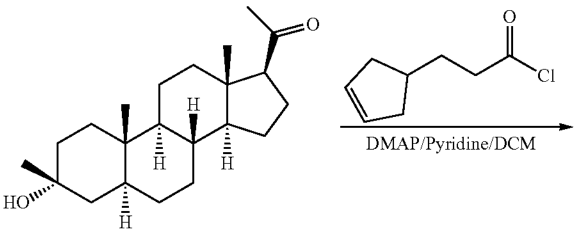

[(3R,5S,8R,9S, 10S,13S,14S,17S)-17-acetyl-3,10,13-trimethyl-1,2,4,5,6,7,8,9,11,12,14,15,16,17-tetradecahydro-cyclopenta[a]phenanthren-3-yl] 3-cyclopent-3-en-1-ylpro-panoate was prepared following the same procedure as Example 1, except changing hexanoyl chloride to 3-cyclo-pent-3-en-1-ylpropanoyl chloride and replacing 1-[(3R,5S, 8R,9S,10S,13S,14S,17S)-3-hydroxy-10,13-dimethyl-2,3,4, 5,6,7,8,9,11,12,14,15,16,17-tetradecahydro-1H-cyclopenta [a]phenanthren-17-yl]ethanone with 1-[(3R,5S,8R,9S,10S, 13S,14S,17S)-3-hydroxy-3,10,13-trimethyl-1,2,4,5,6,7,8,9, 11,12,14,15,16,17-tetradecahydrocyclopenta[a] phenanthren-17-yl]ethenone (101 mg, 21.1% yield). $^1$H NMR (400 MHz, $CDCl_3$) § (ppm) 5.68 (m, 2H), 2.55-2.48 (m, 3H), 2.32-2.13 (m, 5H), 2.12 (s, 3H), 2.03-1.91 (m, 4H), 1.75-1.61 (m, 5H), 1.51-1.11 (m, 15H), 0.98-0.86 (m, 2H), 0.78-0.70 (m, 4H), 0.61 (s, 3H). $^{13}$C NMR (100 MHz, $CDCl_3$) δ (ppm) 209.72, 173.16, 129.80, 81.72, 63.85, 56.72, 54.25, 44.26, 41.08, 39.04, 38.65, 37.15, 35.46, 35.29, 34.57, 34.16, 32.24, 31.86, 31.66, 31.25, 27.97, 26.34, 26.25, 24.35, 22.76, 13.43, 11.67.

Example 13

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-(5-oxotetrahydrofuran-2-yl)propanoate

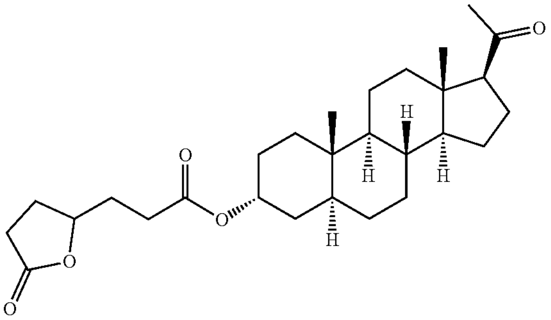

Step 1: Preparation of 4-oxoheptanedioyl dichloride

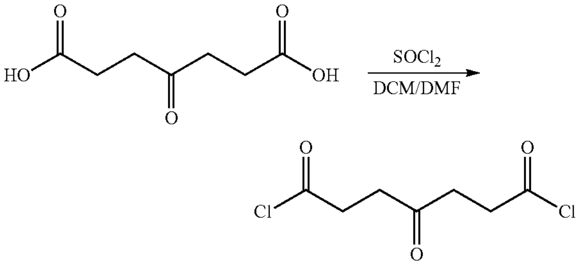

To a mixture of 4-oxoheptanedioic acid (1.0 g, 5.74 mmol, 1.0 eq) in DCM (10 mL) at 0° C. was added DMF (0.05 mL) followed by $SOCl_2$ (1.71 g, 14.36 mmol, 1.04 mL, 2.5 eq). The reaction mixture was stirred at 20° C. for 3 h. The reaction mixture was concentrated to give 4-oxoheptanedioyl dichloride (1.3 g, crude) as a light-yellow oil, which was used for next step without further purification.

Step 2: Preparation of 7-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxy]-4,7-dioxo-heptanoic acid

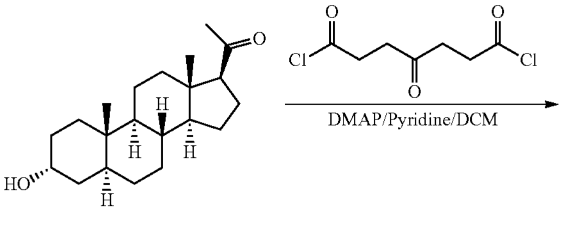

-continued

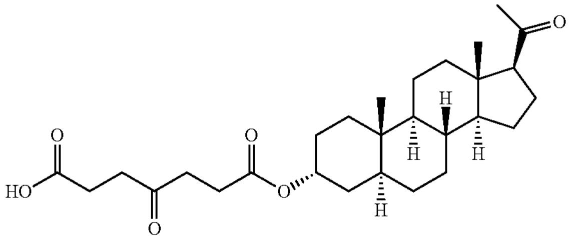

7-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxy]-4,7-dioxo-heptanoic acid was prepared following the same procedure as Example 1, except changing hexanoyl chloride to 4-oxo-heptanedioyl dichloride (1.0 g, 40.0% yield). $^1H$ NMR (400 MHz, $CDCl_3$) δ (ppm) 5.01 (bs, 1H), 2.85-2.75 (m, 4H), 2.69-2.61 (m, 4H), 2.53 (t, J=8.0 Hz, 1H), 2.23-2.00 (m, 5H), 1.78-1.10 (m, 19H), 1.03-0.90 (m, 1H), 0.83-0.80 (m, 4H), 0.61 (s, 3H).

Step 3: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-(5-oxotetrahydrofuran-2-yl)propanoate

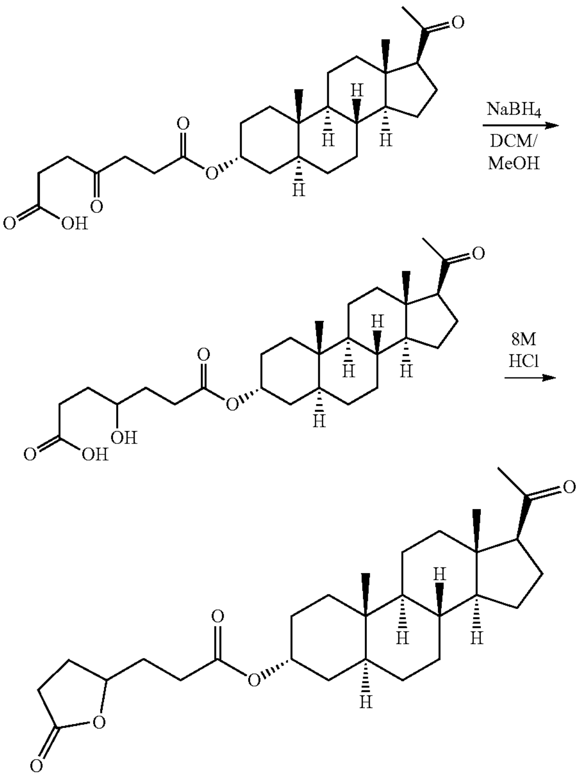

To a mixture of 7-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxy]-4,7-dioxo-heptanoic acid (500 mg, 1.05 mmol, 1.0 eq) (59.8 mg, 1.58 mmol, 1.5 eq) in DCM (5 mL) and MeOH (5 mL) was added $NaBH_4$. The reaction mixture was stirred at 20°

C. for 12 h and was then concentrated to give 7-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxy]-4-hydroxy-7-oxo-heptanoic acid (500 mg, 99.6% yield, crude) as a light yellow oil, which was used for next step without further purification.

To a mixture of 7-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxy]-4-hydroxy-7-oxo-heptanoic acid (500 mg, 1.05 mmol, 1 eq) in DCM (10 mL) was added HCl (8 M, 10.0 mL, 76 eq). The reaction mixture was stirred at 25° C. for 2 h before it was diluted with $H_2O$ (30 mL) and extracted with DCM (30 mL×3). The combined organic layers were washed with brine (50 mL), dried over $Na_2SO_4$, filtered and concentrated. The crude product was purified by flash silica gel chromatography (ISCO®; 20 g SepaFlash® Silica Flash Column, eluted with 0-50% ethylacetate/petroleum ether gradient @ 35 mL/min) to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-(5-oxotetrahydrofuran-2-yl)propanoate (228 mg, 46.9% yield, 99% purity) as a white solid. LCMS (ESI) m/z calcd for $C_{28}H_{42}O_5$ 458.30, found 481.3 (M+Na)+. $^1$H NMR (400 MHz, $CDCl_3$) δ (ppm) 5.05 (s, 1H), 4.60-4.53 (m, 1H), 2.59-2.46 (m, 5H), 2.42-2.34 (m, 1H), 2.20-2.12 (m, 4H), 2.06-1.87 (m, 4H), 1.74-1.61 (m, 6H), 1.54-1.39 (m, 6H), 1.30-1.14 (m, 6H), 1.01-0.91 (m, 1H), 0.84-0.77 (m, 4H), 0.61 (s, 3H). $^{13}$C NMR (100 MHz, $CDCl_3$) δ (ppm) 209.71, 176.83, 172.08, 79.74, 79.72, 70.40, 70.34, 63.81, 56.68, 54.01, 44.22, 40.04, 39.00, 35.78, 35.41, 32.86, 31.85, 31.52, 30.78, 30.68, 30.63, 28.72, 28.20, 27.88, 25.98, 24.33, 22.74, 13.43, 11.31.

Example 14

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-acetoxybutanoate

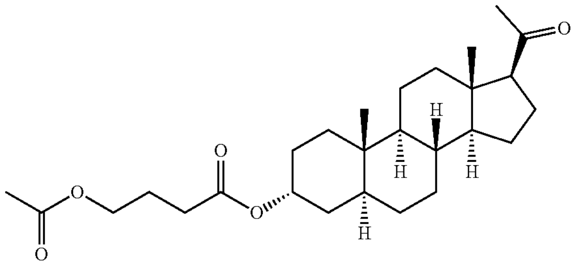

Step 1: Preparation of benzyl 4-acetoxybutanoate

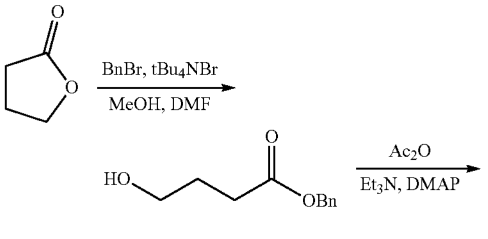

-continued

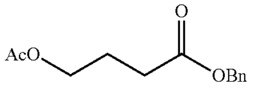

To a mixture of tetrahydrofuran-2-one (2.0 g, 23.23 mmol, 1.77 mL, 1.0 eq) in MeOH (25 mL) was added tetrabutylammonium hydroxide (6.03 g, 23.23 mmol, 7.53 mL, 1.0 eq), the resulting mixture was stirred at 70° C. for 2 h. The mixture was then concentrated, and the residue was dissolved in DMF (25 mL), BnBr (3.97 g, 23.23 mmol, 2.76 mL, 1.0 eq) was added slowly. The resulting mixture was stirred at 25° C. for 16 h. The mixture was then diluted with EtOAc (250 mL), washed with water (50 mL×3). The organic layer was separated, dried over $Na_2SO_4$, filtered and concentrated. The crude product was purified by flash silica gel chromatography (ISCO®; 20 g SepaFlash® Silica Flash Column, eluted with 0-40% ethyl acetate/petroleum ether gradient @ 35 mL/min) to give benzyl 4-hydroxybutanoate (2.2 g, 11.33 mmol, 48.8% yield, 100% purity) as a colorless oil. LCMS (ESI) m/z calcd for $C_{11}H_{14}O_3$ 194.09, found 195.1 $(M+H)^+$. $^1$H NMR (400 MHz, DMSO-$d_6$) 7.39-7.16 (m, 5H), 5.08 (s, 2H), 4.26 (t, J=6.8 Hz, 1H), 3.41-3.40 (m, 2H), 2.40-2.37 (m, 2H), 1.70-1.66 (m, 2H).

To a mixture of benzyl 4-hydroxybutanoate (400 mg, 2.06 mmol, 1.0 eq) in DCM (10 mL) was added DMAP (37.7 mg, 0.309 mmol, 0.15 eq), $Et_3N$ (208 mg, 2.06 mmol, 0.287 mL, 1.0 eq) and acetyl acetate (210. mg, 2.06 mmol, 0.193 mL, 1.0 eq) at 0° C., and then the mixture was stirred at 25° C. for 16 h under $N_2$. The mixture was diluted with water (30 mL), then the mixture was extracted with EtOAc (30 mL×3), then organic layers were washed with brine (50 mL), dried over $Na_2SO_4$, filtered and concentrated. The residue was purified by flash silica gel chromatography (ISCOR; 4 g SepaFlash® Silica Flash Column, eluted with 0-10% ethyl acetate/petroleum ether gradient @ 30 mL/min) to give benzyl 4-acetoxybutanoate (410 mg, 84.3% yield, 100% purity) as a colorless oil. LCMS (ESI) m/z calcd for $C_{13}H_{16}O_4$ 236.1, found 237.1 $(M+H)^+$, 259.2 $(M+Na)^+$. $^1$H NMR (400 MHz, $CDCl_3$) 7.40-7.33 (m, 5H), 5.13 (s, 2H), 4.13-4.09 (m, 3H), 2.48-2.43 (m, 2H), 2.03 (s, 3H), 2.00-1.96 (m, 2H).

Step 2: Preparation of 4-chloro-4-oxobutyl acetate

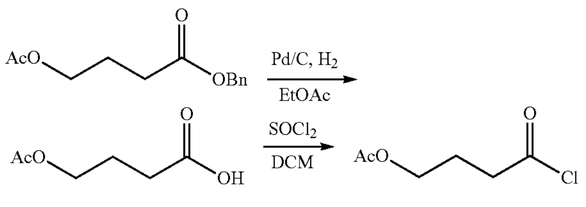

To a solution of benzyl 4-acetoxybutanoate (410 mg, 1.74 mmol, 1 eq) in EtOAc (10 mL) under $N_2$ was added Pd/C (50 mg, 10% on carbon). The resulting suspension was degassed under vacuum and purged with $H_2$ several times. The mixture was stirred under $H_2$ (15 psi) at 25° C. for 3 h. The reaction mixture was filtered, and the filtrate was concentrated to give 4-acetoxybutanoic acid (300 mg, crude) was obtained as a colorless oil, which was used directly for next step without further purification.

To a mixture of 4-acetoxybutanoic acid (150 mg, 1.03 mmol, 1 eq) in DCM (5 mL) at 0° C. under $N_2$ was added $SOCl_2$ (246 mg, 2.07 mmol, 0.15 mL, 2.0 eq), and then the mixture was stirred at 25° C. for 16 h atmosphere. The mixture was concentrated to give 4-chloro-4-oxobutyl acetate (160 mg, crude) as a colorless oil, which was used directly for next step without further purification.

Step 3: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-acetoxybutanoate

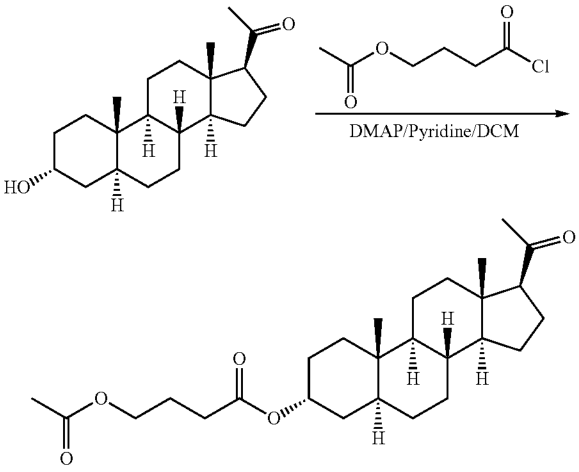

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4 -acetoxybutanoate was prepared following the same procedure as Example 1, except changing hexanoyl chloride to 4-chloro-4-oxobutyl acetate (68.4 mg, 16.8% yield, 100% purity). LCMS (ESI) m/z calcd for $C_{27}H_{42}O_5$ 446.40, found 469.1 $(M+Na)^+$. $^1H$ NMR (400 MHz, $CDCl_3$) δ (ppm) 5.04 (d, J=2.8 Hz, 1H), 4.12 (t, J=6.4 Hz, 2H), 2.53 (t, J=8.8 Hz, 1H), 2.39 (t, J=7.4 Hz, 2H), 2.23-1.91 (m, 10H), 1.71-1.16 (m, 18H), 1.02-0.90 (m, 1H), 0.83-0.80 (m, 4H), 0.61 (s, 3H). $^{13}C$ NMR (100 MHz, $CDCl_3$) δ (ppm) 209.72, 172.28, 171.03, 70.19, 63.83, 63.55, 56.73, 54.07, 44.25, 40.09, 39.05, 35.80, 35.41, 32.91, 32.84, 31.85, 31.55, 31.31, 28.23, 26.08, 24.36, 24.13, 22.76, 20.96, 20.79, 13.46, 11.33.

Example 15

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-(2-methylpropanoyloxy) butanoate

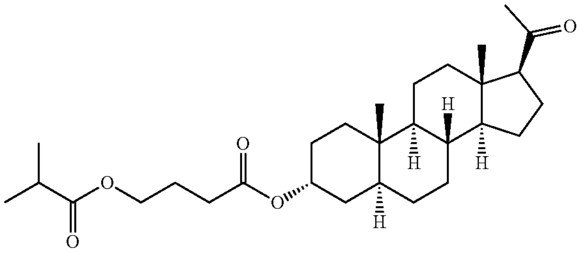

Step 1: Preparation of 4-chloro-4-oxobutyl isobutyrate 4-chloro-4-oxobutyl isobutyrate was prepared following the same procedure as preparation of 4-chloro-4-oxobutyl acetate from benzyl 4-hydroxybutanoate, except replacing acetyl acetate with isobutyryl chloride.

Step 2: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-(2-methylpropanoyloxy) butanoate

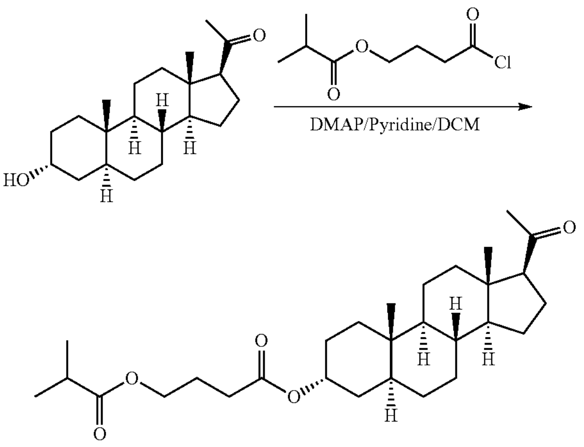

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-(2-methylpropanoyloxy) butanoate was prepared following the same procedure as Example 1, except changing hexanoyl chloride to 4-chloro-4-oxobutyl isobutyrate (114 mg, 28.9% yield, 100% purity). LCMS (ESI) m/z calcd for $C_{29}H_{46}O_5$ 474.33, found 497.2 $(M+Na)^+$. $^1H$ NMR (400 MHz, $CDCl_3$) δ (ppm) 5.04 (s, 1H), 4.12 (t, J=6.4 Hz, 2H), 2.61-2.50 (m, 2H), 2.41 (t, J=7.2 Hz, 2H), 2.22-2.12 (m, 1H), 2.24-2.06 (m, 3H), 2.03-1.95 (m, 3H), 1.75-1.03 (m, 23H), 1.03-0.90 (m, 1H), 0.83-0.76 (m, 4H), 0.61 (s, 3H). $^{13}C$ NMR (100 MHz, $CDCl_3$) δ (ppm) 209.71, 177.05, 172.30, 70.18, 63.83, 63.27, 56.73, 54.06, 44.24, 40.07, 39.04, 35.79, 35.41, 33.96, 32.91, 32.83, 31.84, 31.54, 31.25, 28.22, 26.07, 24.35, 24.21, 22.75, 20.78, 19.01, 13.45, 11.33.

Example 16

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-acetoxy pentanoate

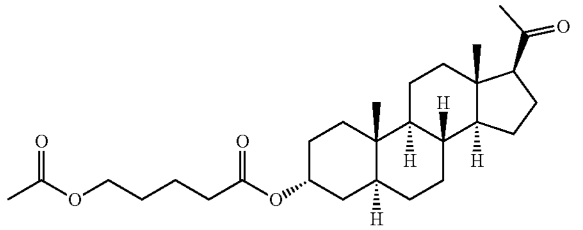

Step 1: Preparation of 5-acetoxypentanoic acid

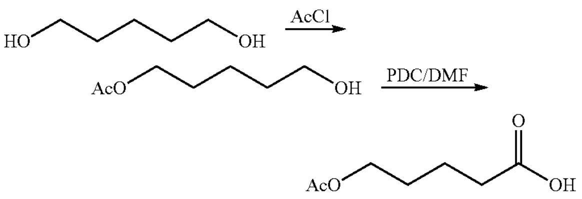

To a mixture of pentane-1,5-diol (3.0 g, 28.81 mmol, 3.03 mL, 1.0 eq), $Et_3N$ (4.37 g, 43.21 mmol, 6.01 mL, 1.5 eq) in DCM (40 mL) was added acetyl chloride (2.26 g, 28.81 mmol, 2.06 mL, 1.0 eq), and then the mixture was stirred at 25° C. for 16 h under $N_2$ atmosphere. The mixture was diluted with water (30 mL) and then was extracted with DCM (30 mL×2). The combined organic layers were combined, dried over $Na_2SO_4$, filtered and concentrated. The crude product was purified by flash silica gel chromatography (ISCO®; 20 g SepaFlash® Silica Flash Column, eluted of 0~50% ethyl acetate/petroleum ether gradient @ 35 mL/min) to give 5-hydroxypentyl acetate (900 mg, 6.16 mmol, 21.4% yield) as a colorless oil. $^1H$ NMR (400 MHz, $CDCl_3$) 4.07 (t, J=6.8 Hz, 2H), 3.65 (t, J=6.4 Hz, 2H), 2.04 (s, 3H), 1.68-1.58 (m, 4H), 1.47-1.39 (m, 2H).

To a mixture of 5-hydroxypentyl acetate (260 mg, 1.78 mmol, 1.0 eq) in DMF (8 mL) was added PDC (2.01 g, 5.34 mmol, 3.0 eq). The resulting mixture was stirred at 25° C. for 16 h. The reaction mixture was combined with another batch, diluted with EtOAc (100 mL), then washed water (30 mL×3). The organic layer was separated, dried over $Na_2SO_4$, filtered and concentrated. The crude product was purified by flash silica gel chromatography (ISCOR; 4 g SepaFlash® Silica Flash Column, eluted with 0~100% ethyl acetate/petroleum ether gradient @ 25 mL/min) to give 5-acetoxypentanoic acid (160 mg, 56.0% yield) as a colorless oil. $^1H$ NMR (400 MHz, $CDCl_3$) 4.09 (t, J=6.0 Hz, 2H), 2.45-2.37 (m, 2H), 2.06 (s, 3H), 1.77-1.60 (m, 4H).

Step 2: Preparation of (5-chloro-5-oxo-pentyl)acetate

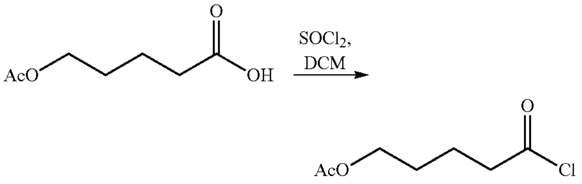

To a mixture of 5-acetoxypentanoic acid (160 mg, 1.00 mmol, 1.0 eq) in DCM (6 mL) was added $SOCl_2$ (238 mg, 2.00 mmol, 0.145 mL, 2.0 eq) and DMF (14.6 mg, 0.200 mmol, 0.015 mL, 0.2 eq), and then the mixture was stirred at 25° C. for 16 h under $N_2$ atmosphere. The mixture was concentrated. Compound (5-chloro-5-oxo-pentyl)acetate (180 mg, crude) was obtained as a yellow oil, which was used directly for next step without further purification.

Step 3: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-acetoxypentanoate

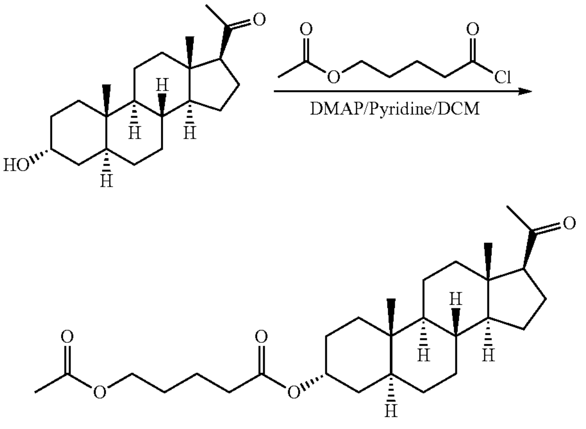

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-acetoxyp entanoate was prepared following the same procedure as Example 1, except changing hexanoyl chloride to (5-chloro-5-oxo-pentyl)acetate (202 mg, 43% yield, 99.3% purity). LCMS (ESI) m/z calcd for $C_{28}H_{44}O_5$ 460.32, found 483.3 $(M+Na)^+$. $^1H$ NMR (400 MHz, $CDCl_3$) δ (ppm) 5.04 (s, 1H), 4.14-4.08 (m, 2H), 2.53 (t, J=8.9 Hz, 1H), 2.37-2.34 (m, 2H), 2.22-2.12 (m, 4H), 2.06-2.00 (m, 4H), 1.73-1.63 (m, 9H), 1.54-1.13 (m, 13H), 1.00-0.90 (m, 1H), 0.83-0.77 (m, 4H), 0.61 (s, 3H). $^{13}C$ NMR (100 MHz, $CDCl_3$)209.75, 172.75, 171.17, 69.98, 64.01, 63.82, 56.72, 54.10, 44.24, 40.09, 39.03, 35.80, 35.41, 34.24, 32.93, 32.85, 31.87, 31.54, 28.23, 28.01, 26.10, 24.35, 22.75, 21.57, 20.99, 20.78, 13.45, 11.33.

Example 17

[(3R,5S,8R,9S,10S,13S,14S,17S)-17-acetyl-10,13-dimethyl-2,3,4,5,6,7,8,9,11,12,14, 15,16,17-tetradecahydro-1H-cyclopenta[a]phenanthren-3-yl] 5-acetoxy-2-methyl-pentanoate

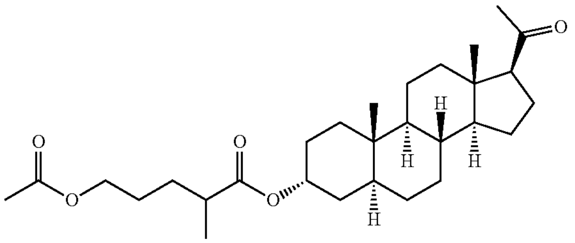

Step 1: Preparation of diethyl 2-(3-(benzyloxy) propyl)-2-methylmalonate

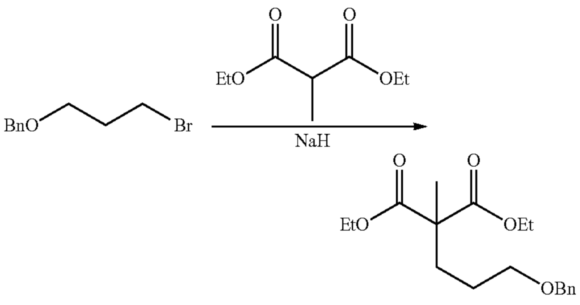

To a mixture of diethyl 2-methylpropanedioate (2.28 g, 13.09 mmol, 2.24 mL, 1.0 eq) in THF (35 mL) was added NaH (1.05 g, 26.19 mmol, 60.0%, 2.0 eq) at 0° C., then 3-bromopropoxymethylbenzene (3.0 g, 13.09 mmol, 1.0 eq) in THF (5 mL) was added, and then the mixture was stirred at 25° C. for 16 h under $N_2$ atmosphere. The mixture was quenched by water (60 mL), the resulting mixture was extracted with EtOAc (60 mL×3). The combined organic layers were dried over $Na_2SO_4$, filtered and concentrated. The residue was purified by flash silica gel chromatography (ISCO®; 40 g SepaFlash® Silica Flash Column, eluted with 0~30% ethyl acetate/petroleum ether gradient @ 35 mL/min) to give diethyl 2-(3-benzyloxypropyl)-2-methyl-propanedioate (2.29 g, 54.3% yield) as a colorless oil.

Step 2: Preparation of 5-(benzyloxy)-2-methylpentanoic acid

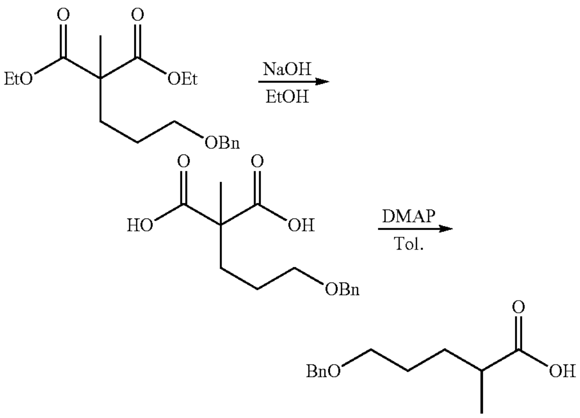

A mixture of diethyl 2-(3-benzyloxypropyl)-2-methyl-propanedioate (2.39 g, 7.41 mmol, 1.0 eq), KOH (2.50 g, 44.48 mmol, 6.0 eq) in EtOH (40 mL) was stirred at 90° C. for 5 h. The mixture was diluted with water (70 mL), extracted with 2-methoxy-2-methylpropane (50 mL×2). The aqueous layer was acidified with HCl (1M) to pH=1, extracted with EtOAc (100 mL×4). The combined organic layers were washed with brine (80 mL), dried over $Na_2SO_4$, filtered and concentrated to give 2-(3-benzyloxypropyl)-2-methyl-propanedioic acid (2.0 g, crude) as a yellow oil. LCMS (ESI) m/z calcd for $C_{14}H_{18}O_5$ 266.12, found 288.9 $(M+Na)^+$.

A mixture of 2-(3-benzyloxypropyl)-2-methyl-propanedioic acid (2 g, 7.51 mmol, 1 eq) and DMAP (183 mg, 1.50 mmol, 0.2 eq) in toluene (40 mL) was stirred at 125° C. for 5 h. The mixture was concentrated and the resulting residue was purified by flash silica gel chromatography (ISCO®; 10 g SepaFlash® Silica Flash Column, eluted 0~50% ethyl acetate/petroleum ether gradient @ 35 mL/min) to give 5-benzyloxy-2-methyl-pentanoic acid (720 mg, 38.0% yield, 88% purity) as a yellow oil. LCMS (ESI) m/z calcd for $C_{13}H_{18}O_3$ 222.13, found 245.0 $(M+Na)^+$.

Step 3: Preparation of [(3R,5S,8R,9S,10S,13S,14S, 17S)-17-acetyl-10,13-dimethyl-2,3,4,5,6,7,8,9,11,12, 14,15,16,17-tetradecahydro-1H-cyclopenta[a] phenanthren-3-yl] 5-benzyloxy-2-methyl-pentanoate

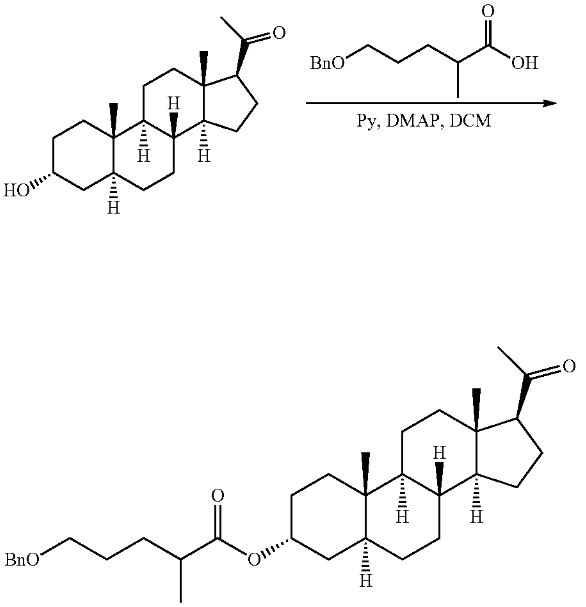

A mixture of 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone (1.03 g, 3.24 mmol, 1.0 eq), 5-benzyloxy-2-methyl-pentanoic acid (720 mg, 3.24 mmol, 1.0 eq), DMAP (79.2 mg, 0.65 mmol, 0.2 eq), EDCI (931 mg, 4.86 mmol, 1.5 eq) and $Et_3N$ (1.47 g, 14.58 mmol, 2.03 mL, 4.5 eq) in DCM (20 mL) was stirred at 25° C. for 16 h. The mixture was concentrated. The residue was purified by flash silica gel chromatography (ISCOR; 40 g SepaFlash® Silica Flash Column, Eluent of 0~15% Ethyl acetate/Petroleum ether gradient @ 35 mL/min). Compound [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-benzyloxy-2-methyl-pentanoate (610 mg, 1.15 mmol, 35.5% yield) was obtained as a colorless oil. LCMS (ESI) m/z calcd for $C_{34}H_{50}O_4$ 522.37, found 523.4 $(M+H)^+$.

Step 4: Preparation of (3R,5S,8R,9S,10S,13S,14S,17S)-17-acetyl-10,13-dimethylhexadecahydro-1H-cyclopenta[a]phenanthren-3-yl 5-hydroxy-2-methyl-pentanoate

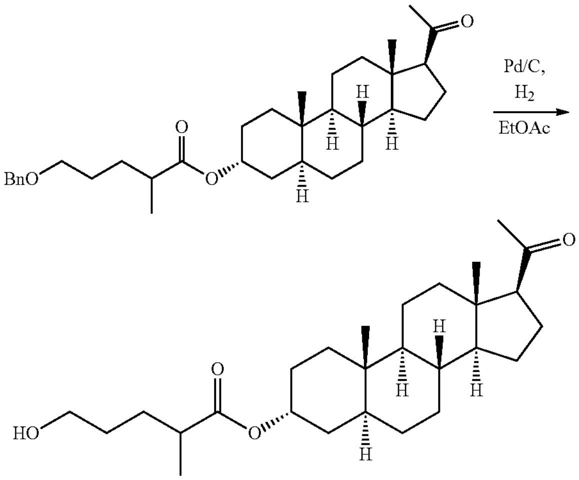

To a solution of [(3R,5S,8R,9S,10S,13S,14S,17S)-17-acetyl-10,13-dimethyl-2,3,4,5, 6,7,8,9,11,12,14,15,16,17-tetradecahydro-1H-cyclopenta[a]phenanthren-3-yl] 5 -benzyloxy-2-methyl-pentanoate (100 mg, 0.19 mmol, 1.0 eq) in EtOAc (10 mL) was added Pd/C (10%, 20.0 mg) under $N_2$. The suspension was degassed under vacuum and purged with $H_2$ several times. The mixture was stirred under $H_2$ (15 psi) at 25° C. for 4 h. The reaction mixture was filtered, and the filtrate was concentrated to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-hydroxy-2-methyl-pentanoate (80.0 mg, 96.7% yield) as a colorless oil, which was used for the next reaction without further purification.

Step 5: Preparation of [(3R,5S,8R,9S,10S,13S,14S,17S)-17-acetyl-10,13-dimethyl-2,3,4,5,6,7,8,9,11,12,14, 15,16,17-tetradecahydro-1H-cyclopenta[a]phenanthren-3-yl] 5-acetoxy-2-methyl-pentanoate

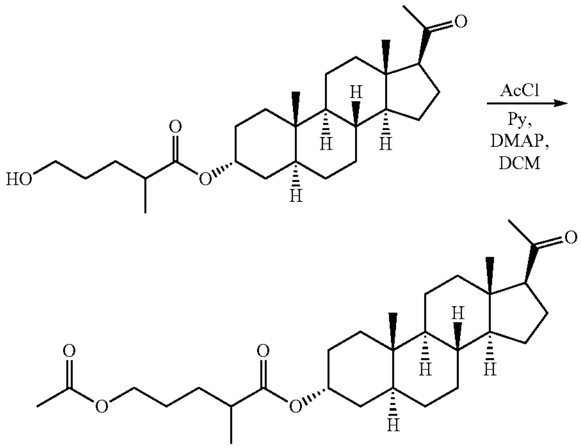

To a mixture of [(3R,5S,8R,9S,10S,13S,14S,17S)-17-acetyl-10,13-dimethyl-2, 3,4,5,6,7,8,9,11,12,14,15,16,17-tetradecahydro-1H-cyclopenta[a]phenanthren-3-yl] 5-hydroxy-2-methyl-pentanoate (80.0 mg, 0.19 mmol, 1.0 eq) in DCM (6 mL) was added acetyl chloride (43.6 mg, 0.55 mmol, 0.040 mL, 3.0 eq) and pyridine (73.1 mg, 0.93 mmol, 0.075 mL, 5.0 eq). Then the mixture was stirred at 25° C. for 4 h under $N_2$ atmosphere. The mixture was concentrated. The residue was purified by flash silica gel chromatography (ISCO®; 20 g SepaFlash® Silica Flash Column, Eluent of 0~20% Ethyl acetate/Petroleum ether gradient @30 mL/min). Compound [(3R,5S,8R,9S,10S,13S,14S,17S)-17-acetyl-10,13-dimethyl-2,3,4,5,6,7,8,9,11,12,14, 15,16,17-tetradecahydro-1H-cyclopenta[a]phenanthren-3-yl] 5-acetoxy-2-methyl-pentanoate (60.2 mg, 68.6% yield) was obtained as colorless solid. LCMS (ESI) m/z calcd for $C_{29}H_{46}O_3$ 5 474.33, found 497.2 $(M+Na)^+$. $^1H$ NMR (400 MHz, $CDCl_3$) δ (ppm) 5.03 (s, 1H), 4.07 (t, J=6.4 Hz, 2H), 2.55-2.42 (m, 2H), 2.21-2.12 (m, 4H), 2.06-1.99 (m, 4H), 1.78-1.64 (m, 8H), 1.55-1.13 (m, 16H), 1.00-0.89 (m, 1H), 0.82-0.75 (m, 4H), 0.61 (s, 3H). $^{13}C$ NMR (100 MHz, $CDCl_3$) δ (ppm) 209.78, 175.72, 171.15, 69.75, 64.26, 63.82, 56.69, 54.16, 44.23, 40.21, 39.43, 39.00, 35.80, 35.41, 33.00, 32.87, 32.84, 31.90, 31.54, 30.10, 30.03, 28.25, 26.31, 26.11, 26.05, 24.34, 22.74, 20.99, 20.78, 17.27, 17.16, 13.44, 11.31.

Example 18

3-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxy-carbonyloxy]propyl acetate

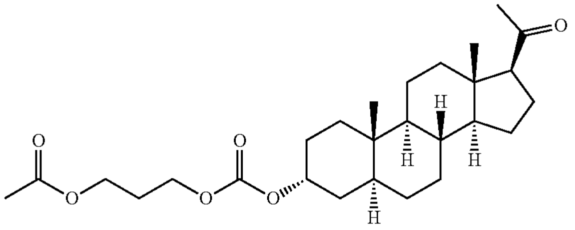

Step 1: Preparation of 3-benzyloxypropyl carbonochloridate

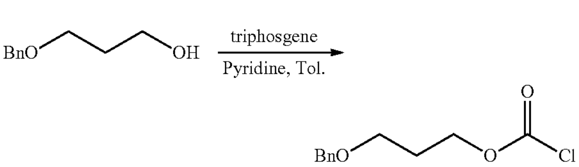

To a solution of triphosgene (8.93 g, 30.08 mmol, 5.0 eq) in toluene (20 mL) was added pyridine (714 mg, 9.02 mmol, 0.728 mL, 1.5 eq) at 0° C. Then 3-benzyloxypropan-1-ol (1.0 g, 6.02 mmol, 0.952 mL, 1.0 eq) was added and the mixture was stirred at 25° C. for 3 h. The mixture was diluted with DCM (40 mL) and washed with water (10 mL×3). The organic layer was concentrated to give 3-benzyloxypropyl carbonochloridate (150 mg, 52.4% yield) was obtained as colorless oil. $^1H$ NMR (400 MHz, $CD_3Cl$) δ (ppm) 7.42-7.34 (m, 5H), 4.55 (s, 2H), 4.90 (t, J=6.4 Hz, 2H), 3.60 (t, J=6.0 Hz, 2H), 2.07-2.03 (m, 2H).

Step 2: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-benzyloxypropyl carbonate

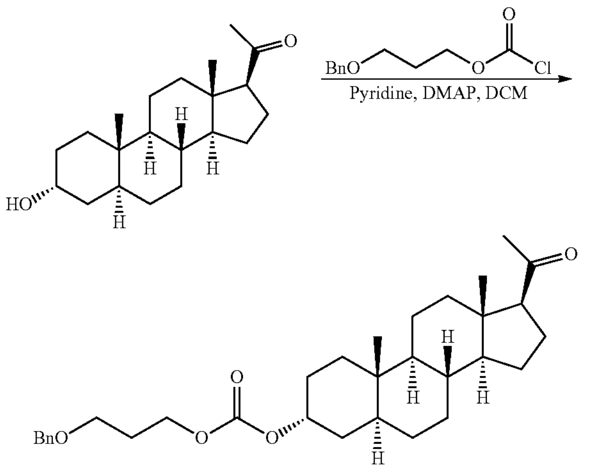

A solution of 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone (100 mg, 0.31 mmol, 1.0 eq) and DMAP (8 mg, 0.63 mmol, 0.2 eq) and pyridine (124 mg, 1.57 mmol, 0.126 mL, 5.0 eq) in DCM (2 mL) was stirred at 50° C. for 5 min and 3-benzyloxypropyl carbonochloridate (108 mg, 0.471 mmol, 1.5 eq) in DCM (1 mL) was added at 0° C. Then the mixture was stirred at 20° C. for 16 h. The mixture was diluted with water (5 mL) and extracted with EtOAc (10 mL×3). The organic layer was concentrated. The residue was purified by flash silica gel chromatography (ISCO®; 4 g SepaFlash® Silica Flash Column, eluted with 0~10% ethyl acetate/petroleum ether gradient @ 20 mL/min) to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-benzyloxypropyl carbonate (100 mg, 62.4% yield) as a white solid. LCMS (ESI) m/z calcd for $C_{32}H_{46}O_5$ 510.33, found 533.4 $(M+Na)^+$.

Step 3: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-hydroxypropyl carbonate

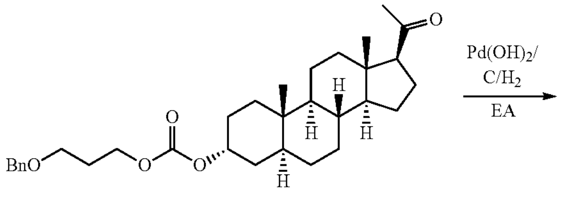

-continued

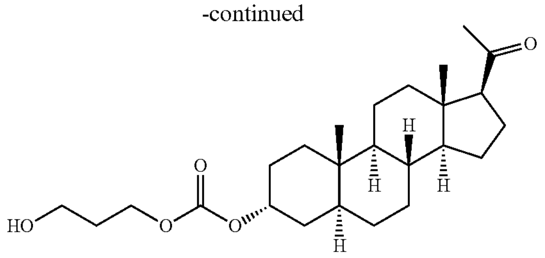

To a solution of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-benzyloxypropyl carbonate (90 mg, 0.18 mmol, 1.0 eq) in EtOAc (3 mL) was added $Pd(OH)_2/C$ (100 mg, 20% purity). The mixture was degassed and purged with $H_2$ for 3 times and stirred under $H_2$ (15 psi) at 25° C. for 16 h. The mixture was filtered, and the filtrate was concentrated. The residue was purified by flash silica gel chromatography (ISCO®; 4 g SepaFlash® Silica Flash Column, eluted with 0~25% ethyl acetate/petroleum ether gradient @ 20 mL/min) to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3 -hydroxypropyl carbonate (50 mg, 67.5% yield) as a white solid. $^1H$ NMR (400 MHz, $CD_3Cl$) δ (ppm) 4.91 (s, 1H), 4.31 (t, J=6.0 Hz, 2H), 4.75 (dd, J1=6.4 Hz, J2=11.6 Hz, 2H), 2.53 (t, J=8.8 Hz, 1H), 2.21-2.09 (m, 4H), 2.07-1.84 (m, 5H), 4.24-4.17 (m, 4H), 2.55-2.53 (m, 1H), 2.17-1.78 (m, 11H), 1.75-1.50 (m, 6H), 1.45-1.12 (m, 12H), 1.04-0.80 (m, 5H), 0.61 (s, 3H).

Step 4: Preparation of 3-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]propyl acetate

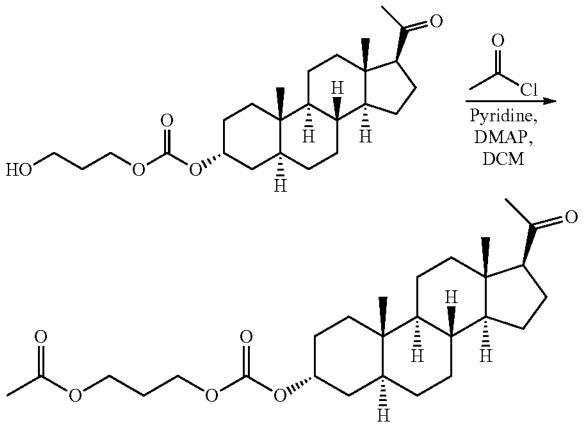

To a solution of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-hydroxypropyl carbonate (50.0 mg, 0.119 mmol, 1.0 eq), pyridine (38.0 mg, 0.48 mmol, 0.038 mL, 4.0 eq) and DMAP (8.0 mg, 0.059 mmol, 0.5 eq) in DCM (5 mL) was added acetyl chloride (19.0 mg, 0.24 mmol, 0.017 mL, 2.0 eq). Then the mixture was stirred at 25° C. for 16 h. The mixture was diluted with DCM (10 mL) and washed with water (5 mL×3) and brine (5 mL). The organic layer was dried ($Na_2SO_4$) and concentrated in vacuo. The resulting crude product was purified by flash silica gel chromatography (ISCO®; 4 g SepaFlash® Silica Flash Column, eluted with 0-20% ethyl acetate/petroleum ether gradient @ 20 mL/min) to give 3-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]propyl acetate (11.2 mg, 19.8% yield, 97% purity) as a white solid. LCMS (ESI) m/z calcd for $C_{27}H_{42}O_6$ 462.3, found 480.4 $(M+NH_4)^+$. $^1$H NMR (400 MHz, $CD_3C_1$) δ (ppm) 4.90 (s, 1H), 4.24-4.17 (m, 4H), 2.55-2.53 (m, 1H), 2.17-1.78 (m, 11H), 1.72-1.17 (m, 17H), 0.84-0.80 (m, 5H), 0.61 (s, 3H). $^{13}$C NMR (100 MHz, $CDCl_3$) δ (ppm) 209.73, 171.02, 154.76, 74.50, 64.21, 63.84, 60.95, 56.76, 53.87, 44.26, 39.69, 39.08, 35.78, 35.46, 32.82, 32.65, 31.75, 28.20, 28.04, 26.06, 24.38, 20.79, 13.47, 11.32.

Example 19

2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]ethyl 2-methylpropanoate

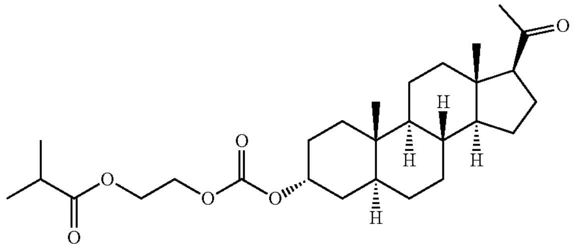

Step 1: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-hydroxyethyl carbonate

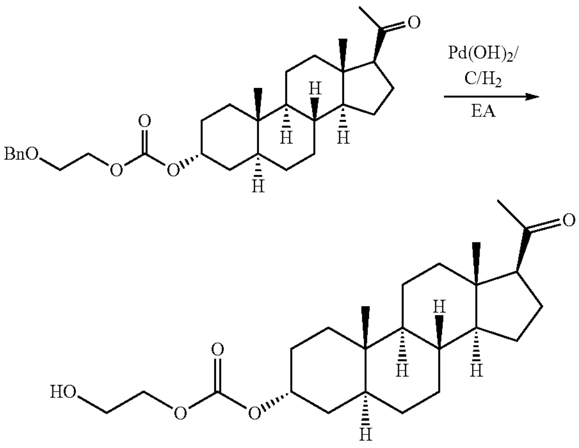

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-hydroxyethyl carbonate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-hydroxypropyl carbonate, except replacing 3-benzyloxypropanol with 2-benzyloxyethanol (1.2 g, 87.2% yield, colorless oil). The crude material was used directly for next step. $^1$H NMR (400 MHz, $CDCl_3$) δ (ppm) 4.93 (s, 1H), 4.27 (dd, J1=6.0 Hz, J2=4.4 Hz, 2H), 3.90-3.86 (m, 2H), 2.54 (t, J=9.2 Hz, 1H), 2.20-2.12 (m, 4H), 2.04-1.96 (m, 2H), 1.91-1.82 (m, 1H), 1.76-1.50 (m, 9H), 1.48-1.11 (m, 9H), 1.00-0.82 (m, 4H), 0.61 (s, 3H).

Step 2: Preparation of 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]ethyl 2-methylpropanoate

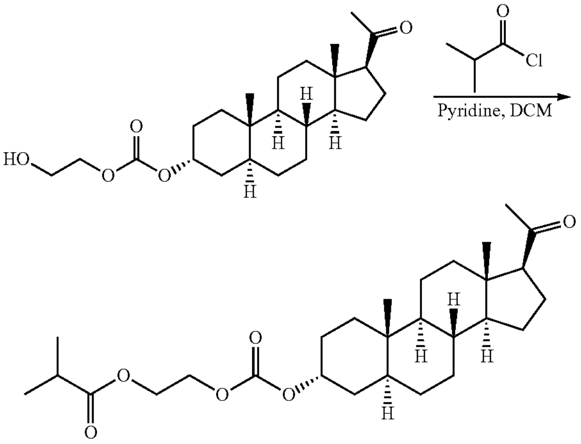

To a solution of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-hydroxyethyl carbonate (130 mg, 0.32 mmol, 1.0 eq) in DCM (5 mL) was added pyridine (101 mg, 1.28 mmol, 0.103 mL, 4.0 eq), DMAP (4.0 mg, 0.032 mmol, 0.1 eq) and 2-methylpropanoyl chloride (41.0 mg, 0.38 mmol, 0.040 mL, 1.2 eq) under $N_2$ atmosphere. Then the mixture was stirred at 20° C. for 16 h. The mixture was diluted with water (3 mL) and extracted with EtOAc (8 mL×3). The combined organic layers were washed with brine (50 mL), dried over $Na_2SO_4$, filtered and concentrated. The crude product was purified by flash silica gel chromatography (ISCO®; 12 g SepaFlash® Silica Flash Column, eluted with 0~15% ethyl acetate/petroleum ether gradient @ 20 mL/min) to give 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]ethyl 2-methylpropanoate (46.5 mg, 30.2% yield, 99% purity) as a white solid. LCMS (ESI) m/z calcd for $C_{28}H_{44}O_6$ 476.31, found 494.3 $(M+NH_4)^+$, 499.2 $(M+Na)^+$. $^1$H NMR (400 MHz, $CDCl_3$) δ (ppm) 4.91 (s, 1H), 4.36-4.34 (m, 2H), 4.34-4.31 (m, 2H), 2.63-2.56 (m, 1H), 2.55-2.51 (m, 1H), 2.19-2.12 (m, 4H), 2.02-1.96 (m, 1H), 1.87-1.84 (d, J=13.6 Hz, 2H), 1.69-1.63 (m, 4H), 1.613 (s, 2H), 1.54-1.50 (m, 4H), 1.40-1.39 (m, 2H), 1.29-1.22 (m, 3H), 1.19-1.16 (m, 8H), 1.00-0.90 (m, 1H), 0.86-0.82 (m, 1H), 0.80 (s, 3H), 0.61 (s, 3H). $^{13}$C NMR (100 MHz, $CDCl_3$)> (ppm) 209.25, 176.41, 154.10, 74.31, 64.73, 63.31, 61.45, 56.25, 53.35, 43.75, 39.15, 38.56, 35.25, 34.92, 33.35, 32.26, 32.11, 31.23, 31.05, 27.67, 25.51, 23.87, 22.28, 20.27, 18.43, 12.97, 10.82.

Example 20

[(3R,5S,8R,9S,10S,13S,14S,17S)-17-acetyl-10,13-dimethyl-2,3,4,5,6,7,8,9,11,12,14,15,16,17-tetra-decahydro-1H-cyclopenta[a]phenanthren-3-yl] (5-methyl-2-oxo-1,3-dioxol-4-yl)methyl carbonate

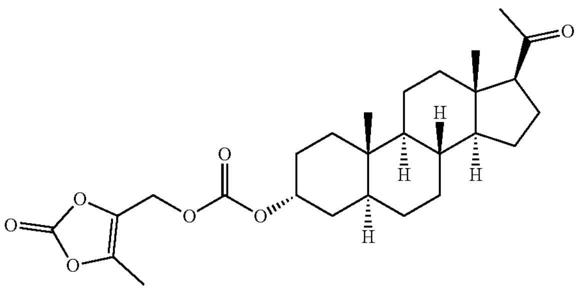

Method 1

Step 1: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]carbonochloridate

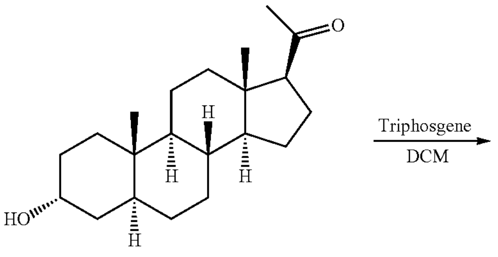

Brexanolone

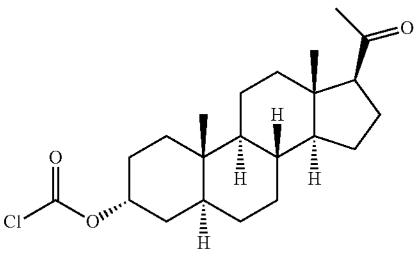

To a solution of triphosgene (3.49 g, 11.77 mmol, 2.5 eq) in toluene (20 mL) was added pyridine (559 mg, 7.06 mmol, 0.57 mL, 1.5 eq) at 0° C. The mixture was stirred at 0° C. for 15 min and 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone (1.50 g, 4.71 mmol, 1.0 eq) was added, and the resulting mixture was stirred at 25° C. for 5 h. The mixture was then diluted with water (15 mL) and extracted with DCM (20 mL×3). The organic layers were combined, washed with brine (15 mL), dried ($Na_2SO_4$) and concentrated in vacuo to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] carbonochloridate (1.1 g, 2.89 mmol, 61.3% yield) as a colorless solid, which was used directly for next step without further purification.

Step 2: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate

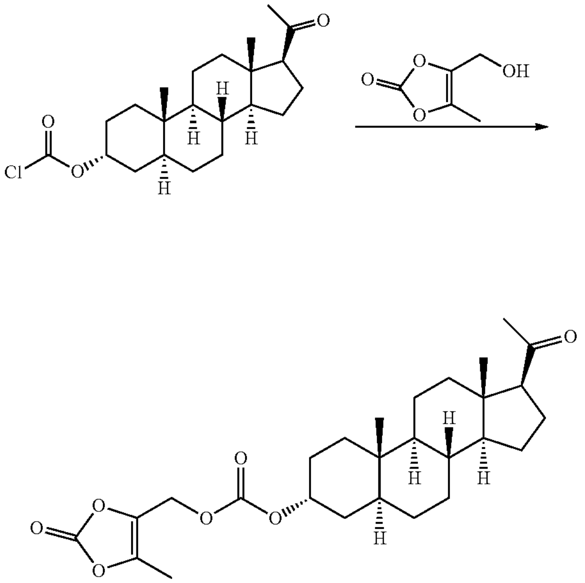

To a solution of 4-(hydroxymethyl)-5-methyl-1,3-dioxol-2-one (150 mg, 1.15 mmol, 1.0 eq), DMAP (14.0 mg, 0.12 mmol, 0.1 eq) and DIPEA (298 mg, 2.31 mmol, 0.40 mL, 2.0 eq) in DCM (9 mL) at room temperature was added [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]carbonochloridate (571 mg, 1.50 mmol, 1.3 eq). The resulting mixture was stirred at room temperature for 16 h. The mixture was then diluted with water (15 mL) and extracted with EtOAc (20 mL×3). The organic layers were combined, dried ($Na_2SO_4$) and concentrated in vacuo. The resulting crude product was purified by flash silica gel chromatography (ISCOR; 4 g SepaFlash® Silica Flash Column, eluted with 0-15% ethyl acetate/petroleum ether gradient @ 20 mL/min) to give desired product. The product was further purified through trituration with MeOH at 25° C. and the solid dried in vacuum to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate (276 mg, 0.57 mmol, 49.5% yield, 98% purity).

Method 2:

Step 1: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (4-nitrophenyl)carbonate

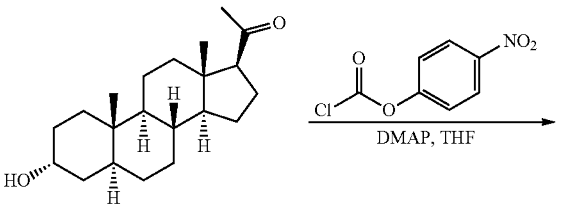

Brexanolone

-continued

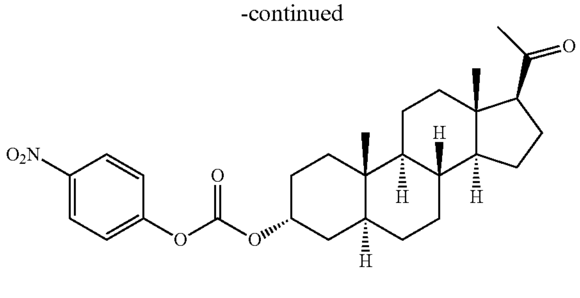

To a solution of 1-[(3R,5S,8R,9S,10S,13S,14S,17S)-3-hydroxy-10,13-dimethyl-2,3,4,5,6,7,8,9,11,12,14,15,16,17-tetradecahydro-1H-cyclopenta[a]phenanthren-17-yl]ethanone (3.0 g, 9.42 mmol, 1.0 eq) in THF (50 mL) were added DMAP (2.30 g, 18.8 mmol, 2.0 eq) and (4-nitrophenyl) carbonochloridate (3.80 g, 18.84 mmol, 2 eq). The reaction mixture was stirred at 25° C. for 16 h. Then iPrOH (1.13 g, 18.8 mmol, 1.44 mL, 2.0 eq) was added and the resulting mixture was stirred at 25° C. for 2 h. The mixture was diluted with EtOAc (70 mL) and washed with water (40 mL×3) and brine (50 mL). The organic layer was concentrated. The crude product was triturated with iPrOH (25 mL) at 25° C. for 5 min. The resulting mixture was filtered, the cake was dried under reduced pressure to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (4-nitrophenyl)carbonate (3.90 g, 87% yield) as a white solid. $^1$H NMR (400 MHz, $CDCl_3$) δ (ppm) 8.31-8.28 (m, 2H), 7.43-7.38 (m, 2H), 5.05 (s, 1H), 2.56-2.52 (t, J=8.8 Hz, 1H), 2.21-1.93 (m, 6H), 1.76-1.13 (m, 17H), 1.04-0.84 (m, 5H), 0.62 (s, 3H).

Step 2: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl) methyl carbonate

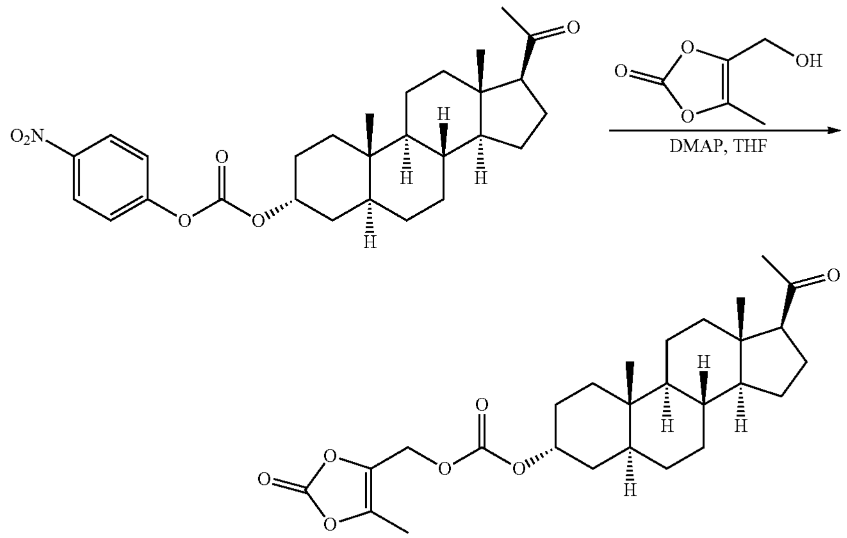

To a solution of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (4-nitrophenyl)carbonate (14.0 g, 28.4 mmol, 98% purity, 1.0 eq) and 4-(hydroxymethyl)-5-methyl-1,3-dioxol-2-one (7.38 g, 56.7 mmol, 2.0 eq) in THF (100 mL) was added DMAP (693 mg, 5.67 mmol, 0.2 eq). The mixture was stirred at 50° C. for 16 h. The mixture was diluted with EtOAc (200 mL) and washed with water (80 mL×2). The organic layer was washed with brine (80 mL), dried with $Na_2SO_4$, filtered and concentrated. The crude residue was triturated with iPrOH (70 mL) at 25° C. for 30 min. The mixture was filtered, and the cake was dried under reduced pressure to give [(3R,5S,8R,9S,10S,13S,14S,17S)-17-acetyl-10,13-dimethyl- 2,3,4,5,6,7,8,9,11,12,14,15,16,17-tetradecahydro-1H-cyclopenta[a]phenanthren-3-yl] (5-methyl-2-oxo-1,3-dioxol-4-yl) methyl carbonate (11.1 g, 82% yield) as a light yellow solid.

LCMS (ESI) m/z calcd for $C_{27}H_{38}O_7$ 474.26, found 475.3 $(M+H)^+$, 492.3 $(M+NH_4)^+$. $^1$H NMR (400 MHz, $CD_3Cl$) δ (ppm) 4.93 (s, 1H), 4.88 (s, 2H), 2.56-2.51 (t, J=9.2 Hz, 1H), 2.20-2.12 (m, 7H), 2.02-1.99 (d, J=12 Hz, 1H), 1.87-1.83 (d, J=16.4 Hz, 1H), 1.72-1.50 (m, 8H), 1.43-1.14 (m, 9H), 0.98-0.88 (m, 1H), 0.75-0.79 (m, 4H), 0.61 (s, 3H). 13C NMR (100 MHz, $CDCl_3$) δ (ppm) 209.72, 154.22, 152.00, 140.53, 133.16, 75.66, 63.81, 56.66, 53.86, 44.24, 39.67, 39.05, 35.76, 35.44, 32.77, 32.59, 31.72, 31.58, 28.17, 26.03, 24.38, 22.81, 20.79, 13.47, 11.32, 9.43.

Example 21

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]butyl carbonate

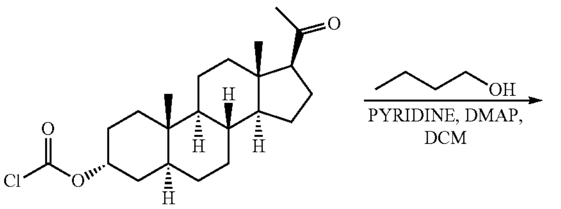

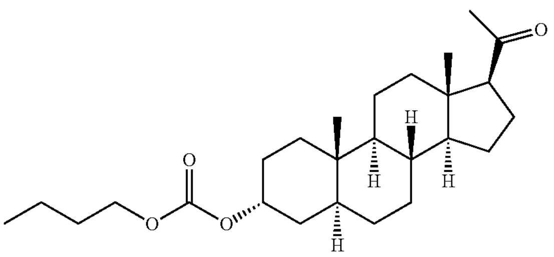

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]butyl carbonate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate, except changing 4-(hydroxymethyl)-5-methyl-1,3-dioxol-2-one to butan-1-ol. LCMS (ESI) m/z calcd for $C_{26}H_{42}O_4$ 418.31, found 419.3 $(M+H)^+$. $^1H$ NMR (400 MHz, $CDCl_3$) δ (ppm) 4.89 (s, 1H), 4.15-4.12 (t, J=6.8 Hz, 2H), 2.55-2.51 (t, J=8.8 Hz, 1H), 2.19-2.12 (m, 4H), 2.02-1.99 (d, J=11.2 Hz, 1H), 1.87-1.83 (d, J=16.4 Hz, 1H), 1.71-1.50 (m, 10H), 1.44-1.11 (m, 11H), 0.97-0.93 (t, J=7.2 Hz, 4H), 0.87-0.80 (m, 4H), 0.61 (s, 3H). $^{13}C$ NMR (100 MHz, $CDCl_3$) δ (ppm) 209.82, 154.94, 74.12, 67.55, 63.78, 56.71, 53.78, 44.23, 39.59, 39.03, 35.71, 35.38, 32.77, 32.59, 31.69, 31.54, 30.71, 28.15, 26.00, 24.33, 22.72, 20.73, 18.94, 13.69, 13.44, 11.28.

Example 22

2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonylamino]ethyl 2-methylpropanoate

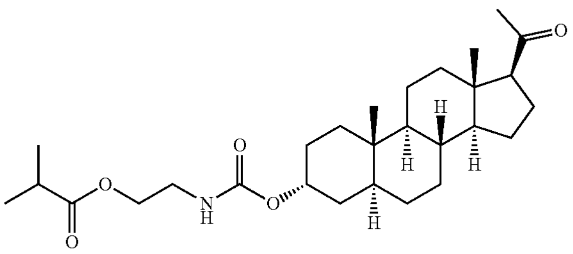

Step 1: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] N-(2-hydroxyethyl) carbamate

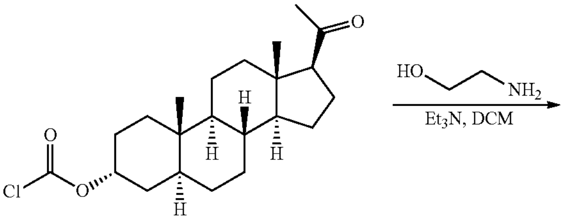

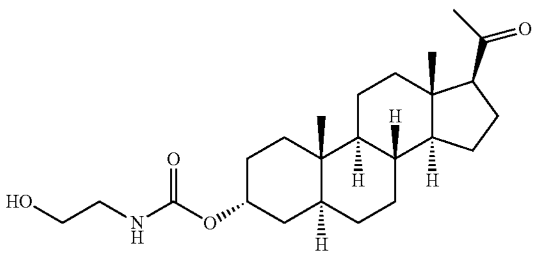

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] N-(2-hydroxyethyl) carbamate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate, except changing 4-(hydroxymethyl)-5-methyl-1,3-dioxol-2-one to 2-aminoethanol (650 mg, 61.1% yield).

Step 2: Preparation of 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonylamino]ethyl 2-methylpropanoate

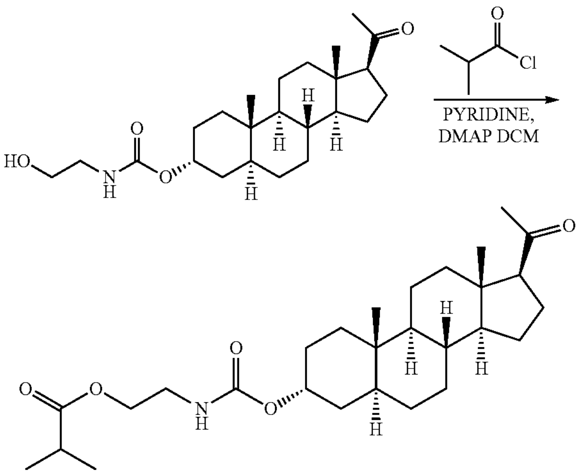

2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonylamino]ethyl 2-methylpropanoate was prepared following the same procedure as preparation of 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]ethyl 2-methylpropanoate except changing [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-hydroxyethyl carbonate to [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] N-(2-hydroxyethyl) carbamate (382 mg, 44.6% yield). LCMS (ESI) m/z calcd for $C_{28}H_{45}NO_5$ 475.33, found 498.3 $(M+Na)^+$. $^1H$ NMR (400 MHz, $CDCl_3$) δ (ppm) 4.93 (s, 1H), 4.86 (bs, 1H), 4.18-4.15 (t, J=5.6 Hz, 2H), 3.48-3.44 (m, 2H), 2.62-2.50 (m, 2H), 2.12-2.20 (m, 4H), 2.04-2.00 (m, 1H), 1.78-1.63 (m, 5H), 1.48-1.18 (m, 19H), 0.99-0.90 (m, 1H), 0.81-0.75 (m, 4H), 0.61 (s, 3H). $^{13}C$ NMR (100 MHz, $CD_3Cl$) δ (ppm) 209.74, 177.10, 156.22, 70.58, 63.82, 63.28, 56.77, 54.13, 44.23, 40.06, 39.96, 39.06, 35.78, 35.40, 33.88, 33.05, 32.86, 31.89, 31.52, 28.22, 26.28, 24.33, 22.73, 20.76, 18.97, 13.44, 11.31.

Example 23

2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyl-methyl-amino]ethyl 2-methylpropanoate

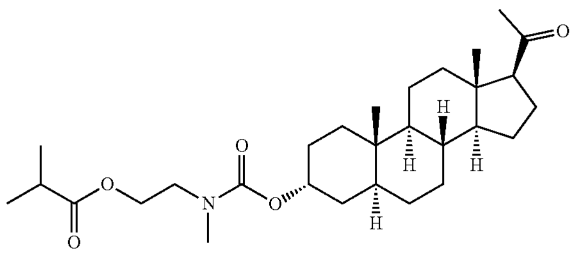

Step 1: Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] N-(2-hydroxyethyl)-N-methyl-carbamate

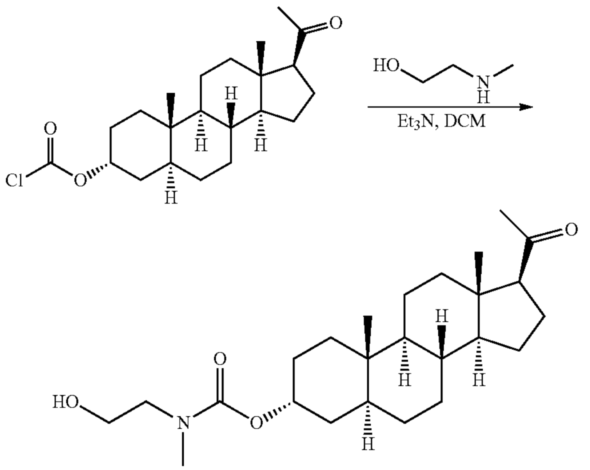

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] N-(2-hydroxyethyl)-N-methyl-carbamate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate, except changing 4-(hydroxymethyl)-5-methyl-1,3-dioxol-2-one to 2-(methylamino) ethanol (400 mg, 72.8% yield).

Step 2: Preparation of 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyl-methyl-amino]ethyl 2-methylpropanoate

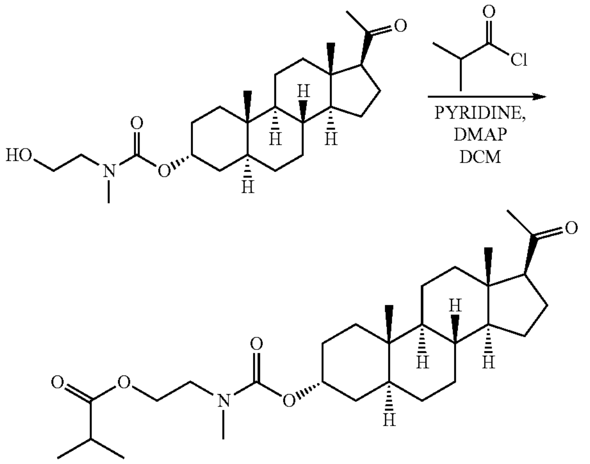

2-[[(3R,5S,8R,9S,10S,13S,14S,17S)-17-acetyl-10,13-dimethyl-2,3,4,5,6,7,8,9,11,12,14,15,16,17-tetradecahydro- 1H-cyclopenta[a]phenanthren-3-yl]oxycarbonyl-methyl-amino]ethyl 2-methylpropanoate was prepared following the same procedure as preparation of 2-[[(3R,5S,8R,9S,10S,13S,14S,17S)-17-acetyl-10,13-dimethyl- 2,3,4,5,6,7,8,9,11,12,14,15,16,17-tetradecahydro-1H-cyclopenta[a] phenanthren-3-yl]oxycarbonyloxy]ethyl 2-methylpropanoate except changing [(3R,5S,8R,9S,10S,13S,14S,17S)-17-acetyl-10,13-dimethyl-2-2,3,4,5,6,7,8,9,11,12,14,15,16,17-tetradecahydro-1H-cyclopenta[a] phenanthren-3-yl]hydroxyethyl carbonate to [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a] phenanthren-3-yl] N-(2-hydroxyethyl)-N-methyl-carbamate (280 mg, 59.4% yield). LCMS (ESI) m/z calcd for $C_{29}H_{47}NO_5$ 489.35, found 512.3 $(M+Na)^+$. $^1H$ NMR (400 MHz, $CDCl_3$) δ (ppm) 4.95 (s, 1H) 4.24-4.21 (t, J=5.6 Hz, 2H), 3.59-3.48 (m, 2H), 2.98 (s, 3H), 2.60-2.50 (m, 2H), 2.20-2.12 (m, 4H), 2.05-2.00 (m, 1H), 1.77-1.18 (m, 24H), 0.99-0.88 (m, 1H), 0.80-0.73 (m, 4H), 0.61 (s, 3H). $^{13}C$ NMR (100 MHz, $CDCl_3$) δ ppm 209.15, 176.36, 155.43, 70.41, 63.35, 61.77, 56.21, 53.83, 47.26, 43.74, 39.94, 38.54, 35.34, 35.09, 34.94, 34.51, 33.45, 32.78, 32.64, 31.00, 27.75, 25.90, 23.84, 22.27, 20.32, 18.44, 12.94, 10.89.

Example 24

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate)

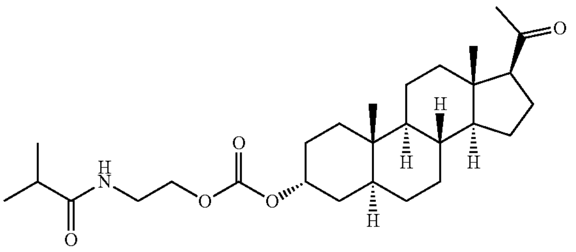

Preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate

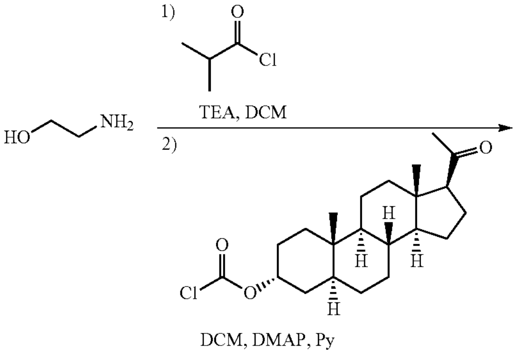

-continued

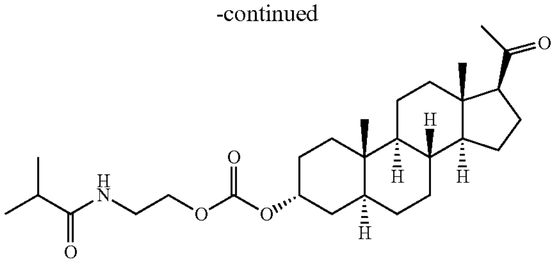

To a solution of 2-aminoethanol (200 mg, 3.27 mmol, 1.0 eq) in DCM (5 mL) was added TEA (993 mg, 9.81 mmol, 1.37 mL, 3.0 eq) at 0° C. followed by addition of 2-methylpropanoyl chloride (453 mg, 4.25 mmol, 0.444 mL, 1.3 eq) in DCM (5 mL). The reaction mixture was stirred at 25° C. for 16 h. Then DMAP (200 mg, 1.64 mmol, 0.5 eq) and [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]carbonochloridate (623 mg, 1.64 mmol, 0.5 eq) in DCM (5 mL) was added, then the mixture stirred at 25° C. for 16 h. The mixture was diluted with DCM (40 mL), and the organic layer was washed with water (30 mL) and brine (30 mL). The organic layer was dried over $Na_2SO_4$ and concentrated. The resulting residue was purified by flash silica gel chromatography (ISCO®; 12 g SepaFlash® Silica Flash Column, eluent of 0~40% ethyl acetate/petroleum ether gradient @35 mL/min). The compound was triturated with hexane (10 mL) at 25° C. for 16 h. The mixture was filtered, and the cake was triturated with hexane/EtOAc (5 mL/0.5 mL) at 25° C. for 1 h, then the mixture was filtered, the cake was dried to give [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a] phenanthren-3-yl] 2-(2-methyl propanoylamino)ethyl carbonate (254 mg, 16.3% yield) as a white solid. LCMS (ESI) m/z calcd for $C_{28}H_{45}NO_5$ 475.33, found 498.2 $(M+Na)^+$. $^1H$ NMR (400 MHz, $CDCl_3$) δ (ppm) 5.86 (br s, 1H), 4.92 (br s, 1H), 4.23 (t, J=5.2 Hz, 2H), 3.57 (q, J=5.6 Hz, 2H), 2.53 (t, J=8.8 Hz, 1H), 2.37-2.35 (m, 1H), 2.22-2.08 (m, 4H), 2.06-1.97 (m, 1H), 1.90-1.80 (m, 1H), 1.75-1.62 (m, 4H), 1.58-1.09 (m, 19H), 1.04-0.89 (m, 1H), 0.88-0.75 (m, 4H), 0.61 (s, 3H). 13C NMR (100 MHz, $CDCl_3$) δ (ppm) 209.71, 177.09, 154.79, 74.91, 66.58, 63.80, 56.73, 53.88, 44.23, 39.75, 39.04, 38.66, 35.75, 35.59, 35.40, 32.74, 32.64, 31.74, 31.52, 28.16, 25.99, 24.35, 22.77, 20.76, 19.54, 13.45, 11.30.

Example 25

(3R,5S,8R,9S,10S,13S,14S,17S)-17-acetyl-10,13-dimethylhexadecahydro-1H-cycl penta[a] phenanthren-3-yl(2-(N-methylisobutyramido)ethyl) carbonate

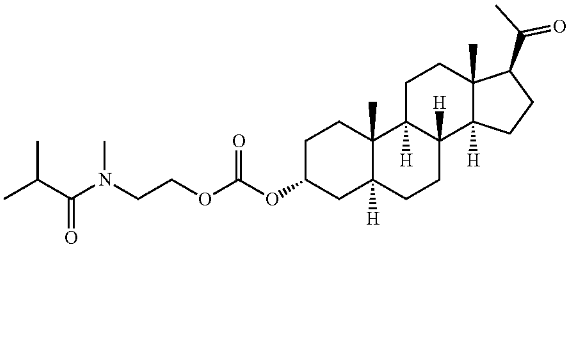

(3R,5S,8R,9S,10S,13S,14S,17S)-17-acetyl-10,13-dimethylhexadecahydro-1H-cycl penta[a]phenanthren-3-yl(2-(N-methylisobutyramido)ethyl)carbonate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate except replacing 2-aminoethanol with 2-(methylamino) ethanol (193 mg, 11.8% yield). LCMS (ESI) m/z calcd for $C_{29}H_{47}NO_5$ 489.35, found 512.3 $(M+Na)^+$. $^1H$ NMR (400 MHz, DMSO-$d_6$) δ (ppm) 4.77 (br d, J=8.8 Hz, 1H), 4.21-4.13 (m, 2H), 3.62-3.52 (m, 2H), 3.02 (s, 2H), 2.84-2.80 (m, 2H), 2.56 (br t, J=8.4 Hz, 1H), 2.03-1.91 (m, 2H), 1.68-1.17 (m, 20H), 0.99-0.96 (m, 8H), 0.76-0.72 (m, 4H), 0.50 (s, 3H). $^{13}C$ NMR (100 MHz, DMSO-$d_6$) δ (ppm) 208.57, 176.14, 153.99, 73.79, 64.13, 62.66, 55.93, 53.64, 47.52, 45.90, 43.50, 38.15, 35.37, 34.88, 32.99, 32.34, 31.47, 31.19, 29.35, 28.81, 27.72, 25.39, 23.90, 22.17, 20.32, 19.62, 19.06, 13.16, 11.04.

Example 26

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonylamino)ethyl carbonate

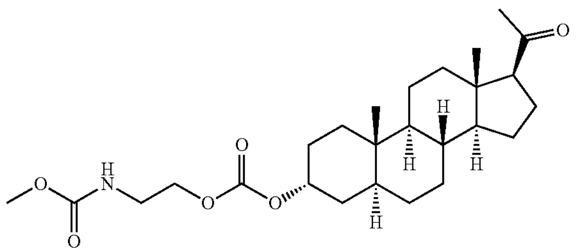

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonylamino) ethyl carbonate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate except replacing 2-aminoethanol 2-methylpropanoyl chloride with methyl carbonochloridate (109 mg, 17.9% yield). LCMS (ESI) m/z: calcd for $C_{26}H_{41}NO_6$ 463.29, found 486.3 $(M+Na)^+$. $^1H$ NMR (400 MHz, $CDCl_3$) δ (ppm) 5.04 (bs, 1H), 4.91 (s, 1H) 4.22-4.20 (t, J=5.2 Hz, 2H), 3.69 (s, 3H) 3.51-3.49 (d, J=5.2 Hz, 2H) 2.55-2.51 (t, J=8.8 Hz, 1H), 2.20-2.12 (m, 4H), 2.03-2.00 (m, 1H), 1.87-1.83 (d, J=14.8 Hz, 1H) 1.70-1.60 (m, 5H), 1.55-1.14 (m, 12H), 0.99-0.95 (m, 1H), 0.87-0.79 (m, 4H) 0.61 (s, 3H). $^1H$ NMR (400 MHz, DMSO-$d_6$) δ (ppm) 7.33-7.30 (t, J=5.2 Hz 1H), 4.78 (s, 1H) 4.05-4.03 (t, J=5.2 Hz, 2H), 3.52 (s, 3H), 3.22-3.21 (d, J=5.2 Hz, 2H), 2.58-2.54 (t, J=8.8 Hz, 1H), 2.07-1.95 (m, 4H), 1.69-1.09 (m, 18H), 0.93-0.89 (m, 1H), 0.86-0.71 (m, 4H), 0.50 (s, 3H). $^{13}C$ NMR (100 MHz, DMSO-$d_6$) δ (ppm) 209.02, 157.24, 154.49, 74.13, 66.31, 63.15, 56.38, 54.01, 51.80, 43.98, 38.63, 35.83, 35.38, 32.82, 32.67, 31.93, 31.66, 28.21, 25.87, 24.39, 22.66, 20.80, 13.63, 11.51.

Example 27

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonyl-N-methyl amino)ethyl carbonate

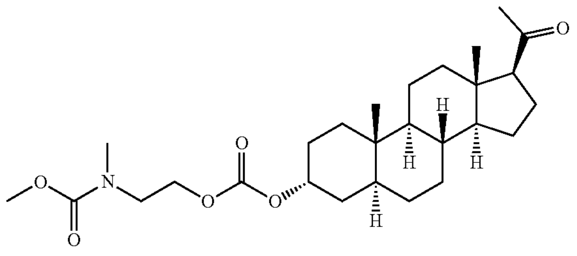

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonyl-N-methyl amino)ethyl carbonate was prepared following the same procedure as preparation of [(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate except replacing 2-aminoethanol 2-methylpropanoyl chloride with methyl carbonochloridate and 2-aminoethanol with 2-(methylamino) ethanol (143 mg, 23.1% yield). LCMS (ESI) m/z calcd for $C_{27}H_{43}NO_6$ 477.31, found 500.3 $(M+Na)^+$. $^1H$ NMR (400 MHz, DMSO-$d_6$) δ (ppm) 4.77 (s, 1H), 4.17-4.15 (t, J=5.2 Hz, 2H), 3.57 (s, 3H), 3.48-3.47 (d, J=4.8 Hz, 2H), 2.84 (s, 3H), 2.58-2.54 (t, J=8.8 Hz, 1H), 2.07-1.94 (m, 5H), 1.68-1.09 (m, 19H), 0.92-0.86 (m, 1H), 0.76-0.70 (m, 4H), 0.50 (s, 3H). $^{13}C$ NMR (100 MHz, DMSO-$d_6$) δ (ppm) 208.52, 156.13, 153.94, 73.68, 64.25, 62.63, 55.87, 53.50, 52.27, 47.29, 46.81, 43.47, 38.11, 35.33, 34.86, 34.17, 32.32, 32.13, 31.42, 31.16, 27.70, 25.37, 23.88, 22.15, 20.30, 13.13, 11.00.

Plasma Stability

The pooled frozen plasma was thawed in a water bath at 37° C. prior to experiment. Plasma was centrifuged at 4000 rpm for 5 min and the clots were removed if any. The pH will be adjusted to 7.4±0.1 if required.

Preparation of test compounds and positive control (propantheline bromide): 1 mM intermediate solution was prepared by diluting 10 μL of the stock solution with 90 μL MeOH; 1 mM intermediate of positive control Propantheline was prepared by diluting 10 μL of the stock solution with 90 μL ultrapure water. 100 μM dosing solution was prepared by diluting 20 μL of the intermediate solution (1 mM) with 180 μL MeOH. 98 μL of blank plasma was spiked with 2 μL of dosing solution (100 μM) to achieve 2 μM of the final concentration in duplicate and samples were incubated at 37° C. in a water bath. At each time point (0,10, 30, 60 and 120 min), 400 μL of stop solution (0.1% FA in MeOH containing 200 ng/ml tolbutamide and 200 ng/mL Labetalol) was added to precipitate protein and mixed thoroughly. Centrifuged sample plates at 4,000 rpm for 10 min. An aliquot of supernatant (100 μL) was transferred from each well to another plates.

Data analysis: The % remaining of test compound after incubation in plasma was calculated using following equation:

% Remaining=100×(PAR at appointed incubation time/PAR at T0 time)

where PAR is the peak area ratio of analyte versus internal standard (IS) (LC/MS/MS mobile phase condition: 0.1% Formic Acid in Water/0.1% Formic Acid in Acetonitrile. The appointed incubation time points are TO (0 min), Tn (n=0, 10, 30, 60, 120 min).

Liver S9 Stability

Intermediate solution: Dilute 5 µL of compounds or controls (7-ethoxycoumarin) from stock solution (10 mM) with 495 µL MeOH (Conc.: 100 µM, 1% DMSO, 99% MeOH). Stop solution: Cold ACN (including 100 ng/mL Tolbutamide and Labetalol as internal standard). Add 2 µL test compound or control working solution/well to all plates (T0, T5, T10, T20, T30, T60, NCF60) except matrix blank. Add 600 µL/well stop solution (cold in 4° C., including 100 ng/mL Tolbutamide/100 ng/ml Labetalol) to terminate the T0 plate, then put it on ice. Dispense 840 µL/well S9 solution to 96-well plate as reservoir according to plate map. Then add 100 µL/well to every plate by Apricot. Incubate S9 solution and compound at 37° C. for about 10 min except NCF60 and T0. After adding S9 solution and 98µ LPB buffer to NCF60, incubate at 37° C. without pre-warming, start timer 1. After 60 min, add 600 µL/well stop solution to terminate the reaction. After pre-warming, dispense 760 µL/well cofactor solution to 96-well plate as reservoir according to plate map. Then add 98 µL/well to every plate by Apricot to start reaction. Incubate at 37° C., start timer 2, Add 600 µL/well stop solution (cold in 4° C., including 100 ng/mL Tolbutamide and Labetalol) to terminate the reaction. Samples are centrifuged at 4000 rpm for 20 min. While centrifuging, load 8×new 96-well plate with 300 µL HPLC water, then transfer 100 µL supernatant, mix with water for LC/MS/MS, transferred to Bioanalytical Services for LC-MS/MS analysis. Use equation of first order kinetics to calculate $t_{1/2}$ and CL: Equation of first order kinetics:

$$C_t = C_0 \cdot e^{-k_e \cdot t}$$

$$C_t = \frac{1}{2}C_0,\ T_{1/2} = \frac{\text{Ln}\,2}{-k_e} = \frac{0.693}{-k_e}$$

$$CL_{int(S9)} = Vd \cdot k_e$$

$$Vd = 1\ \text{mL/mg}$$

The stability results of exemplary compounds in human plasma and human liver S9 are listed in Table 2 below.

TABLE 2

Stability results of exemplary compounds in human plasma and human liver S9.

| | Stability in Human Plasma | | Stability in Human Liver S9 | |
|---|---|---|---|---|
| Example | Half-life | Formation of parent compound | Half-life | Formation of parent compound |
| 1 | A | No | C | No |
| 2 | A | No | C | No |
| 8 | A | No | C | No |
| 14 | B | No | C | No |
| 15 | B | No | C | No |
| 16 | B | No | C | No |
| 17 | B | No | C | No |
| 19 | B | No | C | Yes |
| 20 | C | Yes | C | Yes |
| 21 | A | No | C | Yes |
| 22 | A | No | C | Yes |
| 23 | B | No | C | Yes |
| 24 | A | No | C | No |
| 25 | A | No | C | No |
| 27 | A | No | C | Yes |

Half-life ranges: A: >200 minutes; B: 50-200 minutes; C: <50 minutes.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise", "comprising", "include", "including", and "includes" when used in this specification and in the following claims are intended to specify the presence of stated features, integers, components, or steps, but they do not preclude the presence or addition of one or more other features, integers, components, steps, or groups thereof.

The invention is further described by the following numbered embodiments:

1. A compound of Formula (I):

(I)

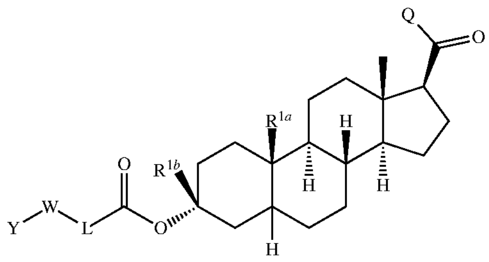

or a pharmaceutically acceptable salt thereof, wherein:

$R^{1a}$ and $R^{1b}$ each is independently hydrogen or methyl;

Q is methyl or

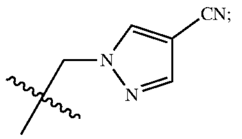 [SMILES: *Cn1cc(C#N)cn1]

L is selected from the group consisting of null, alkyl, —O—, and —N($R^2$)—;

W is selected from the group consisting of null, alkyl, and —O—;

Y is selected from the group consisting of alkyl, alkenyl, alkynyl, heteroalkyl, heteroalkenyl, heteroalkynyl, saturated or unsaturated cycloalkyl, saturated or unsaturated heterocyclyl, aryl, heteroaryl, —OC(O)OR$^3$, —OC(O)R$^4$, and —NR$^5$R$^6$, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl;

R$^2$, R$^3$, R$^4$ and R$^5$ are each independently selected from the group consisting of hydrogen, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, wherein said alkyl, alkenyl, alkynyl, heteroalkyl, heteroalkenyl, heteroalkynyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl;

R$^6$ is selected from the group consisting of hydrogen, alkyl, alkenyl, alkynyl, heteroalkyl, heteroalkenyl, heteroalkynyl, and —C(O)R$^7$; and R$^7$ is selected from the group consisting of hydrogen, alkyl, alkenyl, alkynyl, heteroalkyl, heteroalkenyl, heteroalkynyl, alkoxyl, saturated or unsaturated cycloalkyl, saturated or unsaturated heterocyclyl, aryl, and heteroaryl, wherein said alkyl, alkenyl, alkynyl, heteroalkyl, heteroalkenyl, heteroalkynyl, alkoxyl, saturated or unsaturated cycloalkyl, saturated or unsaturated heterocyclyl, aryl, and heteroaryl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl, with the provisos that when L is —O— or —N(R$^2$)—, W is not —O—, when W is —O—, Y is not —NR$^5$NR$^6$, and when W is —O—, Y is —C(O)OR$^3$ or —C(O) R$^4$.

2. The compound of Formula (I) or a pharmaceutically acceptable salt thereof, of embodiment 1, wherein R$^{1a}$ and R$^{1b}$ both are hydrogen.

3. The compound of Formula (I) or a pharmaceutically acceptable salt thereof, of embodiment 1, wherein R$^{1a}$ and R$^{1b}$ both are methyl.

4. The compound of Formula (I) or a pharmaceutically acceptable salt thereof, of embodiment 1, wherein R$^{1a}$ is methyl and R$^{1b}$ is hydrogen, or R$^{1a}$ is hydrogen and R$^{1b}$ is methyl.

5. The compound of Formula (I) or a pharmaceutically acceptable salt thereof, of any one of embodiments 1-4, wherein Q is methyl.

6. The compound of Formula (I) or a pharmaceutically acceptable salt thereof, of any one of embodiments 1-4, wherein Q is

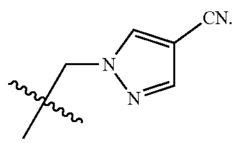 [SMILES: *Cn1cc(C#N)cn1]

7. The compound of Formula (I) or a pharmaceutically acceptable salt thereof, of any one of embodiments 1-6, wherein L is null.

8. The compound of Formula (I) or a pharmaceutically acceptable salt thereof, of any one of embodiments 1-6, wherein L is alkyl.

9. The compound of Formula (I) or a pharmaceutically acceptable salt thereof, of any one of embodiments 1-6, wherein L is —O—.

10. The compound of Formula (I) or a pharmaceutically acceptable salt thereof, of any one of embodiments 1-6, wherein L is —N(R$^2$)—, and R$^2$ is selected from the group consisting of hydrogen, alkyl, alkenyl, alkynyl, heteroalkyl, heteroalkenyl, and heteroalkynyl.

10a. The compound of Formula (I) or a pharmaceutically acceptable salt thereof, of embodiment 10, wherein L is —N(R$^2$)—, and R$^2$ is hydrogen or alkyl.

10b. The compound of Formula (I) or a pharmaceutically acceptable salt thereof, of embodiment 10 or 10a, wherein the alkyl is $C_1$-$C_6$ alkyl.

10c. The compound of Formula (I) or a pharmaceutically acceptable salt thereof, of embodiment 10b, wherein the $C_1$-$C_6$ alkyl is methyl.

11. The compound of Formula (I) or a pharmaceutically acceptable salt thereof, of any one of embodiments 1-10b, wherein W is null.

12. The compound of Formula (I) or a pharmaceutically acceptable salt thereof, of any one of embodiments 1-10b, wherein W is alkyl.

12a. The compound of Formula (I) or a pharmaceutically acceptable salt thereof, of embodiment 12, wherein the alkyl is a $C_1$-$C_7$ alkyl.

13. The compound of Formula (I) or a pharmaceutically acceptable salt thereof, of any one of embodiments 1-10b, wherein W is —O—.

14. The compound of Formula (I) or a pharmaceutically acceptable salt thereof, of embodiment 1, wherein L is null and W is null.

15. The compound of Formula (I) or a pharmaceutically acceptable salt thereof, of embodiment 1, wherein L is alkyl, and W is null or —O—.

16. The compound of Formula (I) or a pharmaceutically acceptable salt thereof, of embodiment 1, wherein L is —O—, and W is null or alkyl.

16a. The compound of Formula (I) or a pharmaceutically acceptable salt thereof, of embodiment 1, wherein L is —O— and W is alkyl.

17. The compound of Formula (I) or a pharmaceutically acceptable salt thereof, of embodiment 1, wherein L is —N(R$^2$)—, W is alkyl, and R$^2$ is selected from the group consisting of hydrogen, alkyl, alkenyl, alkynyl, heteroalkyl, heteroalkenyl, and heteroalkynyl.

17a. The compound of Formula (I) or a pharmaceutically acceptable salt thereof, of embodiment 1, wherein L is —N(R$^2$)—, W is alkyl, and R$^2$ is selected from the group consisting of hydrogen or alkyl.

17b. The compound of Formula (I) or a pharmaceutically acceptable salt thereof, of any one of embodiments 16-17a, wherein the alkyl is a $C_1$-$C_6$ alkyl.

18. The compound of Formula (I) or a pharmaceutically acceptable salt thereof, of any one of the preceding embodiments, wherein Y is selected from the group consisting of alkyl, saturated or unsaturated cycloalkyl, saturated or unsaturated heterocyclyl, —OC(O)OR$^3$ (or —C(O)OR$^3$ when W is —O—), —OC(O)R$^4$, and —NR$^5$R$^6$, wherein said alkyl, saturated or unsaturated cycloalkyl, and saturated or unsaturated heterocyclyl are optionally substituted with one or more groups independently selected from oxo, halogen, cyano, alkyl, alkenyl, alkynyl, heteroalkyl, heteroalkenyl, heteroalkynyl, saturated or unsaturated cycloalkyl, saturated or unsaturated heterocyclyl, aryl, and heteroaryl.

18a. The compound of Formula (I) or a pharmaceutically acceptable salt thereof, of any one of the preceding embodiments, wherein Y is unsaturated heterocyclyl, —OC(O)OR$^3$ (or —C(O)OR$^3$ when W is —O—), —OC(O)R$^4$, and —NR$^5$R$^6$, wherein said unsaturated heterocyclyl is optionally substituted with one or more groups independently selected from oxo, halogen, cyano, alkyl, alkenyl, alkynyl, and heteroalkyl.

18b. The compound of Formula (I) or a pharmaceutically acceptable salt thereof, of any one of embodiments 1-18a, wherein Y is optionally substituted unsaturated 5- or 6-membered heterocyclyl having 1 or 2 oxygen atoms.

18c. The compound of Formula (I) or a pharmaceutically acceptable salt thereof, of any one of embodiments 1-18b, wherein Y is

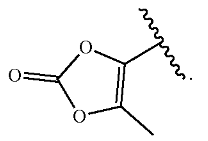 [SMILES: *c1oc(=O)oc1C]

18d. The compound of Formula (I) or a pharmaceutically acceptable salt thereof, of any one of embodiments 1-18a, wherein Y is —OC(O)R$^4$.

18e. The compound of Formula (I) or a pharmaceutically acceptable salt thereof, of embodiment 18d, R$^4$ is $C_1$-$C_6$ alkyl.

18f. The compound of Formula (I) or a pharmaceutically acceptable salt thereof, of embodiment 18e, wherein the $C_1$-$C_6$ alkyl is methyl, ethyl, or isopropyl.

18g. The compound of Formula (I) or a pharmaceutically acceptable salt thereof, of any one of embodiments 1-18a, wherein Y is —NR$^5$R$^6$.

18 h. The compound of Formula (I) or a pharmaceutically acceptable salt thereof, of embodiment 18g, wherein R$^5$ is H or alkyl and R$^6$ is —C(O)R$^7$.

18i. The compound of Formula (I) or a pharmaceutically acceptable salt thereof, of embodiment 18 h, wherein R$^7$ is $C_1$-$C_6$ alkyl or $C_1$-$C_6$ alkoxyl.

18j. The compound of Formula (I) or a pharmaceutically acceptable salt thereof, of embodiment 18i, wherein $C_1$-$C_6$ alkyl is —$CH_3$ or —$CH(CH_3)_2$ and $C_1$-$C_6$ alkoxyl-$OCH_3$ or —$OCH(CH_3)$ 2.

19. The compound of Formula (I) or a pharmaceutically acceptable salt thereof, of embodiment 1, wherein the compound has a Formula (Ia):

(Ia)

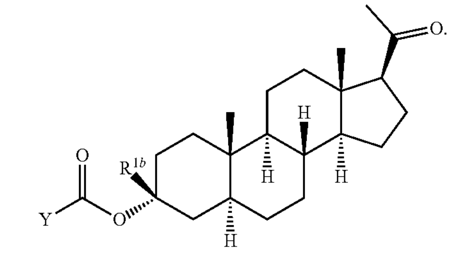

20. The compound of Formula (I) or a pharmaceutically acceptable salt thereof, of embodiment 19, wherein Y is alkyl.

21. The compound of Formula (I) or a pharmaceutically acceptable salt thereof, of embodiment 1, wherein the compound has a Formula (Ib):

(Ib)

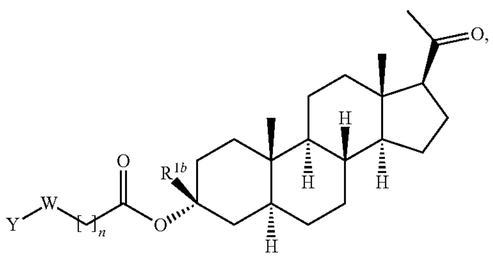

wherein

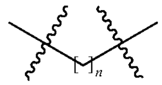

is optionally substituted with a $C_1$-$C_6$ alkyl group, and n is an integer in the range of 1-5.

22. The compound of Formula (I) or a pharmaceutically acceptable salt thereof, of embodiment 21, wherein W is —O—.

23. The compound of Formula (I) or a pharmaceutically acceptable salt thereof, of embodiment 21 or 22, wherein Y is saturated or unsaturated cycloalkyl, saturated or unsaturated heterocyclyl, or —C(O)OR$^3$, and R$^3$ is alkyl, wherein said cycloalkyl and heterocyclyl are optionally substituted with one or more groups independently selected from oxo, halogen, cyano, alkyl, alkenyl, and alkynyl.

23a. The compound of Formula (I) or a pharmaceutically acceptable salt thereof, of embodiment 22 or 23, wherein Y is —C(O)OR$^3$ and R$^3$ is $C_1$-$C_6$ alkyl.

23b. The compound of Formula (I) or a pharmaceutically acceptable salt thereof, of embodiment 23 or 23a, wherein Y is a 5- or 6-membered saturated or unsaturated cycloalkyl (e.g., cyclopentyl or cyclopentenyl).

23c. The compound of Formula (I) or a pharmaceutically acceptable salt thereof, of any one of embodiments 23-23b, wherein Y is a 5- or 6-membered heterocyclyl.

24. The compound of Formula (I) or a pharmaceutically acceptable salt thereof, of embodiment 1, wherein the compound has a Formula (Ic-1) or Formula (Ic-2):

(Ic-1)

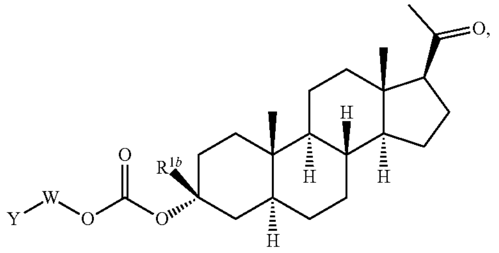

(Ic-2)

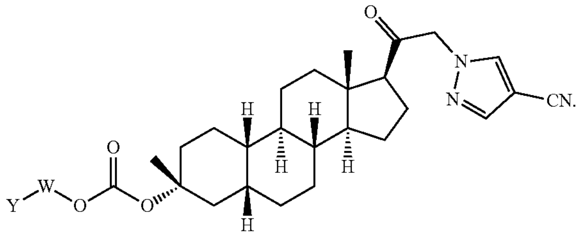

25. The compound of Formula (I) or a pharmaceutically acceptable salt thereof, of embodiment 1, wherein the compound has a Formula (Id-1) or Formula (Id-2):

(Id-1)

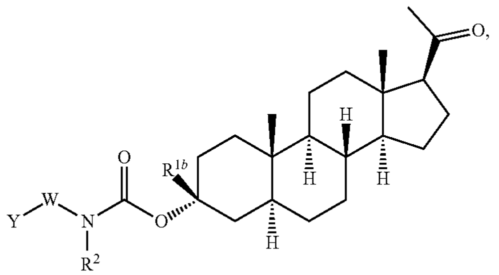

(Id-2)

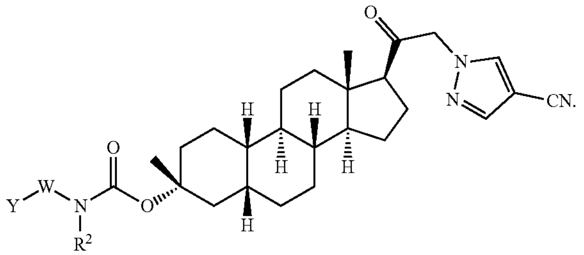

26. The compound of Formula (I) or a pharmaceutically acceptable salt thereof, of embodiment 24 or 25, wherein $R^{1b}$ is hydrogen.

27. The compound of Formula (I) or a pharmaceutically acceptable salt thereof, of embodiment 24 or 25, wherein $R^{1b}$ is methyl.

28. The compound of Formula (I) or a pharmaceutically acceptable salt thereof, of any one of embodiments 24-27, wherein $R^2$ is H, alkyl (e.g., $C_1$-$C_6$ alkyl), alkenyl (e.g., $C_2$-$C_6$ alkenyl) or alkynyl (e.g., $C_2$-$C_6$ alkynyl).

29. The compound of Formula (I) or a pharmaceutically acceptable salt thereof, of any one of embodiments 24-27, wherein $R^2$ is H or $C_1$-$C_6$ alkyl.

30. The compound of Formula (I) or a pharmaceutically acceptable salt thereof, of any one of embodiments 24-29, wherein W is optionally substituted alkyl.

31. The compound of Formula (I) or a pharmaceutically acceptable salt thereof, of embodiment 30, wherein the optionally substituted alkyl is a $C_1$-$C_6$ alkyl.

32. The compound of Formula (I) or a pharmaceutically acceptable salt thereof, of embodiment 30, wherein the optionally substituted alkyl is a $C_1$-$C_3$ alkyl.

33. The compound of Formula (I) or a pharmaceutically acceptable salt thereof, of any one of embodiments 24-32, wherein Y is unsaturated heterocyclyl, —OC(O)OR$^3$, —OC(O)R$^4$, and —NR$^5$R$^6$, wherein said unsaturated heterocyclyl is optionally substituted with one or more groups independently selected from oxo, halogen, cyano, alkyl, alkenyl, alkynyl, and heteroalkyl.

34. The compound of Formula (I) or a pharmaceutically acceptable salt thereof, of any one of embodiments 24-33, wherein Y is optionally substituted unsaturated 5- or 6-membered heterocyclyl having 1 or 2 oxygen atoms.

35. The compound of Formula (I) or a pharmaceutically acceptable salt thereof, of any one of embodiments 24-33, wherein Y is

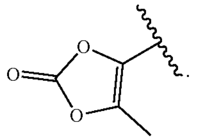 [SMILES: *c1oc(=O)oc1C]

36. The compound of Formula (I) or a pharmaceutically acceptable salt thereof, of any one of embodiments 24-33, wherein Y is —OC(O)R$^4$.

37. The compound of Formula (I) or a pharmaceutically acceptable salt thereof, of embodiment 36, $R^4$ is $C_1$-$C_6$ alkyl.

38. The compound of Formula (I) or a pharmaceutically acceptable salt thereof, of embodiment 37, wherein the $C_1$-$C_6$ alkyl is methyl, ethyl, or isopropyl.

39. The compound of Formula (I) or a pharmaceutically acceptable salt thereof, of any one of embodiments 24-33, wherein Y is —NR$^5$R$^6$.

40. The compound of Formula (I) or a pharmaceutically acceptable salt thereof, of embodiment 39, wherein $R^5$ is H or alkyl and $R^6$ is —C(O)R$^7$.

41. The compound of Formula (I) or a pharmaceutically acceptable salt thereof, of embodiment 40, wherein $R^7$ is $C_1$-$C_6$ alkyl or $C_1$-$C_6$ alkoxyl.

41a. The compound of Formula (I) or a pharmaceutically acceptable salt thereof, of embodiment 41, wherein $C_1$-$C_6$ alkyl is —$CH_3$ or —$CH(CH_3)_2$ and $C_1$-$C_6$ alkoxyl-$OCH_3$ or —$OCH(CH_3)$ 2.

42. The compound of Formula (I) or a pharmaceutically acceptable salt thereof, of any one of embodiments 24-33, wherein Y is —OC(O)OR$^3$.

42a. The compound of Formula (I) or a pharmaceutically acceptable salt thereof, of embodiment 42, $R^3$ is alkyl (e.g., $C_1$-$C_6$ alkyl) or aryl (phenyl), each of which is optionally substituted.

43. The compound of any one of preceding claims or a pharmaceutically acceptable salt thereof, wherein the compound is selected from the group consisting of:

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]hexanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] heptanoate, (3R,5S,8R,9S,10S,13S,14S,17S)-17-acetyl-10,13-dimethylhexadecahydro-1H-cyclopenta[a]phenanthren-3-yl octanoate,

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]hexanoate,

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]heptanoate,

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl]octanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopentylacetate,

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 3-cyclopentylpropanoate,

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 2-cyclopentylacetate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-cyclopent-3-en-1-ylpropanoate,

[(3R,5S,8R,9S,10S,13S,14S,17S)-17-acetyl-3,10,13-trimethyl-1,2,4,5,6,7,8,9,11,12,14,15,16,17-tetradecahydrocyclopenta[a]phenanthren-3-yl] 3-cyclopent-3-en-1-ylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 3-(5-oxotetrahydrofuran-2-yl)propanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-acetoxybutanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 4-(2-methylpropanoyloxy) butanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 5-acetoxyp entanoate,

[(3R,5S,8R,9S,10S,13S,14S,17S)-17-acetyl-10,13-dimethyl-2,3,4,5,6,7,8,9,11,12,14, 15,16,17-tetradecahydro-1H-cyclopenta[a]phenanthren-3-yl] 5-acetoxy-2-methylpentanoate, 3-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy]propyl acetate, 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyloxy] ethyl 2-methylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] (5-methyl-2-oxo-1,3-dioxol-4-yl)methyl carbonate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] butyl carbonate, 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonylamino] ethyl 2-methylpropanoate, 2-[[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl]oxycarbonyl-methyl-amino]ethyl 2-methylpropanoate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(2-methyl propanoylamino)ethyl carbonate), (3R,5S,8R,9S,10S,13S,14S,17S)-17-acetyl-10,13-dimethylhexadecahydro-1H-cycl penta[a]phenanthren-3-yl(2-(N-methylisobutyramido)ethyl)carbonate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonylamino)ethyl carbonate,

[(3R,5S,8R,9S,10S,13S,14S,17S)-17-acetyl-10,13-dimethyl-2,3,4,5,6,7,8,9,11,12,14,15,16,17-tetradecahydro-1H-cyclopenta[a]phenanthren-3-yl] 2-(methoxycarbonyl-N-methyl amino)ethyl carbonate, (3R,5S,8R,9S,10S,13S,14S,17S)-17-acetyl-3,10,13-trimethylhexadecahydro-1H-cyclopenta[a]phenanthren-3-yl ((5-methyl-2-oxo-1,3-dioxol-4-yl)methyl) carbonate, 2-(((((3R,5S,8R,9S,10S,13S,14S,17S)-17-acetyl-3,10,13-trimethylhexadecahydro-1H-cyclopenta[a]phenanthren-3-yl)oxy)carbonyl)(methyl)amino)ethyl isobutyrate, 2-(((((3R,5S,8R,9S,10S,13S,14S,17S)-17-acetyl-3,10,13-trimethylhexadecahydro-1H-cyclopenta[a]phenanthren-3-yl)oxy)carbonyl)oxy)ethyl isobutyrate, (3R,5R,8R,9R,10S,13S,14S,17S)-17-(2-(4-cyano-1H-pyrazol-1-yl) acetyl)-3,13-dimethylhexadecahydro-1H-cyclopenta[a]phenanthren-3-yl ((5-methyl-2-oxo-1,3-dioxol-4-yl)methyl)carbonate, 2-(((((3R,5R,8R,9R,10S,13S,14S,17S)-17-(2-(4-cyano-1H-pyrazol-1-yl) acetyl)-3,13-dimethylhexadecahydro-1H-cyclopenta[a]phenanthren-3-yl)oxy)carbonyl)(methyl) amino)ethyl isobutyrate, and 2-(((((3R,5R,8R,9R,10S,13S,14S,17S)-17-(2-(4-cyano-1H-pyrazol-1-yl) acetyl)-3,13-dimethylhexadecahydro-1H-cyclopenta[a]phenanthren-3-yl)oxy)carbonyl)oxy)ethyl isobutyrate.

44. A pharmaceutical composition comprising a compound of Formula (I) or pharmaceutically acceptable salt thereof, of any one of the preceding embodiments, and at least one pharmaceutically acceptable excipient.

45. A method of treating a disease or condition related to $GABA_A$ receptor function in a subject in need thereof, comprising administering to the subject a therapeutically effective amount of a compound of Formula (I) or a pharmaceutically acceptable salt thereof, of any one of the embodiments 1 to 43.

46. The method of embodiment 45, wherein the disease or condition is selected from the group consisting of a sleep disorder, a mood disorder, a dementia, a schizophrenia spectrum disorder, a convulsive disorder, an anxiety disorder, an autism spectrum disorder, a disorder of memory and/or cognition, a movement disorder, a personality disorder, an autism spectrum disorder, pain, traumatic brain injury, a vascular disease, a substance abuse disorder, a withdrawal syndrome, and tinnitus.

46a. The method of embodiment 46, wherein the sleep disorder is insomnia, the mood disorder is depression, the dementia is Alzheimer's type dementia, the convulsive disorder is epilepsy, and the movement disorder is Parkinson's disease.

46b. The method of embodiment 46, wherein the disease is selected from the group consisting of CDD, MDD, PPD, essential tremor, PTSD, SE, ESE, Fragile X syndrome, Parkinson's Disease, or treatment resistant depression.

47. A compound of Formula (I) or a pharmaceutically acceptable salt thereof, of any one of embodiments 1 to 43, for use in the treatment of a disease or condition related to $GABA_A$ receptor function.

48. Use of a compound of Formula (I) or a pharmaceutically acceptable salt thereof, of any one of embodiments 1 to 43, in the manufacture of a medicament for the treatment of a disease or condition related to $GABA_A$ receptor function.

49. A compound of Formula (I) or a pharmaceutically acceptable salt thereof, of any one of embodiments 1 to 43, for use in the treatment of a disease or condition related to $GABA_A$ receptor function, wherein the compound of Formula (I) is administered simultaneously, separately or sequentially with one or more additional agents.

What is claimed is:

1. A compound having the structure:

(19)

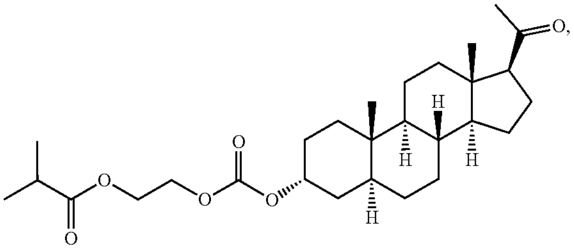

(30)

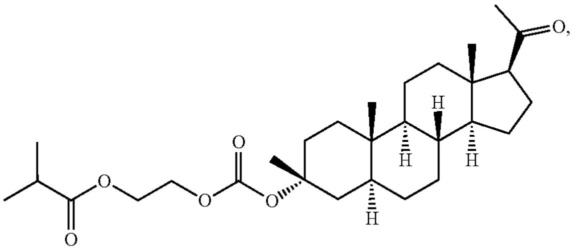

-continued (20)

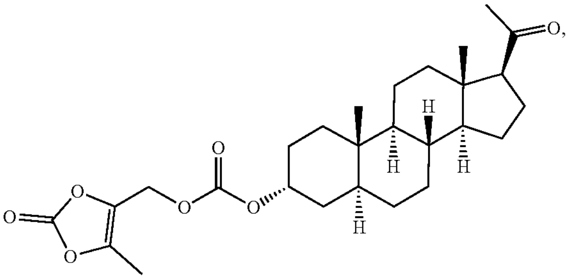

(28)

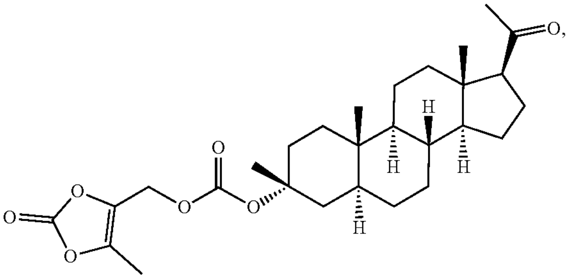

(23)

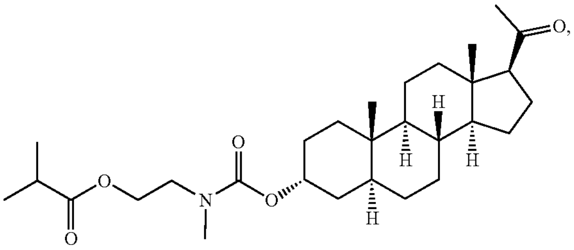

(22)

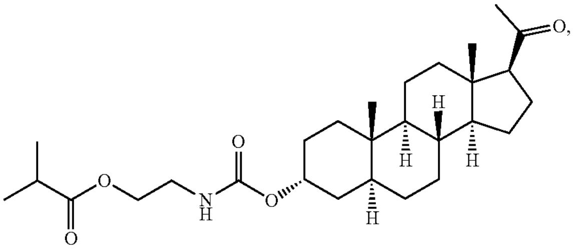

(27)

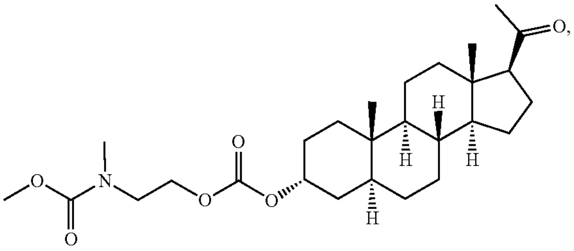

-continued
(29)
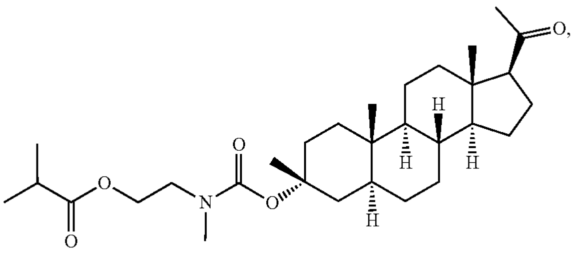
(31)
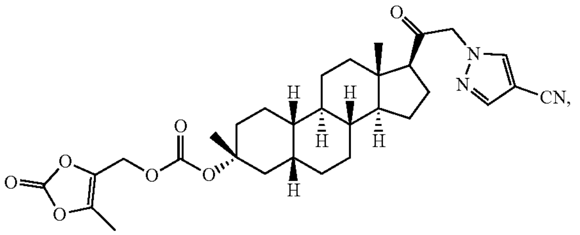
(32)
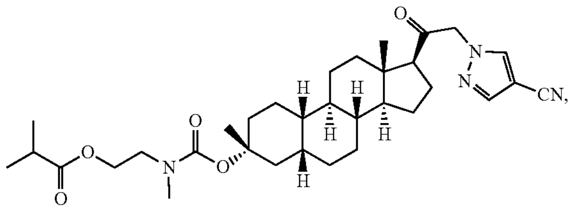
-continued
(33)
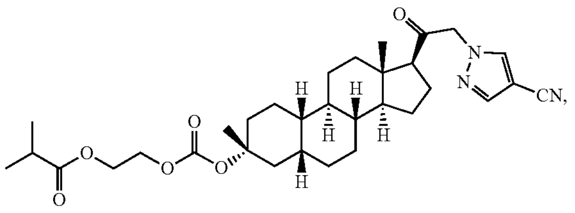
or a pharmaceutically acceptable salt thereof.
2. A pharmaceutical composition comprising the compound or pharmaceutically acceptable salt thereof of claim 1 and at least one pharmaceutically acceptable excipient.
3. The compound of claim 1, wherein the compound is:
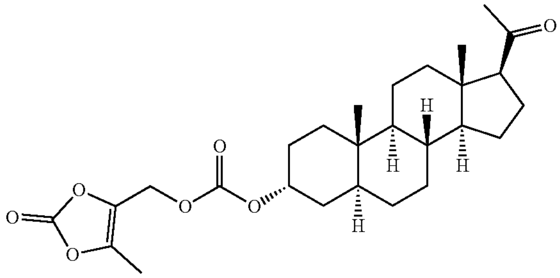
or a pharmaceutically acceptable salt thereof.
* * * * *